United States Patent [19]

Hemmi et al.

[11] Patent Number: 5,223,489
[45] Date of Patent: Jun. 29, 1993

[54] AMINO ACID DERIVATIVES, PROCESSES FOR THE PREPARATION THEREOF AND PHARMACEUTICAL COMPOSITION COMPRISING THE SAME

[75] Inventors: Keiji Hemmi; Masahiro Neya; Hiroshi Marusawa, all of Tsukuba; Keisuke Imai, Sapporo; Natsuko Kayakiri; Masashi Hashimoto, both of Tsukuba, all of Japan

[73] Assignee: Ujisawa Pharmaceutical Co., Ltd., Osaka, Japan

[ * ] Notice: The portion of the term of this patent subsequent to May 1, 2007, has been disclaimed.

[21] Appl. No.: 828,193

[22] Filed: Jan. 30, 1992

Related U.S. Application Data

[62] Division of Ser. No. 462,117, Jan. 8, 1990, Pat. No. 5,142,048, which is a division of Ser. No. 204,549, Jun. 9, 1988, Pat. No. 4,921,855.

[30] Foreign Application Priority Data

Jun. 22, 1987 [GB] United Kingdom ............... 8714597
Oct. 30, 1987 [GB] United Kingdom ............... 8725511
Mar. 7, 1988 [GB] United Kingdom ............... 8805389

[51] Int. Cl.$^5$ .................... A61K 31/16; C07D 279/12; C07D 217/12
[52] U.S. Cl. ..................... 514/19; 540/603; 544/58.2; 544/58.4; 544/139; 544/238; 544/349; 546/146; 546/147; 546/210; 546/278; 548/200; 548/201; 548/236; 548/338.1; 548/338.5; 548/312.4; 548/314.7
[58] Field of Search ............... 548/344, 200, 201, 236, 548/336; 544/139, 238, 58.2, 58.4, 349; 514/19; 546/278, 210, 146, 147

[56] References Cited

U.S. PATENT DOCUMENTS

| 4,826,815 | 5/1989 | Luly et al. ............. 548/344 |
| 4,845,079 | 7/1989 | Luly et al. ............. 548/344 |

Primary Examiner—Johann Richter
Attorney, Agent, or Firm—Oblon, Spivak, McClelland, Maier & Neustadt

[57] ABSTRACT

A compound of the formula:

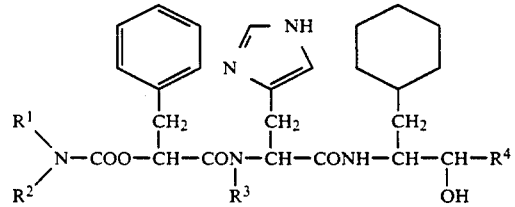

wherein
  $R^1$ is lower alkyl optionally substituted aryl; or amino optionally substituted; and
  $R^2$ is hydrogen or lower alkyl; or
  $R^1$ and $R^2$ are taken together with the attached nitrogen atom to form a heterocyclic group optionally substituted;
  $R^3$ is hydrogen or lower alkyl; and
  $R^4$ is lower alkyl;

and its pharmaceutically acceptable salt, processes for the preparation thereof and pharmaceutical composition comprising the same

10 Claims, No Drawings

AMINO ACID DERIVATIVES, PROCESSES FOR THE PREPARATION THEREOF AND PHARMACEUTICAL COMPOSITION COMPRISING THE SAME

This is a division of application Ser. No. 07/462,117, filed on Jan. 8, 1990 now U.S. Pat. No. 4,142,048 which is a division of application Ser. No. 07/204,549 filed on Jun. 9, 1988 now U.S. Pat. No. 4,921,855.

This invention relates to new amino acid derivatives and pharmaceutically acceptable salts thereof.

More particularly, it relates to new amino acid derivatives and pharmaceutically acceptable salts thereof which have inhibitory activities against renin, to processes for the preparation thereof, to a pharmaceutical composition comprising the same and to a method for the treatment of hypertension and heart failure in human being or animals.

One object of this invention is to provide new and useful amino acid derivatives and pharmaceutically acceptable salts thereof which possess inhibitory activities against renin, and which are useful as a hypotensor and a therapeutic agent on heart failure, especially for oral administration.

Another object of this invention is to provide processes for the preparation of said amino acid derivatives and salts thereof.

A further object of this invention is to provide a pharmaceutical composition comprising, as an active ingredient, said amino acid derivatives and pharmaceutically acceptable salts thereof.

Still further object of this invention is to provide a therapeutical method for the treatment of hypertension and heart failure.

Some renin inhibitors possessing similar structures to those of our object amino acid derivatives have been known as described in European Patent Application Publication Nos. 172,346 and 229,667.

The object amino acid derivatives of this invention are new and can be represented by the following general formula [I]:

wherein
R$^1$ is lower alkyl optionally substituted with a substituent selected from the group consisting of acyl, hydroxy, lower alkoxy, aryl, lower alkylthio and a group of the formula:

$$-N\begin{matrix}R^5\\R^6\end{matrix}$$

in which
R$^5$ is hydrogen or acyl and
R$^6$ is hydrogen or lower alkyl; aryl; or amino optionally substituted with substituent(s) selected from the group consisting of lower alkyl and acyl; and
R$^2$ is hydrogen or lower alkyl; or
R$^1$ and R$^2$ are taken together with the attached nitrogen atom to form a heterocyclic group optionally substituted with substituent(s) selected from the group consisting of lower alkyl, hydroxy(lower)alkyl, lower alkoxy(lower)alkyl, acyl(lower)alkyl, oxo and acyl;
R$^3$ is hydrogen or lower alkyl; and
R$^4$ is lower alkyl.

The object compound [I] or its salt can be prepared by processes as illustrated in the following reaction schemes, but preparations of the object compound [I] are not limited to the following processes.

Process 1

Step 1

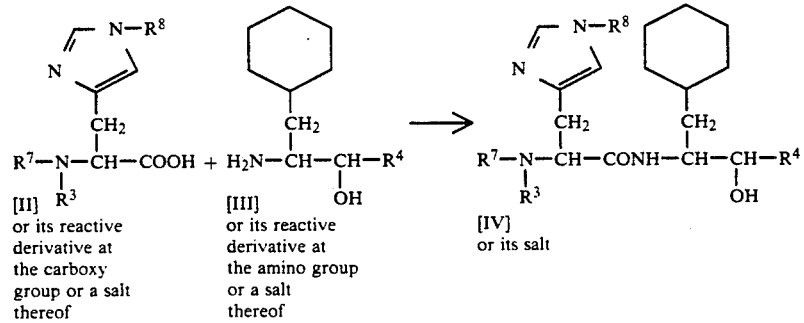

Step 2

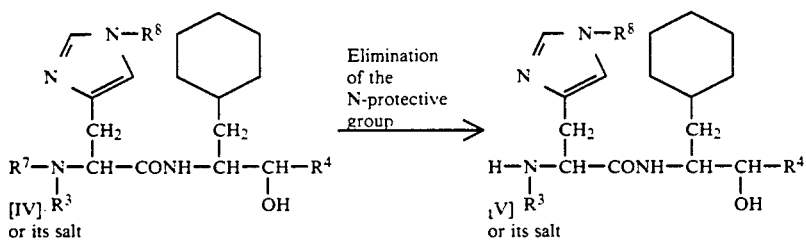

Step 3

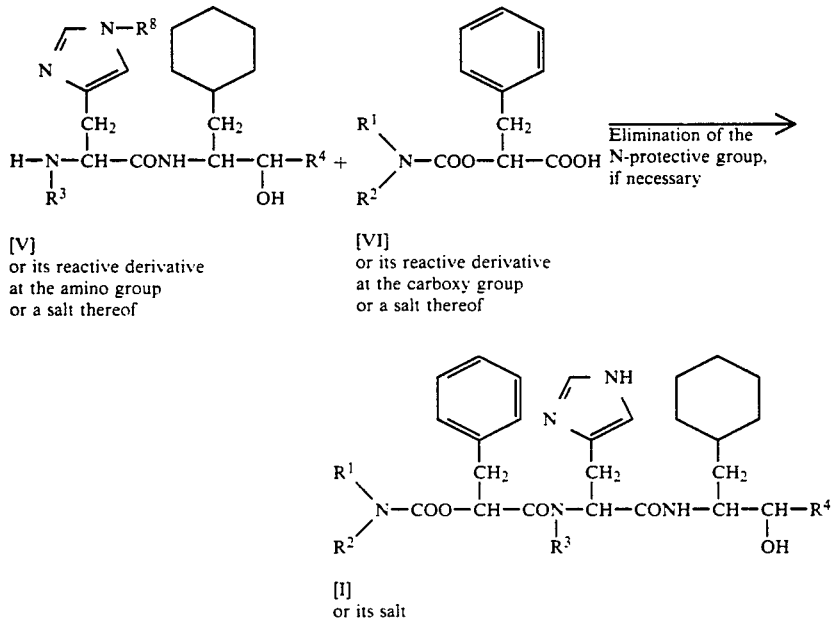

Process 2

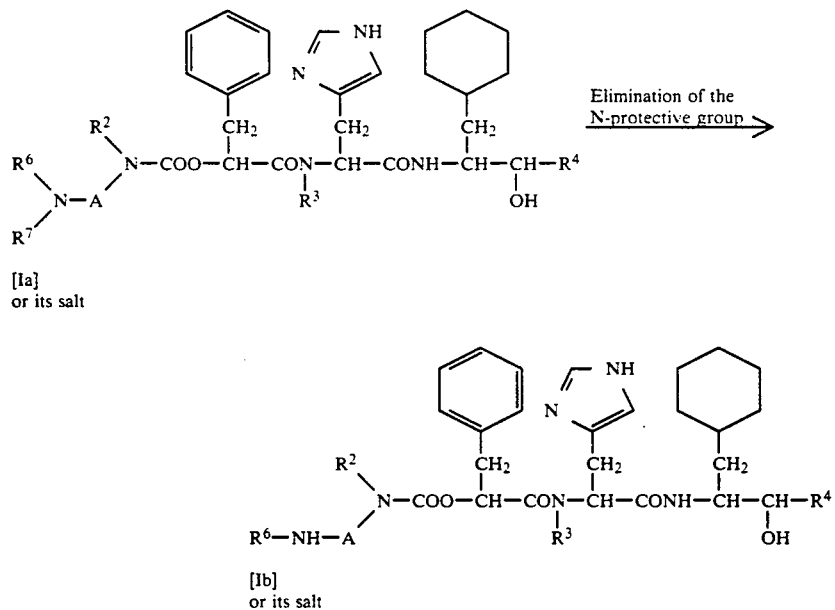

wherein
$R^7$ is an N-protective group,
$R^8$ is hydrogen or an N-protective group,
A is lower alkylene, and
$R^1$, $R^2$, $R^3$, $R^4$ and $R^6$ are each as defined above.

In the above and subsequent description of the present specification, suitable examples of the various definitions to be included within the scope of the invention are explained in detail in the following.

The term "lower" is intended to mean a group having 1 to 7 carbon atom(s), unless otherwise provided.

Suitable "lower alkyl" may be a straight or branched one such as methyl, ethyl, propyl, isopropyl, butyl, isobutyl, tert-butyl, pentyl, isopentyl, hexyl, methylhexyl, heptyl, and the like.

Suitable "acyl" and "acyl" moiety in the term "acyl(lower)alkyl" may be a group of the formula:

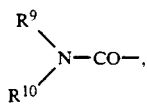

R$^{11}$—CO— and R$^{11}$—SO$_2$—,
wherein
- R$^9$ and R$^{10}$ are each hydrogen, aryl, cyclo(lower)alkyl, a heterocyclic group or lower alkyl optionally substituted with a substituent selected from the group consisting of lower alkoxycarbonyl, lower alkoxy, aryl and a heterocyclic group, or
- R$^9$ and R$^{10}$ are taken together with the attached nitrogen atom to form a heterocyclic group optionally substituted with lower alkyl, and
- R$^{11}$ is aryl, cyclo(lower)alkyl, lower alkyl optionally substituted with a substituent selected from the group consisting of lower alkoxy and mono- or di(lower)alkylamino, or lower alkoxy optionally substituted with a substituent selected from the group consisting of lower alkanoyl and aryl, amino-protected or unprotected amino acid residue, or the like.

Suitable "aryl" may be phenyl, naphthyl, tolyl, xylyl, mesityl, cumenyl, and the like, in which preferable one is phenyl.

Suitable "cyclo(lower)alkyl" is cyclopropyl, cyclobutyl, cyclopentyl, cyclohexyl, or the like.

Suitable "heterocyclic group" for R$^9$ and R$^{10}$ and one as a substituent on lower alkyl for R$^9$ and R$^{10}$ may include saturated or unsaturated, monocyclic or polycyclic one containing at least one hetero atom such as nitrogen atom, oxygen atom or sulfur atom, preferably N, O and/or S containing 5 or 6 membered heterocyclic group, in which the most preferable ones are morpholino, pyridyl and thiazolyl.

Suitable "lower alkoxy" and "lower alkoxy" moiety in the term "lower alkoxycarbonyl" may be a straight or branched one such as methoxy, ethoxy, propoxy, isopropoxy, butoxy, isobutoxy, tert-butoxy, pentyloxy, hexyloxy, and the like, in which more preferable one may be C$_1$-C$_4$ alkoxy.

Suitable "heterocyclic group" formed by R$^9$, R$^{10}$ and the attached nitrogen atom may be morpholino, thiomorpholino, its 1-oxide or 1,1-dioxide, pyrrolidin-1-yl, pyrazolidin-1-yl, piperidino, piperazin-1-yl, pyrrolin-1-yl, thiazolidin-3-yl, its 1-oxide or 1,1-dioxide, oxazolidin-3-yl, perhydropyridazin-1-yl, 1,4-dihydropyridin-1-yl, 1,2,3,6-tetrahydropyridin-1-yl, 1,2,3,4-tetrahydroisoquinolin-2-yl, 1,2,3,4-tetrahydroquinolin-1-yl, hexamethyleneimino, 1,4-diazabicyclo[4.3.0]nonan-4-yl, and the like.

Suitable "mono- or di(lower)alkylamino" may be methylamino, ethylamino, propylamino, isopropylamino, butylamino, isobutylamino, dimethylamino, methylethylamino, methylisopropylamino, diethylamino, or the like.

Suitable "lower alkanoyl" may be formyl, acetyl, propionyl, butyryl, isobutyryl, valeryl, isovaleryl, pivaloyl, 4-methylvaleryl, or the like.

Suitable "amino-protected or unprotected amino acid residue" may be glycyl, alanyl, β-alanyl, valyl, leucyl, isoleucyl, histidyl, prolyl, seryl, threonyl, cystyl, phenylalanyl, aspartyl, glutamyl, tryptophyl, or the like, each amino group of which may be protected by N-protective group as mentioned below.

Preferred examples of the above-mentioned acyl group may be lower alkanoyl [e.g. formyl, acetyl, propionyl, butyryl, isobutyryl, valeryl, isovaleryl, pivaloyl, 4-methylvaleryl, etc.], mono- or di(lower)alkylamino(lower)alkanoyl [e.g. methylaminoacetyl, methylaminopropionyl, dimethylaminobutyryl, etc.], lower alkoxy(lower)alkanoyl [e.g. methoxyacetyl, methoxypropionyl, ethoxypropionyl, etc.], aroyl [e.g. benzoyl, toluoyl, etc.], cyclo(lower)alkylcarbonyl [e.g. cyclopropylcarbonyl, cyclobutylcarbonyl, cyclopentylcarbonyl, cyclohexylcarbonyl, etc.], amino-protected or unprotected amino acid residue [e.g. glycyl, benz-oylglycyl, t-butoxycarbonylglycyl, t-butoxycarbonylleucyl, acetylleucyl, t-butoxycarbonylhistidyl, etc.], carbamoyl, mono- or di(lower)alkylcarbamoyl [e.g. methylcarbamoyl, ethylcarbamoyl, propylcarbamoyl, isopropylcarbamoyl, butylcarbamoyl, pentylcarbamoyl, isobutylcarbamoyl, tert-butylcarbamoyl, dimethylcarbamoyl, diethylcarbamoyl, methylethylcarbamoyl, methylisopropylcarbamoyl, methylisobutylcarbamoyl, etc.], heterocyclic(lower) alkylcarbamoyl [e.g. picolylcarbamoyl, pyridylethylcarbamoyl, thiazolylmethylcarbamoyl, morpholinomethylcarbamoyl, morpholinoethylcarbamoyl, etc.], N-heterocyclic(lower)alkyl-N-lower alkylcarbamoyl [e.g. N-picolyl-N-methylcarbamoyl, N-pyridylethyl-N-methylcarbamoyl, N-morpholinomethyl-N-ethylcarbamoyl, N-morpholinoethyl-N-methylcarbamoyl, etc.], ar(lower)alkylcarbamoyl [e.g. benzylcarbamoyl, phenethylcarbamoyl, benzhydrylcarbamoyl, etc.], N-ar(lower)alkyl-N-lower alkylcarbamoyl [e.g. N-benzyl-N-methylcarbamoyl, N-phenethyl-N-methylcarbamoyl, N-phenethyl-N-ethylcarbamoyl, etc.], N-aryl-N-lower alkylcarbamoyl [e.g. N-phenyl-N-methylcarbamoyl, etc.], lower alkoxycarbonyl(lower)alkylcarbamoyl [e.g. methoxycarbonylmethylcarbamoyl, ethoxycarbonylmethylcarbamoyl, ethoxycarbonylethylcarbamoyl, etc.], lower alkoxy(lower)alkylcarbamoyl [e.g. methoxymethylcarbamoyl, methoxyethylcarbamoyl, ethoxypropylcarbamoyl, etc.], aroylcarbamoyl [e.g. benzoylcarbamoyl, toluoylcarbamoyl, etc.], heterocycliccarbamoyl [e.g. pyridylcarbamoyl, morpholinocarbamoyl, thiazolylcarbamoyl, etc.], N-heterocyclic-N-lower alkylcarbamoyl [e.g. N-pyridyl-N-methylcarbamoyl, N-thiazolyl-N-methylcarbamoyl, etc.], heterocycliccarbonyl, preferably N-containing heterocyclic-N-ylcarbonyl which may be substituted with lower alkyl [e.g. morpholinocarbonyl, thiomorpholinocarbonyl, pyperidinocarbonyl, 4-methyl-1-piperazinylcarbonyl, 1,2,3,6-tetrahydro-1-pyridylcarbonyl, etc.], lower alkoxycarbonyl[e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, etc.], mono(or di or tri)halo(lower)alkoxycarbonyl [e.g. iodoethoxycarbonyl, dichloroethoxycarbonyl, trichloroethoxycarbonyl, trifluoromethoxycarbonyl, etc.], hydroxy(lower)alkoxycarbonyl [e.g. hydroxymethoxycarbonyl, hydroxyethoxycarbonyl, hydroxypropoxycarbonyl, hydroxybutoxycarbonyl, etc.], ar(lower)alkoxycarbonyl [e.g. benzyloxycarbonyl, phenethyloxycarbonyl, 4-nitrobenzyloxycarbonyl, trityloxycarbonyl, benzhydryloxycarbonyl, etc.], lower alkenyloxycarbonyl [e.g. vinyloxycarbonyl, allyloxycarbonyl, etc.], lower alkanoyl(lower)alkoxycarbonyl [e.g. acetylmethoxycarbonyl, propionylmethoxycarbonyl, acetylethoxycarbonyl, etc.], lower alkylsulfonyl [e.g. mesyl, ethylsulfonyl, propylsulfonyl, isopropylsulfonyl, butylsulfonyl, isobutylsulfonyl, tert-butylsulfonyl, pentylsulfonyl, hexylsulfonyl, etc.], arylsulfonyl [e.g. pnenylsulfonyl, tosyl, etc.], or the like.

Suitable "lower alkylthio" may be a straight or branched one such as methylthio, ethylthio, propylthio, isopropylthio, butylthio, isobutylthio, tert-butylthio, pentylthio, hexylthio, and the like, in which more preferable one may be $C_1$-$C_4$ alkylthio.

Suitable "heterocyclic group" formed by $R^1$, $R^2$ and the attached nitrogen atom can be referred to the ones formed by $R^9$, $R^{10}$ and the attached nitrogen atom as exemplified above.

Suitable "hydroxy(lower)alkyl" may be hydroxymethyl, hydroxyethyl, hydroxypropyl, hydroxyisopropyl, hydroxybutyl, and the like.

Suitable "lower alkoxy(lower)alkyl" may be methoxymethyl, ethoxymethyl, methoxyethyl, ethoxyethyl, methoxypropyl, and the like.

Suitable "N-protective group" may be substituted or unsubstituted lower alkanoyl [e.g. formyl, acetyl, propionyl, trifluoroacetyl, etc.], phthaloyl, lower alkoxycarbonyl [e.g. tert-butoxycarbonyl, tert-amyloxycarbonyl, etc.], substituted or unsubstituted aralkyloxycarbonyl [e.g. benzyloxycarbonyl, p-nitrobenzyloxycarbonyl, etc.], substituted or unsubstituted arenesulfonyl [e.g. benzenesulfonyl, tosyl, etc.], nitrophenylsulfenyl, aralkyl [e.g. trityl, benzyl, etc.] or the like.

Suitable "lower alkylene" may be a straight or branched one such as methylene, ethylene, trimethylene, tetramethylene, pentamethylene, hexamethylene, propylene, methylmethylene, ethylmethylene, propylmethylene, and the like, in which more preferable one may be $C_1$-$C_4$ alkylene and the most preferable ones are methylene, ethylene, trimethylene, tetramethylene and methylmethylene.

Suitable pharmaceutically acceptable salts of the object compounds [I] are conventional non-toxic salts and include an organic acid addition salt [e.g. formate, acetate, trifluoroacetate, maleate, tartrate, methanesulfonate, benzenesulfonate, toluenesulfonate, etc.], an inorganic acid addition salt [e.g. hydrochloride, hydrobromide, sulfate, phosphate, etc.], a salt with an amino acid [e.g. aspartic acid salt, glutamic acid salt, etc.], or the like.

The processes for preparing the object compounds [I] are explained in detail in the following.

PROCESS 1

Step 1

The compound [IV] or its salt can be prepared by reacting a compound [II] or its reactive derivative at the carboxy group or a salt thereof with a compound [III] or its reactive derivative at the amino group or a salt thereof.

Suitable salts of the compound [IV] can be referred to the ones as exemplified for the compound [I].

Suitable reactive derivative at the carboxy group of the compound [II] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound [II] to be used.

Suitable salts of the compound [II] and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], or the like, and an acid addition salt as exemplified for the compound [I].

Suitable reactive derivative at the amino group of the compound [III] may include Schiff's base type imino or its tautomeric enamine type isomer formed by the reaction of the compound [III] with a carbonyl compound such as aldehyde, ketone or the like; a silyl derivative formed by the reaction of the compound [III] with a silyl compound such as bis(trimethylsilyl)acetamide, mono(trimethylsilyl)acetamide, bis(trimethylsilyl)urea or the like; a derivative formed by reaction of the compound [III] with phosphorus trichloride or phosgene, and the like.

Suitable salts of the compound [III] and its reactive derivative can be referred to the ones as exemplified for the compound [I].

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [II] is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite, ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, oxalyl chloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

Step 2

The compound [V] or its salt can be prepared by subjecting a compound [IV] or its salt to elimination reaction of the N-protective group.

Suitable salts of the compound [V] can be referred to the ones as exemplified for the compound [I].

This reaction is carried out in accordance with a conventional method such as hydrolysis, reduction or the like.

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, hydrazine, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.], an inorganic acid [e.g. hydrochloric acid, hydrobromic acid, sulfuric acid, hydrogen chloride, hydrogen bromide, hydrogen fluoride, etc.] and an acid addition salt compound [e.g. pyridine hydrochloride, etc.].

The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, chloroform, tetrachloromethane, tetrahydrofuran, a mixture thereof or any other solvent which does not adversely influence the reaction. A liquid base or acid can be also used as the solvent. The reaction temperature is not critical and the reaction is usually carried out under cooling to heating.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, plalladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to heating.

Step 3

The object compound [I] or its salt can be prepared by reacting a compound [V] or its reactive derivative at the amino group or a salt thereof with a compound [VI] or its reactive derivative at the carboxy group or a salt thereof, and if necessary, eliminating the N-protective group.

Suitable salts of the compound [VI] can be referred to a base salt as exemplified for the compound [II].

This reaction can be carried out in substantially the same manner as Step 1, and therefore the reaction mode and reaction conditions [e.g. reactive derivatives, condensing agents, solvents, reaction temperature, etc.] of this reaction are to be referred to those as explained in Step 1.

In case that the imidazolyl group of the compound [V] is protected, the object compound [I] can be prepared by further eliminating the N-protective group of the reaction product of the compound [V] with the compound [VI].

This elimination reaction can be carried out in substantially the same manner as Step 2 in this process, and therefore the reaction mode and reaction conditions [e.g. bases, acids, reducing agents, catalysts, solvents, reaction temperature, etc.] of this reaction are to be referred to those as explained in Step 2 in this process.

PROCESS 2

The object compound [Ib] or its salt can be prepared by subjecting a compound [Ia] or its salt to elimination reaction of the N-protective group.

Suitable salts of the compounds [Ia] and [Ib] can be referred to the ones as exemplified for the compound [I].

This elimination reaction can be carried out in substantially the same manner as Step 2 in Process 1, and therefore the reaction mode and reaction conditions [e.g. bases, acids, reducing agents, catalysts, solvents, reaction temperature, etc.] of this reaction are to be referred to those as explained in Step 2 in Process 1.

Among the starting compound [VI], some of them are new and can be prepared by processes as illustrated in the following reaction schemes.

Process A

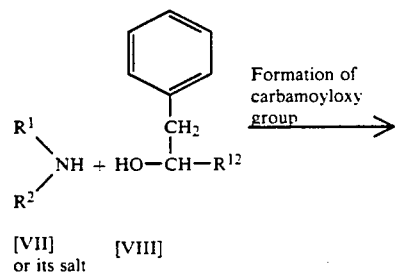

[VII] or its salt   [VIII]

Process B

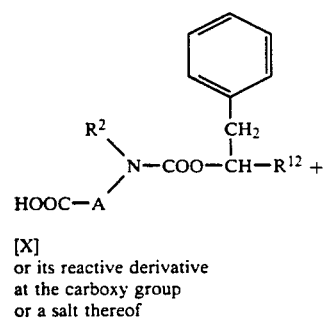

[X] or its reactive derivative at the carboxy group or a salt thereof

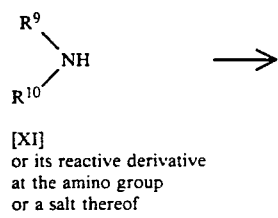

[XI] or its reactive derivative at the amino group or a salt thereof

Process B

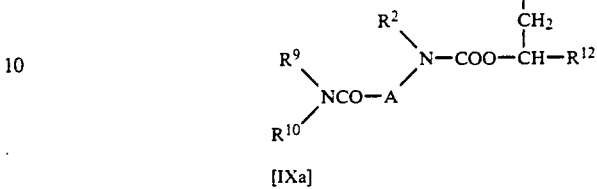

[IXa]

Process C

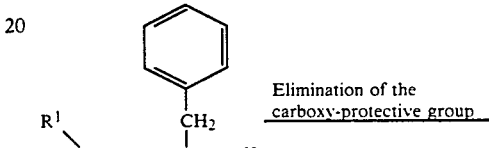

[IX]

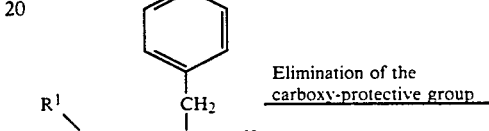

[VI] or its salt wherein
R$^{12}$ is protected carboxy, and
R$^1$, R$^2$, R$^9$, R$^{10}$ and A are each as defined above.

Among the compound [VII], some of them are new and can be prepared by processes as illustrated in the followong reaction schemes.

Process D

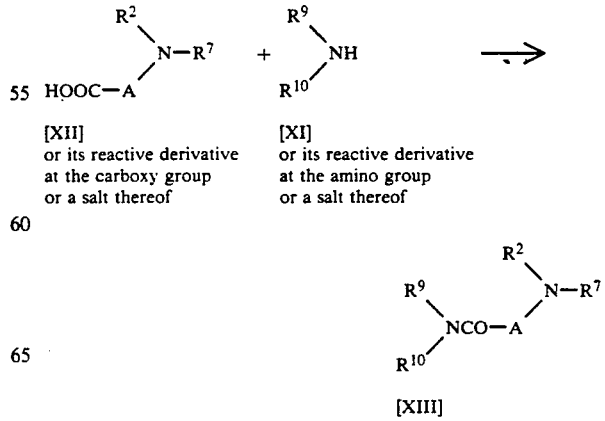

[XII] or its reactive derivative at the carboxy group or a salt thereof

[XI] or its reactive derivative at the amino group or a salt thereof

[XIII]

Process E

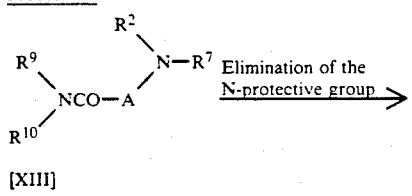

[XIII]

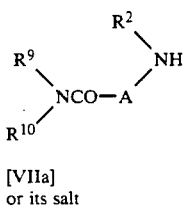

[VIIa]
or its salt

Process F

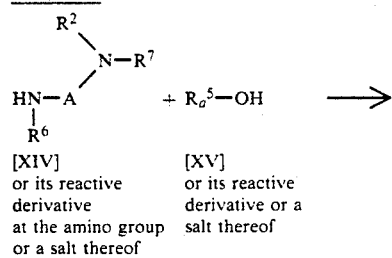

[XIV]         [XV]
or its reactive   or its reactive
derivative      derivative or a
at the amino group  salt thereof
or a salt thereof

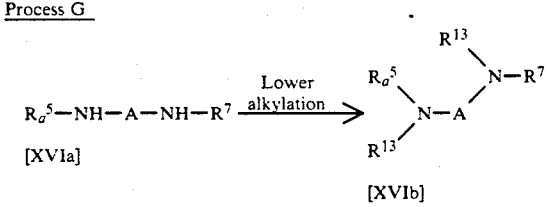

[XVI]

Process G

R_a^5—NH—A—NH—R^7 $\xrightarrow{\text{Lower alkylation}}$

[XVIa]

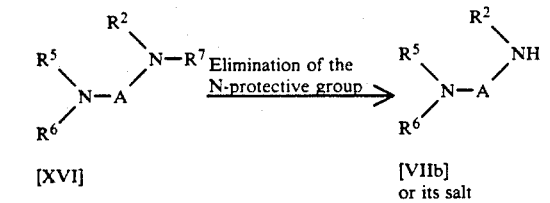

[XVIb]

Process H

[XVI] $\xrightarrow{\text{Elimination of the N-protective group}}$ [VIIb] or its salt wherein
R^5 is acyl,
R^13 is lower alkyl, and
R^2, R^5, R^6, R^7, R^9, R^10 and A are each as defined above.

Suitable "protected carboxy" may be carboxy group protected by conventional protective group such as lower alkoxycarbonyl [e.g. methoxycarbonyl, ethoxycarbonyl, propoxycarbonyl, isopropoxycarbonyl, butoxycarbonyl, sec-butoxycarbonyl, isobutoxycarbonyl, tert-butoxycarbonyl, pentyloxycarbonyl, neopentyloxycarbonyl, hexyloxycarbonyl, etc.], optionally substituted ar(lower)alkoxycarbonyl for example, mono or di or triphenyl(lower)alkoxycarbonyl which may be substituted with nitro [e.g. benzyloxycarbonyl, 4-nitrobenzyloxycarbonyl, benzhydryloxycarbonyl, trityloxycarbonyl, etc.], or the like.

The above-mentioned processes for preparing the starting compounds are explained in detail in the following.

PROCESS A

The compound [IX] can be prepared by subjecting a compound [VII] or its salt and a compound [VIII] to formation reaction of carbamoyloxy group.

Suitable salts of the compound [VII] can be referred to the ones as exemplified for the compound [I].

This reaction is carried out in the presence of reagent which introduces carbonyl group such as phosgene, haloformate compound [e.g. ethyl chloroformate, trichloromethyl chloroformate, etc.], N,N'-carbonyldiimidazole, metal carbonyl compounds [e.g. cobalt carbonyl, manganese carbonyl, etc.], a combination of carbon monoxide and catalysts such as palladium chloride, etc., or the like.

This reaction is usually carried out in a solvent such as dioxane, tetrahydrofuran, benzene, toluene, chloroform, methylene chloride, N,N-dimethylformamide or any other organic solvent which does not adversely influence the reaction.

The reaction temperature is not critical and the reaction is usually carried out under cooling to heating.

PROCESS B

The compound [IXa] can be prepared by reacting a compound [X] or its reactive derivative at the carboxy group or a salt thereof with a compound [XI] or its reactive derivative at the amino group or a salt thereof.

Suitable salts of the compound [X] and its reactive derivative can be referred to the base salts as exemplified for the compound [II].

Suitable salts of the compounds [XI] and its reactive derivative can be referred to the ones as exemplified for the compound [I].

This reaction can be carried out in substantially the same manner as Step 1 in Process 1, and therefore the reaction mode and reaction conditions [e.g. reactive derivatives, condensing agents, solvents, reaction temperature, etc.] of this reaction are to be referred to those as explained in Step 1 in Process 1.

PROCESS C

The compound [VI] or its salt can be prepared by subjecting a compound [IX] to elimination reaction of the carboxy-protective group.

This reaction can be carried out in substantially the same manner as Step 2 in Process 1, and therefore the reaction mode and reaction conditions [e.g. bases, acids, reducing agents, catalysts, solvents, reaction temperature, etc.] of this reaction are to be referred to those as explained in Step 2 in Process 1.

PROCESS D

The compound [XIII] can be prepared by reacting a compound [XII] or its reactive derivative at the carboxy group or a salt thereof with a compound [XI] or its reactive derivative at the amino group or a salt thereof.

Suitable salts of the compound [XII] and its reactive derivative can be referred to the base salts as exemplified for the compound [II].

This reaction can be carried out in substantially the same manner as Step 1 in Process 1, and therefore the reaction mode and reaction conditions [e.g. reactive derivatives, condensing agents, solvents, reaction temperature, etc.] of this reaction are to be referred to those as explained in Step 1 in Process 1.

PROCESS E

The compound [VIIa] or its salt can be prepared by subjecting a compound [XIII] to elimination reaction of the N-protective group.

Suitable salts of the compound [VIIa] can be referred to the ones as exemplified for the compound [I].

This reaction can be carried out in substantially the same manner as Step 2 in Process 1, and therefore the reaction mode and reaction conditions [e.g. bases, acids, reducing agents, catalysts, solvents, reaction temperature, etc.] of this reaction are to be referred to those as explained in Step 2 in Process 1.

PROCESS F

The compound [XVI] can be prepared by reacting a compound [XIV] or its reactive derivative at the amino group or a salt thereof with a compound [XV] or its reactive derivative or a salt thereof.

Suitable salts of the compound [XIV] and its reactive derivative can be referred to the ones as exemplfied for the compound [I].

Suitable salts of the compound [XV] and its reactive derivative can be referred to the base salts as exemplified for the compound [II].

This reaction can be carried out in substantially the same manner as Step 1 in Process 1, and therefore the reaction mode and reaction conditions [e.g. reactive derivatives, condensing agents, solvents, reaction temperature, etc.] of this reaction are to be referred to those as explained in Step 1 in Process 1.

PROCESS G

The compound [XVIb] or its salt can be prepared by subjecting a compound [XVIa] or its salt to lower alkylation reaction.

Suitable lower alkylating agents to be used in this reaction may be lower alkyl halide [e.g. methyl iodide, ethyl iodide, propyl iodide, butyl iodide, butyl chloride, pentyl chloride, etc.], or the like.

This reaction is usually carried out in the presence of a base such as an alkali metal [e.g. sodium, potassium, etc.], an alkaline earth metal [e.g. magnesium, calcium, etc.], the hydride or hydroxide thereof, alkali metal alkoxide [e.g. sodium methoxide, sodium ethoxide, potassium tert-butoxide, etc.], or the like.

This reaction is usually carried out in a conventional solvent such as water, alcohol [e.g. methanol, ethanol, propanol, etc.], tetrahydrofuran, dioxane, ethyl acetate, methylene chloride, N,N-dimethylformamide, dimethyl sulfoxide, diethyl ether or any other organic solvent which does not adversely influence the reaction. And in case that the above-mentioned lower alkylating agent is in liquid, it can be also used as a solvent.

The reaction temperature is not critical, and the reaction is usually carried out under cooling, at ambient temperature or under warming or heating.

PROCESS H

The compound [VIIb] or its salt can be prepared by subjecting a compound [XVI] to elimination reaction of the N-protective group.

Suitable salts of the compound [VIIb] can be referred to the ones as exemplified for the compound [I].

This reaction can be carried out in substantially the same manner as Step 2 in Process 1, and therefore the reaction mode and reaction conditions [e.g. bases, acids, reducing agents, catalysts, solvents, reaction temperature, etc.] of this reaction are to be referred to those as explained in Step 2 in Process 1.

The compounds obtained by the above processes can be isolated and purified by a conventional method such as pulverization, recrystallization, column chromatography, reprecipitation, or the like.

It is to be noted that the compound [I] and the other compounds may include one or more stereoisomers due to asymmetric carbon atoms, and all of such isomers and mixture thereof are included within the scope of this invention.

The object compounds [I] and pharmaceutically acceptable salts thereof possess strong inhibitory activities against renin, and useful as a hypotensor and a therapeutic agent on heart failure, especially for oral administration.

For therapeutic purpose, the compounds [I] and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compounds [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating hypertension and heart failure. In general, amounts between 0.1 mg/body and about 1,000 mg/body may be administered per day.

In order to illustrate the usefulness of the object compound [I], the pharmacological test data of some representative compounds of the compound [I] are shown in the following.

TEST COMPOUNDS (1) 2(S)-[$N^\alpha$-(2(S)-Morpholinocarbonyloxy-3-phenylpropionyl)-L-histidyl]amino-1-cyclohexyl-3(S)-hydroxy-6-methylheptane (2) 2(S)-[$N^\alpha$-(2(S)-Morpholinocarbonyloxy-3-phenylpropionyl)-$N^\alpha$-methyl-L-histidyl]amino-1-cyclohexyl-3(S)-hydroxy-6-methylheptane (3) 2(S)-[$N^\alpha$-{2(S)-(N-Methoxycarbonylmethyl-N-methylaminocarbonyloxy)-3-phenylpropionyl}-$N^\alpha$-methyl-L-histidyl]amino-1-cyclohexyl-3(S)-hydroxy-6-methylheptane (4) 2(S)-[$N^\alpha$-{2(S)-(2(R)-Methoxycarbonylpyrrolidine-1-carbonyloxy)-3-phenylpropionyl}-$N^\alpha$-methyl-L-histidyl]amino-1-cyclohexyl-3(S)-hydroxy-6-methylheptane (5) 2(S)-[N$^\alpha$-[2(S)-{N-(2-Morpholinocarbonylethyl)-N-methylaminocarbonyloxy}-3-phenylpropionyl]-N$^\alpha$-methyl-L-histidyl]amino-1-cyclohexyl-3(S)-hydroxy-6-methylheptane (6) 2(S)-[N$^\alpha$-[2(S)-{N-(2-Dimethylaminocarbonylethyl)-N-methylaminocarbonyloxy}-3-phenylpropionyl]-N$^\alpha$-methyl-L-histidyl]amino-1-cyclohexyl-3(S)-hydroxy-6-methylheptane (7) 2(S)-[N$^\alpha$-[2(S)-{N-(Dimethylaminocarbonylmethyl)-N-methylaminocarbonyloxy}-3-phenylpropionyl]-N$^\alpha$-methyl-L-histidyl]amino-1-cyclohexyl-3(S)-hydroxy-6-methylheptane (8) 2(S)-[N$^\alpha$-[(2(S)-{N-(4-Picolylaminocarbonylmethyl)-N-methylaminocarbonyloxy}-3-phenylpropionyl]-N$^\alpha$-methyl-L-histidyl]amino-1-cyclohexyl-3(S)-hydroxy-6-methylheptane (9) 2(S)-[N$^\alpha$-{2(S)-(2(R)-Dimethylaminocarbonylpyrrolidine-1-carbonyloxy)-3-phenylpropionyl}-N$^\alpha$-methyl-L-histidyl]-amino-1-cyclohexyl-3(S)-hydroxy-6-methylheptane

(10) 2(S)-[N$^\alpha$-{2(S)-(6(S)-2-Oxo-1,4-diazabicyclo[4.3.0]nonane-4-carbonyloxy)-3-phenylpropionyl}-N$^\alpha$-methyl-L-histidyl]amino-1-cyclohexyl-3(S)-hydroxy-6-methylheptane

(11) 2(S)-[N$^\alpha$-{2(S)-(4-Methyl-3-oxopiperazine-1-carbonyloxy)-3-phenylpropionyl}-N$^\alpha$-methyl-L-histidyl]-amino-1-cyclohexyl-3(S)-hydroxy-6-methylheptane

(12) 2(S)-[N$^\alpha$-{2(S)-3-Oxopiperazine-1-carbonyloxy)-3-phenylpropionyl}-N$^\alpha$-methyl-L-histidyl]amino-1-cyclohexyl-3(S)-hydroxy-6-methylheptane

(13) 2(S)-[N$^\alpha$-{2(S)-(N-Isobutoxycarbonylmethyl-N-methylaminocarbonyloxy)-3-phenylpropionyl}-N$^\alpha$-methyl-L-histidyl]amino-1-cyclohexyl-3(S)-hydroxy-6-methylheptane

(14) 2(S)-[N$^\alpha$-{2(S)-(N-Methyl-N-phenethyloxycarbonylmethylaminocarbonyloxy)-3-phenylpropionyl}-N$^\alpha$-methyl-L-histidyl]amino-1-cyclohexyl-3(S)-hydroxy-6-methylheptane

(15) 2(S)-[N$^\alpha$-[2(S)-{N-Methyl-N-(2-oxopropoxycarbonylmethyl)aminocarbonyloxy}-3-phenylpropionyl]-N$^\alpha$-methyl-L-histidyl]amino-1-cyclohexyl-3(S)-hydroxy-6-methylheptane

(16) 2(S)-[N$^\alpha$-[2(S)-[N-{2-(Ethoxycarbonylmethylaminocarbonyl)ethyl}-N-methylaminocarbonyloxy]-3-phenylpropionyl]-N$^\alpha$-methyl-L-histidyl]amino-1-cyclohexyl-3(S)-hydroxy-6-methylheptane

(17) 2(S)-[N$^\alpha$-[2(S)-[N-{2-(2-Picolylaminocarbonyl)ethyl}-N-methylaminocarbonyloxy]-3-phenylpropionyl]-N$^\alpha$-methyl-L-histidyl]amino-1-cyclohexyl-3(S)-hydroxy-6-methylheptane

(18) 2(S)-[N$^\alpha$-[2(S)-{N-(2-Thiomorpholinocarbonylethyl)-N-methylaminocarbonyloxy}-3-phenylpropionyl]-N$^\alpha$-methyl-L-histidyl]amino-1-cyclohexyl-3(S)-hydroxy-6-methylheptane

(19) 2(S)-[N$^\alpha$-[2(S)-{N-(2-Morpholinocarbonylethyl)-N-methylaminocarbonyloxy}-3-phenylpropionyl]-L-histidyl]amino-1-cyclohexyl-3(S)-hydroxy-6-methylheptane

(20) 2(S)-[N$^\alpha$-{2(S)-(N'-Isobutoxycarbonyl-N,N'-dimethylhydrazinocarbonyloxy)-3-phenylpropionyl}-N$^\alpha$-methyl-L-histidyl]amino-1-cyclohexyl-3(S)-hydroxy-6-methylheptane

(21) 2(S)-[N$^\alpha$-[2(S)-.{N'-(Isopropylcarbamoyl)-N,N'-dimethylhydrazinocarbonyloxy}-3-phenylpropionyl]-N$^\alpha$-methyl-L-histidyl]amino-1-cyclohexyl-3(S)-hydroxy-6-methylheptane

(22) 2(S)-[N$^\alpha$-{2(S)-(2-Isopropylcarbamoylpyrazolidine-1-carbonyloxy)-3-phenylpropionyl}-N$^\alpha$-methyl-L-histidyl]amino-1-cyclohexyl-3(S)-hydroxy-6-methylheptane

(23) 2(S)-[N$^\alpha$-[2(S)-[N-Methyl-N-[2-{N-(morpholinocarbonyl)-N-methylamino}ethyl]aminocarbonyloxy]-3-phenylpropionyl]-N$^\alpha$-methyl-L-histidyl]amino-1-cyclohexyl-3(S)-hydroxy-6-methylheptane

(24) 2(S)-[N$^\alpha$-[2(S)-[N-Methyl-N-{2-(N-isobutyryl-Nmethylamino)ethyl}aminocarbonyloxy]-3-phenylpropionyl]-N$^\alpha$-methyl-L-histidyl]amino-1-cyclohexyl-3(S)-hydroxy-6-methylheptane

(25) 2(S)-[N$^\alpha$-[2(S)-[N-Methyl-N-{2-(N-isovaleryl-N-methylamino)ethyl}aminocarbonyloxy]-3-phenylpropionyl]-N$^\alpha$-methyl-L-histidyl]amino-1-cyclohexyl-3(S)-hydroxy-6-methylheptane

(26) 2(S)-[N$^\alpha$-[2(S)-[N-{2-(N-Methyl-N-phenylcarbamoyl)ethyl}-N-methylaminocarbonyloxy]-3-phenylpropionyl]-N$^\alpha$-methyl-L-histidyl]amino-1-cyclohexyl-3(S)-hydroxy-6-methylheptane

(27) 2(S)-[N$^\alpha$-[2(S)-[N-{2-(N-Methyl-N-isobutylcarbamoyl)ethyl}-N-methylaminocarbonyloxy]-3-phenylpropionyl]-N$^\alpha$-methyl-L-histidyl]amino-1-cyclohexyl-3(S)-hydroxy-6-methylheptane

(28) 2(S)-[N$^\alpha$-{2(S)-(3-Oxopiperidinocarbonyloxy)-3-phenylpropionyl}-N$^\alpha$-methyl-L-histidyl]amino-1-cyclohexyl-3(S)-hydroxy-6-methylheptane

(29) 2(S)-[N$^\alpha$-[2(S)-[N-{4-(N-Methyl-N-isopropylcarbamoyl)butyl}-N-methylaminocarbonyloxy]-3-phenylpropionyl]-N$^\alpha$-methyl-L-histidyl]amino-1-cyclohexyl-3(S)-hydroxy-6-methylheptane

(30) 2(S)-[N$^\alpha$-[2(S)-{N-(4-Isopropylcarbamoylbutyl)-N-methylaminocarbonyloxy}-3-phenylpropionyl]-N$^\alpha$-methyl-L-histidyl]amino-1-cyclohexyl-3(S)-hydroxy-6-methylheptane

(31) 2(S)-[N$^\alpha$-[2(S)-[N-Methyl-N-[3-{N-(morpholinocarbonyl)-N-methylamino}propyl]aminocarbonyloxy]-3-phenylpropionyl]-N$^\alpha$-methyl-L-histidyl]amino-1-cyclohexyl-3(S)-hydroxy-6-methylheptane

(32) 2(S)-[N$^\alpha$-[2(S)-{N-Methyl-N-(3-morpholinocarbonylpropyl)aminocarbonyloxy}-3-phenylpropionyl]-N$^\alpha$-methyl-L-histidyl]amino-1-cyclohexyl-3(S)-hydroxy-6-methylheptane

(33) 2(S)-[N$^\alpha$-[2(S)-[N-Methyl-N-{3-(N-isopropyl-N-methylcarbamoyl)propyl}aminocarbonyloxy]-3-phenylpropionyl]-N$^\alpha$-methyl-L-histidyl]amino-1-cyclohexyl-3(S)-hydroxy-6-methylheptane

(34) 2(S)-[N$^\alpha$-[2(S)-[N-Methyl-N-[4-{N-(morpholinocarbonyl)-N-methylamino}butyl]aminocarbonyloxy]-3-phenylpropionyl]-N$^\alpha$-methyl-L-histidyl]amino-1-cyclohexyl-3(S)-hydroxy-6-methylheptane

(35) 2(S)-[N$^\alpha$-[2(S)-{N-(4-Morpholinocarbonylbutyl)-N-methylaminocarbonyloxy}-3-phenylpropionyl]-N$^\alpha$-methyl-L-histidyl]amino-1-cyclohexyl-3(S)-hydroxy-6-methylheptane

(36) 2(S)-[N$^\alpha$-[2(S)-{N'-(Morpholinocarbonyl)-N,N'-dimethylhydrazinocarbonyloxy}-3-phenylpropionyl]-L-histidyl]amino-1-cyclohexyl-3(S)-hydroxy-6-methylheptane

(37) 2(S)-[N$^\alpha$-[2(S)-[N-[2-N-{2-(2-Pyridyl)ethyl}-N-methylaminocarbonyl]ethyl]-N-methylaminocarbonyloxy]-3-phenylpropionyl]-N$^\alpha$-methyl-L-histidyl]amino-1-cyclohexyl-3(S)-hydroxy-6-methylheptane

(38) 2(S)-[N$^\alpha$-[2(S)-[N-{2-(1,2,3,6-Tetrahydropyridine-1-carbonyl)ethyl}-N-methylaminocarbonyloxy]-3-phenylpropionyl]-N$^\alpha$-methyl-L-histidyl]amino-1-cyclohexyl-3(S)-hydroxy-6-methylheptane

(39) 2(S)-[N$^\alpha$-[2(S)-{N-(2-Isopropylaminocarbonylethyl)-N-methylaminocarbonyloxy}-3-phenylpropionyl]-N$^\alpha$-methyl-L-histidyl]amino-1-cyclohexyl-3(S)-hydroxy-6-methylheptane

(40) 2(S)-8 N$^\alpha$-[2(S)-{N-(2-Isopropylsulfonylethyl)-N-methylaminocarbonyloxy}-3-phenylpropionyl]-N$^\alpha$-methyl-L-histidyl]amino-1-cyclohexyl-3(S)-hydroxy-6-methylheptane

TEST 1

Test Method

Human plasma was collected from male volunteers pretreated with no drugs and used as a pool. Disodium salt of ethylenediaminetetraacetic acid (EDTA) was used as the anticoagulant. Plasma renin activity was measured as the rate of angiotensin I (Ang I) formation after incubation (37° C.) of the endogenous renin and angiotensinogen in plasma at pH 6.0. The incubation mixture contained 250 μl of plasma, 5 μl of (phenylmethyl)sulfonyl fluoride, 30 μl of buffer (sodium, potassium-phosphate, pH 6.0), and 15 μl of an appropriate concentration of test compound in 50% ethyl alcohol-water vehicle. The Ang I formed after 90 minutes of incubation was measured by radioimmunoassay (RIA) which was carried out with a commercial kit, RENCTK 100 (manufactured by Commissariat A L'energic Atomique). Samples were incubated in duplicate and each tube was measured in duplicate in the RIA. Percentage inhibition of plasma renin activity was calculated by comparing the amount of Ang I produced with and without a test compound. The concentration of test compound that inhibited plasma renin activity by 50% (IC$_{50}$) was determined by Probit method.

| Test Results | |
|---|---|
| Test Compound | IC$_{50}$ (M) |
| (1) | 1.9 × 10$^{-8}$ |
| (2) | 8.0 × 10$^{-8}$ |
| (3) | 3.3 × 10$^{-8}$ |
| (4) | 1.3 × 10$^{-8}$ |
| (5) | 2.5 × 10$^{-8}$ |
| (6) | 4.1 × 10$^{-8}$ |
| (7) | 4.0 × 10$^{-8}$ |
| (8) | 4.6 × 10$^{-8}$ |
| (9) | 3.0 × 10$^{-8}$ |
| (10) | 2.1 × 10$^{-8}$ |
| (11) | 1.9 × 10$^{-8}$ |
| (12) | 2.9 × 10$^{-8}$ |
| (13) | 3.4 × 10$^{-8}$ |
| (14) | 4.8 × 10$^{-8}$ |
| (15) | 3.3 × 10$^{-8}$ |
| (16) | 3.8 × 10$^{-8}$ |
| (17) | 3.3 × 10$^{-8}$ |
| (18) | 3.0 × 10$^{-8}$ |
| (19) | 4.8 × 10$^{-9}$ |
| (20) | 7.0 × 10$^{-8}$ |
| (21) | 4.3 × 10$^{-8}$ |
| (22) | 6.3 × 10$^{-8}$ |
| (23) | 4.0 × 10$^{-9}$ |
| (24) | 8.7 × 10$^{-9}$ |
| (25) | 1.4 × 10$^{-8}$ |
| (26) | 2.4 × 10$^{-8}$ |
| (27) | 4.6 × 10$^{-8}$ |
| (28) | 4.4 × 10$^{-8}$ |
| (29) | 1.6 × 10$^{-8}$ |
| (30) | 6.4 × 10$^{-9}$ |
| (31) | 1.3 × 10$^{-8}$ |
| (32) | 1.5 × 10$^{-8}$ |
| (33) | 1.7 × 10$^{-8}$ |
| (34) | 7.5 × 10$^{-9}$ |
| (35) | 5.3 × 10$^{-9}$ |
| (36) | 9.8 × 10$^{-9}$ |
| (37) | 3.8 × 10$^{-8}$ |
| (38) | 4.4 × 10$^{-8}$ |

-continued

| Test Results | |
|---|---|
| Test Compound | IC$_{50}$ (M) |
| (39) | 3.7 × 10$^{-8}$ |
| (40) | 5.7 × 10$^{-8}$ |

TEST 2

Test Method

Male or female cynomolgus monkeys (*Macaca fascicularis*) weighing about 2.5-3.5 kg were used. Sodium depletion was achieved by administering furosemide, 15 mg/kg subcutaneously one day before and then 10 mg/kg intravenously 30 minutes before the administration of the test compound.

Test compounds were dissolved in diluted equimolar hydrochloric acid (pH 5-6) and orally administered to conscious and trained monkeys placed in restraining chairs with pneumatic cuff positioned around the arm for oscillometric measurement of mean arterial blood pressure (MAP) (Model BP-203 NPJ, manufactured by Nippon Colin).

The MAP was measured at 0 (predosing base line), 0.5, 1, 2, 3, 4 and 6 hours after administration of the test compound. The maximum hypotensive effect was calculated as the maximum percentage fall of MAP from the pretreatment value.

Blood samples were collected at 0, 0.5, 1, 2, 4 and 6 hours after dosing from the antecubital vein of the monkey into disodium salt of EDTA coated tubes, centrifuged for 10 min. (3000 rpm, 4° C.) and plasma was obtained for determination of plasma renin activity (PRA). PRA was measured as the rate of Ang I formation with the same principle as illustrated in Test 1. 100 μl of sample plasma was mixed with 100 μl of the solution of angiotensinase inhibitors (3 mM 8-hydroxyquinoline sulfate and 5 mM 2,3-dimercaptopropanol, SB-REN-1, SORIN BIOMEDICA, Italy). Half (100 μl) of the mixture was incubated at 37° C. for one hour and Ang I formed was determined by a commercial RIA kit (DINABOTT). The remaining half (100 μl) of the reaction mixture was kept at 4° C. for one hour to measure and correct for the preexisting Ang I in the plasma. Percentage inhibition of PRA was calculated by the following formula:

$$\text{Inhibition } (\%) = \left(1 - \frac{D_{37} - D_4}{A_{37} - A_4}\right) \times 100$$

A$_{37}$: the amount of angiotensin I formed by incubation at 37° C. of plasma collected before dosing the test compound A$_4$: the amount of angiotensin I formed by keeping at 4° C. of plasma collected before dosing the test compound D$_{37}$: the amount of angiotensin I formed by incubation at 37° C. of plasma collected after dosing the test compound D$_4$: the amount of angiotensin I formed by keeping at 4° C. of plasma collected after dosing the test compound.

| Test Compound | Test Results Dose [mg/kg(po)] | Maximum hypotensive effect (%) | Maximum inhibition of PRA (%) |
|---|---|---|---|
| (5) | 32 | 18 | 92 |
| (23) | 3.2 | 19 | 99 |
| (24) | 3.2 | 15 | 93 |

The following Preparations and Examples are given for the purpose of illustrating preferable preparations of the object compounds [I], and preparations of said compounds are not limited to the following Preparations and Examples.

In the following Preparations and Examples, Kieselgel 60F 254 (Trademark: manufactured by Merck & Co.) (thikness: 0.25 mm) was used as TLC plate.

PREPARATION 1

To a mixture of N-t-butoxycarbonyl-N-methyl-β-alanine (1.02 g) and morpholine (0.48 g) in dry methylene chloride was added N-ethyl-N'-(3-dimethylaminopropyl)carbodiimide hydrochloride (1.05 g), and the mixture was stirred at ambient temperature overnight. After evaporation of the solvent, the residue was dissolved in ethyl acetate. The solution was washed with 1% citric acid aqueous solution, saturated sodium bicarbonate solution, and saturated sodium chloride solution. Then the solution was dried over magnesium sulfate and concentrated under reduced pressure to give 4-(N-t-butoxycarbonyl-N-methyl-β-alanyl)morpholine (1.36 g).

Rf: 0.57 (methanol/chloroform, 10%, V/V).

PREPARATION 2

A solution of 4-(N-t-butoxycarbonyl-N-methyl-β-alanyl)morpholine (1.37 g) in trifluoroacetic acid (20 ml) was stirred at 0° C. for 1 hour. The solvent was evaporated to give 4-(N-methyl-β-alanyl)morpholine trifluoroacetic acid salt (1.44 g).

Rf: 0.17 (chloroform:methanol:acetic acid, 8:1:1, V/V).

PREPARATION 3

The following compounds were obtained according to a similar manner to that of Preparation 1.

(1) 4-(N-t-Butoxycarbonyl-N-methyl-β-alanyl)thiomorpholine (798 mg) was obtained from N-t-butoxycarbonyl-N-methyl-β-alanine (610 mg) and thiomorpholine (372 mg).

Rf: 0.79 (chloroform:methanol, 9:1, V/V).

(2) 2-[(N-t-Butoxycarbonyl-N-methyl-β-alanyl)amino]thiazole (639 mg) was obtained from N-t-butoxycarbonyl-N-methyl-β-alanine (610 mg) and 2-aminothiazole (361 mg).

Rf: 0.63 (chloroform:methanol, 9:1, V/V).

(3) 2-[(N-t-Butoxycarbonyl-N-methyl-β-alanyl)aminomethyl]pyridine (902 mg) was obtained from N-t-butoxycarbonyl-N-methyl-β-alanine (610 mg) and 2-picolylamine (389 mg).

Rf: 0.55 (chloroform:methanol, 9:1, V/V).

(4) 4-[2-(N-t-Butoxycarbonyl-N-methyl-β-alanyl)aminoethyl]morpholine (931 mg) was obtained from N-t-butoxycarbonyl-N-methyl-β-alanine (610 mg) and 4-(2-aminoethyl)morpholine (469 mg).

Rf: 0.53 (chloroform:methanol, 9:1, V/V).

(5) 2-[2-{N-(N-t-Butoxycarbonyl-N-methyl-β-alanyl)-Nmethylamino}ethyl]pyridine (1.08 g) was obtained from N-t-butoxycarbonyl-N-methyl-β-alanine (711 mg) and 2-(2-methylaminoethyl)pyridine (572 mg).

Rf: 0.61 (chloroform:methanol, 9:1, V/V).

(6) 1-(N-t-Butoxycarbonyl-N-methyl-β-alanyl)-4-methylpiperazine (460 mg) was obtained from N-t-butoxycarbonyl-N-methyl-β-alanine (711 mg) and 4-methylpiperazine (421 mg).

Rf: 0.45 (chloroform:methanol, 9:1, V/V).

(7) 2-[N-(N-t-Butoxycarbonyl-N-methyl-β-alanyl)-N-methylamino]pyridine (324.3 mg) was obtained from N-t-butoxycarbonyl-N-methyl-β-alanine (508 mg) and 2-(methylamino)pyridine (325 mg).

Rf: 0.63 (chloroform:methanol, 9:1, V/V).

(8) 3-[(N-t-Butoxycarbonyl-N-methyl-β-alanyl)aminomethyl]pyridine (1.03 g) was obtained from N-t-butoxycarbonyl-N-methyl-β-alanine (711 mg) and 3-picolylamine (454 mg).

Rf: 0.43 (chloroform:methanol, 9:1, V/V).

(9) 1-(N-t-Butoxycarbonyl-N-methyl-β-alanyl)-1,2,3,6-tetrahydropyridine (645 mg) was obtained from N-t-butoxycarbonyl-N-methyl-β-alanine (813 mg) and 1,2,3,6-tetrahydropyridine (399 mg).

Rf: 0.68 (chloroform:methanol, 9:1, V/V).

(10) N-Isopropyl-N$^\alpha$-t-butoxycarbonyl-N$^\alpha$-methyl-β-alaninamide (893 mg) was obtained from N-t-butoxycarbonyl-N-methyl-β-alanine (813 mg) and isopropylamine (284 mg).

Rf: 0.62 (chloroform:methanol, 9:1, V/V).

(11) (N-t-Butoxycarbonyl-N-methyl-β-alanyl)glycine ethyl ester (830 mg) was obtained from N-t-butoxycarbonyl-N-methyl-β-alanine (600 mg) and glycine ethyl ester hydrochloride (495 mg).

Rf: 0.50 (ethyl acetate).

(12) N,N-Dimethyl-N$^\alpha$-t-butoxycarbonyl-N$^\alpha$-methyl-β-alaninamide (1.15 g) was obtained from N-t-butoxycarbonyl-N-methyl-β-alanine (1.02 g) and dimethylamine hydrochloride (0.45 g).

Rf: 0.50 (methanol/chloroform, 10%, V/V).

(13) 4-(N-t-Butoxycarbonylsarcosyl)morpholine (386 mg) was obtained from N-t-butoxycarbonylsarcosine (284 mg) and morpholine (144 mg)

Rf: 0.66 (methanol/chloroform, 10%, V/V).

(14) 4-(N-t-Butoxycarbonyl-N-methyl-D-alanyl)morpholine (738.4 mg) was obtained from N-t-butoxycarbonyl-N-methyl-D-alanine (610 mg) and morpholine (290 mg).

Rf: 0.41 (ethyl acetate:n-hexane, 3:1, V/V).

(15) 2-[N-(N-t-Butoxycarbonylsarcosyl)-N-methylamino]ethylbenzene (897.4 mg) was obtained from N-t-butoxycarbonylsarcosine (568 mg) and N-methyl-N-phenethylamine (446 mg).

Rf: 0.47 (ethyl acetate:n-hexane, 3:1, V/V).

(16) N,N-Dimethyl-N$^\alpha$-t-butoxycarbonylsarcosinamide (1.08 g) was obtained from N-t-butoxycarbonylsarcosine (0.95 g) and dimethylamine hydrochloride (0.45 g).

Rf: 0.41 (methanol/chloroform, 10%, V/V).

(17) N-n-Butyl-N$^\alpha$-t-butoxycarbonylsarcosinamide (581 mg) was obtained from N-t-butoxycarbonylsarcosine (473 mg) and n-butylamine (201 mg).

Rf: 0.50 (ethyl acetate:benzene:acetic acid, 20:20:1, V/V).

(18) 4-[(N-t-Butoxycarbonylsarcosyl)aminomethyl]pyridine (595.3 mg) was obtained from N-t-butoxycarbonylsarcosine (473 mg) and 4-picolylamine (297 mg). mp: 115°–116° C.

Rf: 0.50 (methanol:chloroform, 1:6, V/V).

(19) N,N-Dimethyl-N$^\alpha$-t-butoxycarbonyl-D-prolinamide (559.1 mg) was obtained from N-t-butoxycarbonyl-D-proline (455 mg) and dimethylamine hydrochloride (180 mg).

Rf: 0.27 (ethyl acetate:benzene:acetic acid, 20:20:1, V/V).

t-Butoxycarbonyl groups of the compounds obtained in this Preparation were eliminated according to a similar manner to that of Preparation 2, and thus obtained trifluoroacetic acid salt compounds were used as starting compounds in Preparation 33.

PREPARATION 4

(1) To a solution of N-t-butoxycarbonylsarcosinal (1.50 g) and glycine methyl ester hydrochloride (1.63 g) in methanol (60 ml) was added a solution of sodium cyanoborohydride (544 mg) in methanol (10 ml) at ambient temperature. The mixture was stirred overnight at the same temperature. After evaporation of the solvent, the residue was dissolved in ethyl acetate (50 ml), and the solution was washed with 1M sodium bicarbonate solution and water successively, dried over magnesium sulfate, and concentrated under reduced pressure. The residue was purified with silica gel column chromatography (chloroform as eluent) to give N-[2-(N-t-butoxycarbonyl-N-methylamino)ethyl]glycine methyl ester (1.04 g) as an oil.

Rf: 0.69 (chloroform:methanol:acetic acid, 8:1:1, V/V).

(2) A solution of N-[2-(N-t-butoxycarbonyl-N-methylamino)ethyl]glycine methyl ester (1.06 g) in trifluoroacetic acid (15 ml) was stirred at 0° C. for 1 hour. After evaporation of the solvent in vacuo, the residue was dissolved in 6N ammonia in methanol (20 ml). The solution was stirred at ambient temperature for 30 minutes, and concentrated in vacuo to give 1-methyl-2-piperazinone (490 mg) as an oil.

Rf: 0.28 (chloroform:methanol, 10:1, V/V).

PREPARATION 5

(1) N-(N-t-Butoxycarbonyl-2(S)-pyrrolidinylmethyl)glycine methyl ester (808 mg) was obtained according to a similar manner to that of Preparation 4-(1) from N-t-butoxycarbonylprolinal (1.99 g) and glycine methyl ester hydrochloride (1.88 g).

Rf: 0.31 (ethyl acetate).

(2) 6(S)-2-Oxo-1,4-diazabicyclo[4.3.0]nonane (410 mg) was obtained according to a similar manner to that of Preparation 4-(2) from N-(N-t-butoxycarbonyl-2(S)-pyrrolidinylmethyl)glycine methyl ester (800 mg).

Rf: 0.52 (chloroform:methanol:acetic acid, 8:1:1, V/V).

PREPARATION 6

To a solution of N,N'-dimethylhydrazine dihydrochloride (940 mg) and triethylamine (2.15 g) in methylene chloride (30 ml) which was cooled to 0° C., was added isobutyl chloroformate (970 mg). The mixture was stirred at 0° C. for 1 hour. After evaporation of the solvent, the residue was dissolved in ethyl acetate (50 ml) and the solution was washed with 1M sodium bicarbonate solution and water successively, and dried over sodium sulfate. The solvent was evaporated to give N-isobutoxycarbonyl-N,N'-dimethylhydrazine (922 mg) as an oil.

Rf: 0.78 (chloroform:methanol, 10:1, V/V).

PREPARATION 7

The following compounds were obtained according to a similar manner to that of Preparation 6.

(1) N-(Morpholinocarbonyl)-N,N'-dimethylhydrazine (1.70 g) was obtained from N,N'-dimethylhydrazine dihydrochloride (1.33 g) and morpholinocarbonyl chloride (1.50 g).

Rf: 0.52 (chloroform:methanol, 10:1, V/V).

(2) N-Benzyloxycarbonyl-N,N'-dimethylhydrazine (4.78 g) was obtained N,N'-dimethylhydrazine dihydrochloride (4.00 g) and benzyloxycarbonyl chloride (4.8 ml).

Rf: 0.56 (chloroform:methanol, 10:1, V/V).

(3) 1-Benzyloxycarbonylpyrazolidine (8.26 g) was obtained from pyrazolidine dihydrochloride (5.81 g) and benzyloxycarbonyl chloride (6.624 g).

Rf: 0.61 (chloroform:methanol, 9:1, V/V).

(4) 1-Benzyloxycarbonylperhydropyridazine (9.20 g) from perhydropyridazine dihydrochloride (6.68 g) and benzyloxycarbonyl chloride (7.123 g).

Rf: 0.29 (n-hexane:ethyl acetate, 1:1, V/V).

PREPARATION 8

To a solution of N,N'-dimethylhydrazine dihydrochloride (1.33 g) and triethylamine (2.02 g) in dry tetrahydrofuran (20 ml) which was cooled to 0° C., was added isopropyl isocyanate (851 mg). The mixture was stirred at 0° C. for 2 hours. After evaporation of the solvent, the residue was dissolved in ethyl acetate (50 ml). The solution was washed with 1M sodium bicarbonate solution and water successively, and dried over magnesium sulfate. The solvent was evaporated to give N-(isopropylcarbamoyl)-N,N'-dimethylhydrazine (771 mg) as an oil.

Rf: 0.48 (chloroform:methanol, 10:1, V/V).

PREPARATION 9

N-(Benzylcarbamoyl)-N,N'-dimethylhydrazine (1.07 g) was obtained according to a similar manner to that of Preparation 8 from N,N'-dimethylhydrazine dihydrochloride (1.33 g) and benzyl isocyanate (1.33 g).

Rf: 0.47 (chloroform:methanol, 10:1, V/V).

PREPARATION 10

To a solution of N-benzyloxycarbonyl-N,N'-dimethylhydrazine (1.2 g) in dry tetrahydrofuran (20 ml) was added methyl isocyanate (352 mg) at 0° C. The mixture was stirred at 0° C. for 6 hours. After evaporation of the solvent, the residue was dissolved in ethyl acetate (50 ml). The solution was washed with 5% hydrochloric acid, 1M sodium bicarbonate solution and water successively, and dried over magnesium sulfate. After evaporation of the solvent, the residue was dissolved in methanol (20 ml) and water (2 ml). The solution was hydrogenated over 10% palladium on carbon (100 mg) at 3 atmospheric pressure of hydrogen for 1 hour. The solution was filtered and concentrated in vacuo to give N-(methylcarbamoyl)-N,N'-dimethylhydrazine (592 mg) as an oil.

Rf: 0.42 (chloroform:methanol, 10:1, V/V).

PREPARATION 11

The following compounds were obtained according to a similar manner to that of Preparation 10.

(1) 1-Isopropylcarbamoylpyrazolidine (845 mg) from 1-benzyloxycarbonylpyrazolidine (1.237 g) and isopropyl isocyanate (510.6 mg).

Rf: 0.52 (chloroform:methanol, 9:1, V/V).

(2) 1-Methylcarbamoylpyrazolidine (774 mg) from 1-benzyloxycarbonylpyrazolidine (1.237 g) and methyl isocyanate (354 µl).

Rf: 0.42 (Chloroform:methanol, 9:1, V/V).

PREPARATION 12

To a solution of N-benzyloxycarbonyl-N,N'-dimethylhydrazine (1.6 g) in toluene (30 ml) was added trichloromethyl chloroformate (0.553 ml). After the solution was refluxed for 30 minutes, dimethylamine (672 mg) and triethylamine (2.0 g) was added thereto at 0° C. The reaction mixture was stirred at ambient temperature for 2 hours. After evaporation of the solvent, the residue was dissolved in ethyl acetate (50 ml). The solution was washed with 5% hydrochloric acid, 1M sodium bicarbonate solution and water successively, and dried over magnesium sulfate. After evaporation of the solvent, the residue was dissolved in methanol (20 ml) and water (20 ml). The solution was hydrogenated over 10% palladium on carbon (100 mg) at 3 atmospheric pressure of hydrogen for 1 hour. The solution was filtered and concentrated in vacuo to give N-(N,N-dimethylcarbamoyl)-N,N'-dimethylhydrazine (820 mg) as an oil.

Rf: 0.47 (chloroform:methanol, 10:1, V/V).

PREPARATION 13

To a solution of N-t-butoxycarbonylsarcosinal (3.46 g) in dry tetrahydrofuran (100 ml) which was cooled to −78° C., was added dropwise a solution of isopentylmagnesium bromide prepared from isopentyl bromide (30.8 g) and magnesium (4.86 g) in dry tetrahydrofuran (200 ml). After the addition was complete, the reaction mixture was allowed to warm to ambient temperature and stirred at the same temperature for 4 hours. After saturated aqueous ammonium chloride (200 ml) was added thereto, the resulting mixture was extracted with diethyl ether (300 ml×2). The combined extract was dried over magnesium sulfate and concentrated under reduced pressure. The residue was purified with silicagel column chromatography (20% ethylacetate in n-hexane as eluent) to give 1-(N-t-butoxycarbonyl-N-methylamino)-2-hydroxy-5-methylhexane (3.96 g).

Rf: 0.53 (hexane:ethylacetate 2:1, V/V).

PREPARATION 14

To a solution of 1-(N-t-butoxycarbonyl-N-methylamino)-2-hydroxy-5-methylhexane (2.45 g) and triethylamine (3.03 g) in dimethyl sulfoxide (20 ml) was added sulfur trioxide pyridine complex (4.77 g) under ice-bath cooling. After the mixture was stirred at ambient temperature overnight, the reaction mixture was poured into ice-water (100 ml). The mixture was extracted with diethyl ether (100 ml×2). The extract was washed with water, dried over magnesium sulfate, and concentrated under reduced pressure. The residue was purified with silica gel column chromatography (20% ethyl acetate in n-hexane as eluent) to give 1-(N-t-butoxycarbonyl-N-methylamino)-2-oxo-5-methylhexane (2.15 g).

Rf: 0.73 (hexane:ethyl acetate, 5:2, V/V).

PREPARATION 15

To a solution of N-t-butoxycarbonyl-N,N'-dimethylethylenediamine (1.0 g) and triethylamine (537 mg) in methylene chloride (20 ml) which was cooled to 0° C., was added morpholinocarbonyl chloride (794 mg). The mixture was stirred at 0° C. for 1 hour. After evaporation of the solvent, the residue was dissolved in ethyl acetate (30 ml) and the solution was washed with 5% hydrochloric acid, 1M sodium bicarbonate solution and water successively, and dried over magnesium sulfate. Evaporation of the solvent gave N-t-butoxycarbonyl-N'-(morpholinocarbonyl)-N,N'-dimethylethylenediamine (1.11 g) as an oil.

Rf: 0.62 (chloroform:methanol, 10:1, V/V).

PREPARATION 16

The following compounds were obtained according to a similar manner to that of Preparation 15.

(1) N-t-Butoxycarbonyl-N'-isobutyryl-N,N'-dimethylethylenediamine (1.42 g) from N-t-butoxycarbonyl-N,N'-dimethylethylenediamine (1.2 g) and isobutyryl chloride (668 ml).

Rf: 0.31 (n-hexane:ethyl acetate, 1:1, V/V).

(2) N-t-Butoxycarbonyl-N'-isovaleryl-N,N'-dimethylethylenediamine (1.17 g) from N-t-butoxycarbonyl-N,N'-dimethylethylenediamine (850 mg) and isovaleryl chloride (0.55 ml)

Rf: 0.75 (chloroform:methanol, 10:1, V/V).

(3) 1-[N-(t-Butoxycarbonyl)-N-methylamino]-4-[N-(morpholinocarbonyl)-N-methylamino]butane (478 mg) from 1-[N-(t-butoxycarbonyl)-N-methylamino]-4-methylaminobutane (500 mg) and morpholinocarbonyl chloride (363 mg).

Rf: 0.30 (ethyl acetate).

(4) 1-[N-(t-Butoxycarbonyl)-N-methylamino]-3-[N-(morpholinocarbonyl)-N-methylamino]propane (930 mg) from 1-[N-(t-butoxycarbonyl)-N-methylamino]-3methylaminopropane (600 mg), morpholinocarbonyl chloride (444 mg) and triethylamine (301 mg)

Rf: 0.34 (ethyl acetate).

(5) 1-[N-(t-Butoxycarbonyl)-N-methylamino]-5-[N-(morpholinocarbonyl)-N-methylamino]pentane (881 mg) from 1-[N-(t-butoxycarbonyl)-N-methylamino]-5-methylaminopentane (576 mg), morpholinocarbonyl chloride (374 mg) and triethylamine (253 mg).

Rf: 0.74 (Chloroform:methanol, 10:1, V/V).

PREPARATION 17

To a mixture of 5-(N-t-butoxycarbonylamino)valeric acid (2.173 g) and morpholine (1.045 g) in anhydrous methylene chloride (22 ml) was added N-ethyl-N'-(3-dimethylaminopropyl)carbodiimide hydrochloride (2.30 g) portionwise at 0°–5° C. After being stirred for 3 hours at the same temperature, the solvent was evaporated in vacuo and the residue was dissolved in ethyl acetate (100 ml) and water (100 ml). The organic layer was washed with 0.5N hydrochloric acid (100 ml), water (100 ml), aqueous sodium bicarbonate (100 ml), water (100 ml) and brine (100 ml) successively, and dried over magnesium sulfate. Evaporation of the solvent gave 4-[5-(N-t-butoxycarbonylamino)valeryl]morpholine (1.668 g) as an oil.

Rf: 0.37 (ethyl acetate).

PREPARATION 18

To a solution of 4-[5-(N-t-butoxycarbonylamino)-valeryl]morpholine (1.656 g) in dry N,N-dimethylformamide (20 ml) were added sodium hydride (60% dispersion in mineral oil: 347 mg) and methyl iodide (2.462 g) at 0°–5° C. under nitrogen atmosphere. After being stirred for 6 hours at room temperature, the reaction mixture was added to ethyl acetate (200 ml) and water (200 ml). The organic layer was washed with 0.5N hydrochloric acid (200 ml), water (200 ml), aqueous sodium bicarbonate (200 ml), water (200 ml) and brine (200 ml) successively, and dried over magnesium sulfate. Evaporation of the solvent gave 4-[5-(N-methyl-N-t-butoxycarbonylamino)valeryl]morpholine (1.093 g) as an oil.

Rf: 0.38 (ethyl acetate).

PREPARATION 19

To a mixture of N-t-butoxycarbonyl-N-methyl-$\beta$-alanine (6.097 g) and triethylamine (4.18 ml) in ethyl acetate (60 ml) was added 2-bromoacetophenone (5.972 g) portionwise at 0°-5° C. After being stirred over night at ambient temperature, the solvent was evaporated and the resulting residue was dissolved in ethyl acetate (200 ml). The solution was washed with 0.5N hydrochloric acid (200 ml), water (200 ml) aqueous sodium bicarbonate (200 ml), water (200 ml) and brine (200 ml) successively, and dried over magnesium sulfate. Evaporation of the solvent gave N-t-butoxycarbonyl-N-methyl-$\beta$-alanine phenacyl ester (8.54 g) as an oil.

Rf: 0.53 (n-Hexane:ethyl acetate, 1:1, V/V).

PREPARATION 20

(1) N-Isopropyl-5-(N-t-butoxycarbonylamino)valeramide (1.524 g) was obtained according to a similar manner to that of Preparation 17 from 5-(N-t-butoxycarbonylamino)valeric acid (2.173 g) and isopropylamine (673 mg).

mp: 93.5°-95° C.
Rf: 0.46 (ethyl acetate).

(2) N-Isopropyl-N-methyl-5-(N-methyl-N-t-butoxycarbonylamino)valeramide (1.399 g) was obtained according to a similar manner to that of Preparation 18 from N-isopropyl-5-(N-t-butoxycarbonylamino)valeramide (1.502 g) and methyl iodide (4.951 g).

Rf: 0.19 (n-Hexane:ethyl acetate, 1:1, V/V).

PREPARATION 21

(1) Methyl 5-(N-t-butoxycarbonyl-N-methylamino)valerate (563 mg) was obtained according to a similar manner to that of Preparation 18 from 5-(N-t-butoxycarbonylamino)valeric acid (2.716 g) and methyl iodide (14.20 g).

Rf: 0.62 (n-Hexane:ethyl acetate, 1:1, V/V).

(2) A mixture of methyl 5-(N-t-butoxycarbonyl-N-methylamino)valerate (557 mg) in methanol (6 ml) and 1N sodium hydroxide solution (3.41 ml) was stirred at ambient temperature for 1 hour. The solution was concentrated in vacuo, and the residue was poured into water (20 ml) and diethyl ether (20 ml). The aqueous layer was separated and acidified with 1N hydrochloric acid, and extracted with ethyl acetate (20 ml×3). The extract was collected and washed with water (40 ml×2) and brine (40 ml) successively, and dried over magnesium sulfate. Evaporation of the solvent gave 5-(N-t-butoxycarbonyl-N-methylamino)valeric acid (470 mg) as an oil.

Rf: 0.43 (chloroform:methanol:acetic acid, 16:1:1, V/V).

(3) N-Isopropyl-5-(N-t-butoxycarbonyl-N-methylamino)valeramide (384 mg) was obtained according to a similar manner to that of Preparation 17 from 5-(N-t-butoxycarbonyl-N-methylamino)valeric acid (454 mg) and isopropylamine (132 mg).

Rf: 0.17 (n-Hexane:ethyl acetate, 1:1, V/V).

PREPARATION 22

(1) 4-[4-(N-t-Butoxycarbonylamino)butyryl]morpholine (1.73 g) was obtained according to a similar manner to that of Preparation 17 from 4-(N-t-butoxycarbonylamino)butyric acid (2.03 g) and morpholine (0.88 g).

Rf: 0.50 (chloroform:methanol, 10:1, V/V).

(2) 4-[4-(N-t-Butoxycarbonyl-N-methylamino)butyryl]morpholine was obtained according to a similar manner to that of Preparation 18.

Rf: 0.58 (chloroform:methanol, 10:1, V/V).

PREPARATION 23

(1) N-Isopropyl-4-(N-t-butoxycarbonyl-N-methylamino)butyramide (3.13 g) was obtained according to a similar manner to that of Preparation 17 from 4-(N-t-butoxycarbonyl-N-methylamino)butyric acid (3.26 g) and isopropylamine (0.91 g).

Rf: 0.62 (chloroform:methanol, 10:1, V/V).

(2) N-Isopropyl-N-methyl-4-(N-t-butoxycarbonyl-N-methylamino)butyramide was obtained according to a similar manner to that of Preparation 18.

Rf: 0.72 (chloroform:methanol, 10:1, V/V).

PREPARATION 24

(1) N-t-Butoxycarbonyl-N-methyl-$\beta$-alanine methyl ester (15.12 g) was obtained according to a similar manner to that of Preparation 18 from N-t-butoxycarbonyl-$\beta$-alanine (28.38 g) and methyl iodide (102.1 g).

Rf: 0.61 (n-hexane:ethyl acetate, 1:1, V/V).

(2) To a solution of N-t-butoxycarbonyl-N-methyl-$\beta$-alanine methyl ester (3.911 g) in methanol (20 ml) and water (20 ml) was added sodium borohydride (6.81 g) portionwise at 4° C. and the mixture was stirred at room temperature for 3 hours.

The solution was concentrated in vacuo, and the residue was portioned between ethyl acetate (100 ml) and 0.5N hydrochloric acid (100 ml). The separated organic layer was washed with 0.5N hydrochloric acid (100 ml), water (100 ml), aqueous sodium bicarbonate (100 ml), water (100 ml) and brine (100 ml) successively, and dried over magnesium sulfate. Evaporation of the solvent gave 3-(N-t-butoxycarbonyl-N-methylamino)propanol (2.48 g) as an oil.

Rf: 0.28 (n-hexane:ethyl acetate, 1:1, V/V).

(3) A solution of 3-(N-t-butoxycarbonyl-N-methylamino)propanol (2.40 g) and triethylamine (2.07 g) in methylene chloride (25 ml) was cooled to 0° C. and treated with methanesulfonyl chloride (1.883 g). After being stirred for 1 hour at 0°-4° C., the solution was evaporated in vacuo. The residue was partitioned between ethyl acetate (25 ml) and water (50 ml). The separated organic layer was washed with 0.5N hydrochloric acid (50 ml), water (50 ml), aqueous sodium bicarbonate (50 ml), water (50 ml) and brine (50 ml) successively, and dried over magnesium sulfate. The evaporation of the solvent gave 3-(N-t-butoxycarbonyl-N-methylamino)propyl methanesulfonate (3.742 g) as an oil.

Rf: 0.18 (Ethyl acetate).

(4) To a stirred suspension of sodium hydride (336 mg: 60% dispersion in oil) in anhydrous tetrahydrofuran (12 ml) was added a solution of 3-(N-t-butoxycarbonyl-N-methylamino)propyl methanesulfonate (2.139 g) in tetrahydrofuran (10 ml) dropwise over 5 minutes. After being stirred for 30 minutes, the mixture was cooled to 0° C., and 2-methyl-1-propanethiol (758 mg)

was added dropwise at 0°-5° C. The mixture was then allowed to warm to ambient temperature and stirred for 24 hours. Additional 168 mg of sodium hydride and 379 mg of 2-methyl-1-propanethiol was added above the same condition. After being stirred for another 16 hours, the solvent was evaporated and the resulting residue was dissolved in ethyl acetate (100 ml). The solution was washed with 0.5N hydrochloric acid (100 ml), water (100 ml), aqueous sodium bicarbonate (100 ml), water (100 ml), and brine (100 ml) successively, dried over magnesium sulfate and concentrated. The residue was chromatographed on silica gel eluting with a mixture of n-hexane and ethyl acetate (6:4 V/V) to give 3-(N-t-butoxycarbonyl-N-methylamino)propyl isobutyl sulfide (595 mg) as an oil.

Rf: 0.83 (n-hexane: ethyl acetate, 1:1, V/V).

PREPARATION 25

(1) To a solution of 2-(N-t-butoxycarbonyl)aminoethanethiol (3.55 g) in N,N-dimethylformamide (10 ml) was added a solution of 2.2N sodium hydroxide (10 ml) under ice-bath cooling. The mixture was stirred at ambient temperature for 20 minutes, then a solution of 2-iodopropane (3.74 g) in N,N-dimethylformamide (2 ml) was added thereto under ice-bath cooling. After being stirred at ambient temperature for 1 hour, the mixture was poured into ice-water (20 ml). The mixture was neutralized with 10% hydrochloric acid, then extracted with ethyl acetate (40 ml×2). The extract was washed with water, dried over magnesium sulfate, and concentrated under reduced pressure. The residue was purified with silica gel column chromatography, eluting with a mixture of hexane and ethyl acetate (8:1, V/V) to give 2-(N-t-butoxycarbonylamino)ethyl isopropyl sulfide (3.88 g).

Rf: 0.46 (hexane:ethyl acetate, 5;1, V/V).

(2) 2-(N-t-Butoxycarbonyl-N-methylamino)ethyl isopropyl sulfide was obtained according to a similar manner to that of Preparation 18.

Rf: 0.55 (hexane:ethyl acetate, 5:1, V/V).

PREPARATION 26

(1) To a solution of N-t-butoxycarbonyl-N-methyl-β-alanine (610 mg) in dry methylene chloride (10 ml) which was cooled to 0° C., were added oxalyl chloride (439 ml) and three drops of N,N-dimethylformamide. The mixture was stirred at the same temperature for 30 minutes. After evaporation of the solvent, the residue was dissolved in dry methylene chloride (10 ml) and 2-mercaptopyridine (350 mg) was added to the solution at 0° C. The mixture was stirred at the same temperature for 4 hours. After evaporation of the solvent, the residue was dissolved in ethyl acetate (50 ml) and the solution was washed with 0.5% hydrochloric acid, 1M sodium bicarbonate solution and water successively, and dried over magnesium sulfate. Evaporation of the solvent gave S-2-pyridyl 3-(N-t-butoxycarbonyl-N-methylamino)propanethioate (490 mg) as an amorphous powder.

Rf: 0.61 (n-hexane:ethyl acetate, 1:1, V/V).

(2) To a solution of S-2-pyridyl 3-(N-t-butoxycarbonyl-N-methylamino)propanethioate (490 mg) in dry tetrahydrofuran (20 ml) which was cooled to 0° C., was added dropwise a solution of isobutylmagnesium bromide prepared from isobutyl bromide (1.13 g) and magnesium (200 mg) in dry tetrahydrofuran (30 ml), and the mixture was stirred at the same temperature for 1 hour. The reaction mixture was poured into saturated aqueous ammonium chloride (50 ml). The resulting slurry was extracted with diethyl ether (50 ml×2), and the combined extract was dried over magnesium sulfate and concentrated to give 1-(N-t-butoxycarbonyl-N-methylamino)-3-oxo-5-methyl-hexane (400 mg) as an oil.

Rf: 0.64 (n-hexane:ethyl acetate, 2:1, V/V).

PREPARATION 27

(1) A mixture of ethylenediamine (308 g) and methyl isobutyrate (87.15 g) was stirred at 80° C. for 15 hours. After removal of excess ethylenediamine under reduced pressure, the residue was dissolved in ethyl acetate (100 ml). Insoluble material was filtered off and the filtrate was concentrated and distilled to give N-isobutyrylethylenediamine (84.45 g).

bp: 106°-108° C./1 mmHg.

(2) A solution of di-t-butyldicarbonate (137.5 g) in methylene chloride (1 l) was added dropwise to a solution of N-isobutyrylethylenediamine (82.02 g) in methylene chloride (1 l) under ice-bath cooling. After the mixture was stirred for 3 hours at ambient temperature, the solvent was evaporated under reduced pressure. The residue was recrystallized from n-hexane-ethyl acetate (2:1, V/V, 1.6 l) to give N-t-butoxycarbonyl-N'-isobutyrylethylenediamine (117.6 g).

mp: 116°-117° C.

(3) N-t-Butoxycarbonyl-N'-isobutyryl-N,N'-dimethylethylenediamine (129 g) was obtained according to a similar manner to that of Preparation 18 from N-t-butoxycarbonyl-N'-isobutylethylenediamine (105 g), methyl iodide (85.2 ml) and 60% sodium hydride (38.3 g).

Rf: 0.59 (chloroform:methanol, 10:1, V/V).

t-Butoxycarbonyl groups of the compounds obtained in Preparations 13 to 27 were eliminated according to a similar manner to that of Preparation 2, and thus obtained trifluoroacetic acid salt compounds were used as starting compounds in Preparation 33.

PREPARATION 28

The following compounds were obtained according to a similar manner to that of Preparation 15.

(1) 1-Acetyl-2-benzyloxycarbonylperhydropyridazine (647 mg) from acetyl chloride (195.5 μl) and 1-benzyloxycarbonylperhydropyridazine (550.7 mg).

Rf: 0.68 (chloroform:methanol, 9:1, V/V).

(2) 1-Benzyloxycarbonyl-2-butyrylperhydropyridazine (782 mg) was obtained from butyryl chloride (287.3 μl) and 1-benzyloxycarbonylperhydropyridazine (550.7 mg).

Rf: 0.79 (chloroform:methanol, 9:1, V/V).

(3) 1-Benzyloxycarbonyl-2-isobutyrylperhydropyridazine (320 mg) from 1-benzyloxycarbonylperhydropyridazine (220.3 mg) and isobutyryl chloride (116 μl).

Rf: 0.84 (chloroform:methanol, 9:1, V/V).

(4) 1-Benzoyl-2-benzyloxycarbonylperhydropyridazine (350 mg) from 1-benzyloxycarbonylperhydropyridazine (220.3 mg) and benzoyl chloride (127 μl).

Rf: 0.76 (chloroform:methanol, 9:1, V/V).

(5) 1-Benzyloxycarbonyl-2-cyclohexylcarbonylperhydropyridazine (427 mg) from 1-benzyloxycarbonylperhydropyridazine (220.3 mg) and cyclohexylcarbonyl chloride (148 μl).

Rf: 0.83 (chloroform:methanol, 9:1, V/V).

(6) 1-Acetyl-2-benzyloxycarbonylpyrazolidine (222 mg) from acetyl chloride (78.2 μl) and 1-benzyloxycarbonylpyrazolidine (206.2 mg).

Rf: 0.66 (chloroform:methanol, 9:1, V/V).

(7) 1-Benzyloxycarbonyl-2-isobutyrylpyrazolidine (1.796 g) from 1-benzyloxycarbonylpyrazolidine (1.237 g) and isobutyryl chloride (696 μl).

Rf: 0.82 (chloroform:methanol, 9:1, V/V).

(8) 1-Benzyloxycarbonyl-2-methoxyacetylpyrazolidine (973 mg) from 1-benzyloxycarbonylpyrazolidine (825 mg) and methoxyacetyl chloride (366 μl).

Rf: 0.74 (chloroform:methanol, 9:1, V/V).

(9) 1-Benzyloxycarbonyl-2-morpholinocarbonylpyrazolidine (1.797 g) from 1-benzyloxycarbonylpyrazolidine (1.237 g) and morpholinocarbonyl chloride (0.897 g).

Rf: 0.76 (chloroform:methanol, 9:1, V/V).

PREPARATION 29

The following compounds were obtained according to a similar manner to that of Preparation 1.

(1) 1-Benzyloxycarbonyl-2-(4-dimethylaminobutyryl)pyrazolidine (1.47 g) from 1-benzyloxycarbonylpyrazolidine (1.237 g) and 4-dimethylaminobutyric acid hydrochloride (1.01 g).

Rf: 0.62 (chloroform:methanol, 9:1, V/V).

(2) 1-Benzyloxycarbonyl-2-benzoylaminoacetylpyrazolidine (1.36 g) from 1-benzyloxycarbonylpyrazolidine (825 mg) and hippuric acid (717 mg).

Rf: 0.68 (chloroform:methanol, 9:1, V/V).

(3) 1-Benzyloxycarbonyl-2-(N-t-butoxycarbonyl-L-leucyl)pyrazolidine (4.25 g) from 1-benzyloxycarbonylpyrazolidine (2.475 g) and N-t-butoxycarbonyl-L-leucine (2.988 g).

Rf: 0.88 (chloroform:methanol, 9:1, V/V).

(4) 1-Benzyloxycarbonyl-2-(N-acetyl-L-leucyl)-pyrazolidine (2.35 g) from 1-benzyloxycarbonylpyrazolidine (1.718 g) and N-acetyl-L-leucine (1.442 g).

Rf: 0.70 (chloroform:methanol, 9:1, V/V).

(5) 1-Benzyloxycarbonyl-2-(N$^\alpha$-t-butoxycarbonyl-N$^{im}$-tosyl-L-histidyl)pyrazolidine (2.442 g) from 1-Benzyloxycarbonylpyrazolidine (2.475 g) and N$^\alpha$-t-butoxycarbonyl-N$^{im}$-tosyl-L-histidine (4.913 g).

Rf: 0.72 (chloroform:methanol, 9:1, V/V).

Benzyloxycarbonyl groups of the compounds obtained in Preparations 28 and 29 were eliminated according to a similar manner to that of Preparation 10, and thus obtained compounds were used as starting compounds in Preparation 33.

PREPARATION 30 t-Butoxycarbonylglycylpiperazine (2.13 g) was obtained according to a similar manner to that of Preparation 1 from piperazine (1.034 g) and t-butoxycarbonylglycine (2.102 g).

mp: 169°–170.5° C.

Rf: 0.48 (chloroform:methanol, 9:1, V/V).

PREPARATION 31

To a solution of benzyl 2(S)-hydroxy-3-phenylpropionate (256 mg) in dry tetrahydrofuran (10 ml) was added trichloromethyl chloroformate (0.122 ml). The mixture was refluxed for 18 hours. The mixture was cooled to 0° C., and morpholine (348 mg) was added thereto. The mixture was stirred at the same temperature for 3 hours. After evaporation of the solvent, the residue was dissolved in ethyl acetate (40 ml). The solution was washed with 5% hydrochloric acid, 1M sodium bicarbonate solution and water successively, dried over magnesium sulfate, and concentrated under reduced pressure. The residue was purified with silica gel column chromatography (25% ethyl acetate in n-hexane as eluent) to give benzyl 2(S)-morpholinocarbonyloxy-3-phenylpropionate (367 mg) as an oil.

Rf: 0.52 (ethyl acetate:n-hexane, 2:1, V/V).

PREPARATION 32

To a solution of benzyl 2(S)-hydroxy-3-phenylpropionate (513 mg) in dry tetrahydrofuran (10 ml) was added trichloromethyl chloroformate (0.244 ml). The mixture was refluxed for 18 hours. The mixture was cooled to 0° C., and a solution of 4-(N-methyl-β-alanyl)-morpholine trifluoroacetic acid salt (1.44 g) and triethylamine (701 mg) in dry tetrahydrofuran (10 ml) was added thereto. The mixture was stirred at ambient temperature for 2 hours. After evaporation of the solvent, the residue was dissolved in ethyl acetate (50 ml). The solution was washed with 50% hydrochloric acid, 1M sodium bicarbonate solution and water successively, dried over magnesium sulfate, and concentrated under reduced pressure. The residue was purified with silicagel column chromatography (50% ethyl acetate in n-hexane as eluent) to give benzyl 2(S)-[N-(2-morpholinocarbonylethyl)-N-methylaminocarbonyloxy]-3-phenylpropionate (726 mg) as an oil.

Rf: 0.49 (ethyl acetate).

PREPARATION 33

The following compounds were obtained according to a similar manner to that of Preparation 31 or 32.

(1) Benzyl 2(S)-(N,N-diethylaminocarbonyloxy)-3-phenylpropionate

Rf: 0.64 (n-hexane:ethyl acetate, 2:1, V/V).

(2) Benzyl 2(S)-(2-methoxyethylaminocarbonyloxy)-3-phenylpropionate

Rf: 0.63 (n-hexane:ethyl acetate, 2:1, V/V).

(3) Benzyl 2(S)-(N-methoxycarbonylmethyl-N-methylaminocarbonyloxy)-3-phenylpropionate Rf: 0.29 (n-hexane:ethyl acetate, 2:1, V/V).

(4) Benzyl 2(S)-[N-(2-hydroxyethyl)-N-methylaminocarbonyloxy]-3-phenylpropionate Rf: 0.67 (ethyl acetate).

(5) Benzyl 2(S)-(N'-acetyl-N'-methyl-N-methylhydrazinocarbonyloxy)-3-phenylpropionate Rf: 0.38 (n-hexane:ethyl acetate, 1:1, V/V).

(6) Benzyl 2(S)-(2(S)-methoxycarbonylpyrrolidine-1-carbonyloxy)-3-phenylpropionate Rf: 0.36 (n-hexane:ethyl acetate, 2:1, V/V).

(7) Benzyl 2(S)-(N-n-butyl-N-ethylaminocarbonyloxy)-3-phenylpropionate

Rf: 0.69 (n-hexane:ethyl acetate, 2:1, V/V).

(8) Benzyl 2(S)-(N-methyl-N-phenethylaminocarbonyloxy)-3-phenylpropionate

Rf: 0.58 (n-hexane:ethyl acetate, 2:1, V/V).

(9) Benzyl 2(S)-(2(R)-methoxycarbonylpyrrolidine-1-carbonyloxy)-3-phenylpropionate Rf: 0.35 (n-hexane:ethyl acetate, 2:1, V/V).

(10) Benzyl 2(S)-(N-n-butyl-N-methylaminocarbonyloxy)-3-phenylpropionate

Rf: 0.67 (n-hexane:ethyl acetate, 2:1, V/V).

(11) Benzyl 2(S)-(N-methyl-N-phenylaminocarbonyloxy)-3-phenylpropionate

Rf: 0.65 (n-hexane:ethyl acetate, 2:1, V/V).

(12) Benzyl 2(S)-(2(S)-hydroxymethylpyrrolidine-1-carbonyloxy)-3-phenylpropionate Rf: 0.19 (n-hexane:ethyl acetate, 2:1, V/V).

(13) Benzyl 2(S)-hexamethyleneiminocarbonyloxy-3-phenylpropionate
Rf: 0.62 (n-hexane:ethyl acetate, 2:1, V/V).

(14) Benzyl 2(S)-(2(R)-hydroxymethylpyrrolidine-1-carbonyloxy)-3-phenylpropionate
Rf: 0.16 (n-hexane:ethyl acetate, 2:1, V/V).

(15) Benzyl 2(S)-[N-(1(R)-morpholinocarbonylethyl)-N-methylaminocarbonyloxy]-3-phenylpropionate
Rf: 0.58 (n-hexane:ethyl acetate, 1:3, V/V).

(16) Benzyl 2(S)-[N-(2-dimethylaminocarbonylethyl)-N-methylaminocarbonyloxy]-3-phenylpropionate
Rf: 0.43 (ethyl acetate).

(17) Benzyl 2(S)-(N-morpholinocarbonylmethyl-N-methyl-aminocarbonyloxy)-3-phenylpropionate
Rf: 0.35 (ethyl acetate).

(18) Benzyl 2(S)-(N-dimethylaminocarbonylmethyl-N-methylaminocarbonyloxy)-3-phenylpropionate
Rf: 0.44 (ethyl acetate).

(19) Benzyl 2(S)-[N-(n-butylaminocarbonylmethyl)-N-methylaminocarbonyloxy]-3-phenylpropionate
mp 98°–50° C.
Rf: 0.61 (ethyl acetate:n-hexane, 3:1, V/V).

(20) Benzyl 2(S)-[N-(4-picolylaminocarbonylmethyl)-N-methylaminocarbonyloxy]-3-phenylpropionate
mp: 98°–100° C.
Rf: 0.60 (chloroform:methanol, 6:1, V/V).

(21) Benzyl 2(S)-[N-(N-methyl-N-phenethylaminocarbonylmethyl)-N-methylaminocarbonyloxy]-3-phenylpropionate
Rf: 0.52 (n-hexane:ethyl acetate, 1:3, V/V).

(22) Benzyl 2(S)-(2(R)-Dimethylaminocarbonylpyrrolidine-1-carbonyloxy)-3-phenylpropionate
Rf: 0.31 (ethyl acetate).

(23) Benzyl 2(S)-(6(S)-2-oxo-1,4-diazabicyclo[4.3.0]-nonane-4-carbonyloxy)-3-phenylpropionate
Rf: 0.42 (ethyl acetate).

(24) Benzyl 2(S)-(4-Methyl-3-oxopiperazine-1-carbonyloxy)-3-phenylpropionate
Rf: 0.41 (ethyl acetate).

(25) Benzyl 2(S)-(3-oxopiperazine-1-carbonyloxy)-3-phenylpropionate
Rf: 0.38 (ethyl acetate).

(26) Benzyl 2(S)-(N-isobutoxycarbonylmethyl-N-methylaminocarbonyloxy)-3-phenylpropionate
Rf: 0.69 (n-hexane:ethyl acetate, 2:1, V/V).

(27) Benzyl 2(S)-(N-methyl-N-phenethyloxycarbonylmethylaminocarbonyloxy)-3-phenylpropionate
Rf: 0.72 (n-hexane:ethyl acetate, 2:1, V/V).

(28) Benzyl 2(S)-[N-methyl-N-(5-methyl-2-oxohexyl)aminocarbonyloxy]-3-phenylpropionate
Rf: 0.62 (n-hexane:ethyl acetate, 2:1, V/V).

(29) Benzyl 2(S)-[N-methyl-N-(2-hydroxy-5-methylhexyl)aminocarbonyloxy]-3-phenylpropionate
Rf: 0.42 (n-hexane:ethyl acetate, 2:1, V/V).

(30) Benzyl 2(S)-[N-methyl-N-(2-oxopropoxycarbonylmethyl)aminocarbonyloxy]-3-phenylpropionate
Rf: 0.82 (chloroform:methanol, 10:1, V/V).

(31) Benzyl 2(S)-[N-{2-(ethoxycarbonylmethylaminocarbonyl)ethyl}-N-methylaminocarbonyloxy]-3-phenylpropionate
Rf: 0.88 (chloroform:methanol, 10:1, V/V).

(32) Benzyl 2(S)-(2(S)-methoxymethylpyrrolidine-1-carbonyloxy)-3-phenylpropionate
Rf: 0.92 (ethyl acetate).

(33) Benzyl 2(S)-[N-{2-(2-morpholiuoethylaminocarbonyl)ethyl}-N-methylaminocarbonyloxy]-3-phenylpropionate
Rf: 0.59 (chloroform:methanol, 9:1, V/V).

(34) Benzyl 2(S)-[N-{2-(2-picolylaminocarbonyl)ethyl}-N-methylaminocarbonyloxy]-3-phenylpropionate
Rf: 0.21 (ethyl acetate).

(35) Benzyl 2(S)-[N-[2-[N-[2-(2-pyridyl)ethyl}-N-methylaminocarbonyl]ethyl]-N-methylaminocarbonyloxy]-3-phenylpropionate
Rf: 0.15 (ethyl acetate).

(36) Benzyl 2(S)-[N-{2-(3-picolylaminocarbonyl)ethyl}-N-methylaminocarbonyloxy]-3-phenylpropionate
Rf: 0.11 (ethyl acetate).

(37) Benzyl 2(S)-[N-[2-{N-(2-pyridyl)-N-methylaminocarbonyl}ethyl]-N-methylaminocarbonyloxy]-3-phenylpropionate
Rf: 0.25 (ethyl acetate).

(38) Benzyl 2(S)-[N-(2-isopropylaminocarbonylethyl)-N-methylaminocarbonyloxy]-3-phenylpropionate
Rf: 0.67 (ethyl acetate).

(39) Benzyl 2(S)-[N-{2-(4-methylpiperazine-1-carbonyl)ethyl}-N-methylaminocarbonyloxy]-3-phenylpropionate
Rf: 0.47 (chloroform:methanol, 9:1, V/V).

(40) Benzyl 2(S)-[N-(2-thiomorpholinocarbonylethyl)-N-methylaminocarbonyloxy]-3-phenylpropionate
Rf: 0.76 (ethyl acetate).

(41) Benzyl 2(S)-[N-{2-(2-thiazolylaminocarbonyl)ethyl}-N-methylaminocarbonyloxy]-3-phenylpropionate
Rf: 0.83 (ethyl acetate).

(42) Benzyl 2(S)-[N-{2-(1,2,3,6-tetrahydropyridine-1-carbonyl)ethyl}-N-methylaminocarbonyloxy]-3-phenylpropionate
Rf: 0.83 (ethyl acetate).

(43) Benzyl 2(S)-(2-isopropylcarbamoylpyrazolidine-1-carbonyloxy)-3-phenylpropionate
Rf: 0.73 (chloroform:methanol, 9:1, V/V).

(44) Benzyl 2(S)-[N'-(methylcarbamoyl)-N,N'-dimethylhydrazinocarbonyloxy]-3-phenylpropionate
Rf: 0.68 (ethyl acetate).

(45) Benzyl 2(S)-[N'-(N,N-dimethylcarbamoyl)-N,N'-dimethylhydrazinocarbonyloxy]-3-phenylpropionate
Rf: 0.79 (ethyl acetate).

(46) Benzyl 2(S)-[N'-(morpholinocarbonyl)-N,N'-dimethylhydrazinocarbonyloxy]-3-phenylpropionate
Rf: 0.36 (chloroform:methanol, 10:1, V/V).

(47) Benzyl 2(S)-[N'-(isopropylcarbamoyl)-N,N'-dimethylhydrazinocarbonyloxy]-3-phenylpropionate
Rf: 0.77 (ethyl acetate).

(48) Benzyl 2(S)-[N'-(benzylcarbamoyl)-N,N'-dimethylhydrazinocarbonyloxy]-3-phenylpropionate
Rf: 0.42 (chloroform:methanol, 10:1, V/V).

(49) Benzyl 2(S)-(N'-isobutoxycarbonyl-N,N'-dimethylhydrazinocarbonyloxy)-3-phenylpropionate
Rf: 0.36 (chloroform:methanol, 10 1, V/V).

(50) Benzyl 2(S)-[N-(2-hydroxyethyl)-N-ethylaminocarbonyloxy]-3-phenylpropionate
Rf: 0.64 (ethyl acetate).

(51) Benzyl 2(S)-[N-methyl-N-[2-{N-(morpholinocarbonyl)-N-methylamino}ethyl]aminocarbonyloxy]-3-phenylpropionate
Rf: 0.43 (ethyl acetate).

(52) Benzyl 2(S)-[N-methyl-N-{2-(N-isobutyryl-N-methylamino)ethyl}aminocarbonyloxy]-3-phenylpropionate
Rf: 0.57 (ethyl acetate).

(53) Benzyl 2(S)-[N-methyl-N-{2-(N-isovaleryl-N-methylamino)ethyl}aminocarbonyloxy]-3-phenylpropionate
Rf: 0.64 (ethyl acetate).

(54) Benzyl 2(S)-[N-methyl-N-[4-{N-(morpholinocarbonyl)-N-methylamino}butyl]aminocarbonyloxy}-3-phenylpropionate
Rf: 0.34 (ethyl acetate).

(55) Benzyl 2(S)-[N-(4-morpholinocarbonylbutyl)-N-methylaminocarbonyloxy]-3-phenylpropionate
Rf: 0.34 (ethyl acetate).

(56) Benzyl 2(S)-(3-hydroxypiperidinocarbonyloxy)-3-phenylpropionate (490 mg) from benzyl 2(S)-hydroxy-3-phenylpropionate (513 mg), 3-nydroxypiperidine hydrochloride (551 mg) and triethylamine (405 mg)
Rf: 0.70 (ethyl acetate).

(57) Benzyl 2(S)-[N-methyl-N-(2-phenacyloxycarbonylethyl)aminocarbonyloxy]-3-phenylpropionate
Rf: 0.78 (ethyl acetate).

(58) Benzyl 2(S)-[N-{4-(N-methyl-N-isopropylcarbamoyl)butyl}-N-methylaminocarbonyloxy]-3-phenylpropionate
Rf: 0.59 (ethyl acetate).

(59) Benzyl 2(S)-[N-(4-isopropylcarbamoylbutyl)-N-methylaminocarbonyloxy]-3-phenylpropionate
Rf: 0.56 (ethyl acetate).

(60) Benzyl 2(S)-[N-methyl-N-[3-{N-(morpholinocarbonyl)-N-methylamino}propyl]aminocarbonyloxy]-3-phenylpropionate
Rf: 0.31 (ethyl acetate).

(61) Benzyl 2(S)-[N-methyl-N-(3-morpholinocarbonylpropyl)aminocarbonyloxy]-3-phenylpropionate
Rf: 0.20 (ethyl acetate:n-hexane, 5:1, V/V).

(62) Benzyl 2(S)-[N-methyl-N-{3-(N-isopropyl-N-methylcarbamoyl)propyl}aminocarbonyloxy]-3-phenylpropionate
Rf: 0.48 (ethyl acetate:n-hexane, 5:1, V/V).

(63) Benzyl 2(S)-[N-Methyl-N-{2-(N-t-butoxycarbonyl-N-methylamino)ethyl}aminocarbonyloxy]-3-phenylpropionate (1.6 g) from benzyl 2(S)-hydroxy-3-phenylpropionate (1.36 g) and N-t butoxycarbonyl-N,N'-dimethylethylenediamine (1.0 g).
Rf: 0.59 (n-hexane:ethyl acetate, 1:1, V/V).

(64) Benzyl 2(S)-[N-(3-isobutylthiopropyl)-N-methylaminocarbonyloxy]-3-phenylpropionate
Rf: 0.53 (n-hexane:ethyl acetate, 1:1, V/V).

(65) Benzyl 2(S)-[N-methyl-N-[5-{N-(morpholinocarbonyl)-N-methylamino}pentyl]aminocarbonyloxy]-3-phenylpropionate
Rf: 0.43 (ethyl acetate).

(66) Benzyl 2(S)-[N-methyl-N-(3-isopropylcarbamoylpropyl)aminocarbonyloxy]-3-phenylpropionate
Rf: 0.32 (ethyl acetate : n-hexane, 5:1, V/V).

(67) Benzyl 2(S)-[N-methyl-N-(3-oxo-5-methylhexyl)aminocarbonyloxy]-3-phenylpropionate
Rf: 0.52 (n-hexane:ethyl acetate, 2:1, V/V).

(68) Benzyl 2(S)-[N-(2-isopropylthioethyl)-N-methylaminocarbonyloxy]-3-phenylpropionate
Rf: 0.46 (n-hexane:ethyl acetate, 2:1, V/V).

(69) Benzyl 2(S)-(2-acetylperhydropyridazine-1-carbonyloxy)-3-phenylpropionate
Rf: 0.41 (ethyl acetate:n-hexane, 1:1, V/V).

(70) Benzyl 2(S)-(2-butyrylperhydropyridazine-1-carbonyloxy)-3-phenylpropionate
Rf: 0.68 (ethyl acetate : n-hexane, 1:1, V/V).

(71) Benzyl 2(S)-(2-isobutyrylperhydropyridazine-1-carbonyloxy)-3-phenylpropionate
Rf: 0.66 (ethyl acetate:n-hexane, 1:1, V/V).

(72) Benzyl 2(S)-(2-benzoylperhydropyridazine-1-carbonyloxy)-3-phenylpropionate
Rf: 0.66 (ethyl acetate:n-hexane, 1:1, V/V).

(73) Benzyl 2(S)-(2-cyclohexylcarbonylperhydropyridazine-1-carbonyloxy)-3-phenylpropionate
Rf: 0.72 (ethyl acetate:n-hexane, 1:1, V/V).

(74) Benzyl 2(S)-(2-acetylpyrazolidine-1-carbonyloxy)-3-phenylpropionate
Rf: 0.25 (ethyl acetate:n-hexane, 1:1, V/V).

(75) Benzyl 2(S)-(2-isobutyrylpyrazolidine-1-carbonyloxy)-3-phenylpropionate
Rf: 0.50 (ethyl acetate:n-hexanae, 1:1, V/V).

(76) Benzyl 2(S)-(2-methoxyacetylpyrazolidine-1-carbonyloxy)-3-phenylpropionate
Rf: 0.20 (ethyl acetate:n-hexane, 1:1, V/V).

(77) Benzyl 2(S)-[2-(4-dimethylaminobutyryl)-pyrazolidine-1-carbonyloxy]-3-phenylpropionate
Rf: 0.17 (chloroform:methanol, 9:1, V/V).

(78) Benzyl 2(S)-(2-benzoylaminoacetylpyrazolidine-1-carbonyloxy)-3-phenylpropionate
Rf: 0.19 (ethyl acetate:n-hexane, 1:1, V/V).

(79) Benzyl 2(S)-(2-methylcarbamoylpyrazolidine-1-carbonyloxy)-3-phenylpropionate
Rf: 0.67 (chloroform:methanol, 9:1, V/V).

(80) Benzyl 2(S)-(2-morpholinocarbonylpyrazolidine-1-carbonyloxy)-3-phenylpropionate
Rf: 0.45 (ethyl acetate).

(81) Benzyl 2(S)-[2-(N-t-butoxycarbonyl-L-leucyl)-pyrazolidine-1-carbonyloxy]-3-phenylpropionate
Rf: 0.50 (ethyl acetate:n-hexane, 1:1, V/V).

(82) Benzyl 2(S)-[2-(N-acetyl-L-leucyl)pyrazolidine-1carbonyloxy]-3-phenylpropionate
Rf: 0.30 (ethyl acetate).

(83) Benzyl 2(S)-[2-(N$^\alpha$-t-butoxycarbonyl-N$^{im}$-tosyl-L-histidyl)pyrazolidine-1-carbonyloxy]-3-phenylpropionate
Rf: 0.18 (ethyl acetate:n-hexane, 1:1, V/V).

(84) Benzyl 2(S)-(4-methylpiperazine-1-carbonyloxy)-3-phenylpropionate
Rf: 0.25 (ethyl acetate).

(85) Benzyl 2(S)-(4-methylcarbamoylpiperazine-1-carbonyloxy)-3-phenylpropionate
Rf: 0.21 (ethyl acetate).

(86) Benzyl 2(S)-[4-(t-butoxycarbonylglycyl)piperazine-1carbonyloxy]-3-phenylpropionate
Rf: 0.33 (ethyl acetate:n-hexane, 1:1, V/V).

(87) Benzyl 2(S)-[4-(morpholinocarbonyl)piperazine-1carbonyloxy]-3-phenylpropionate
Rf: 0.49 (ethyl acetate).

(88) Benzyl 2(S)-(3-hydroxypyrrolidine-1-carbonyloxy)-3-phenylpropionate
Rf: 0.61 (ethyl acetate).

(89) Benzyl 2(S)-(2-oxazolidinone-3-carbonyloxy)-3-phenylpropionate
Rf: 0.41 (ethyl acetate:n-hexane, 1:1, V/V).

(90) Benzyl 2(S)-(1,2,3,6-tetrahydropyridine-1-carbonyloxy)-3-phenylpropionate
Rf: 0.81 (ethyl acetate:n-hexane, 1:1, V/V).

(91) Benzyl 2(S)-(3-thiazolidinecarbonyloxy)-3-phenylpropionate
mp: 75°-75.5° C.
Rf: 0.75 (ethyl acetate:n-hexane, 1:1, V/V).

(92) Benzyl 2(S)-thiomorpholinocarbonyloxy-3-phenylpropionate
Rf: 0.82 (ethyl acetate:n-hexane, 1:1, V/V).

(93) Benzyl 2(S)-(2(R)-methyl-3(R)-dimethylcarbamoylmorpholinocarbonyloxy)-3-phenylpropionate
Rf: 0.64 (ethyl acetate).

(94) Benzyl 2(S)-(2(S)-isobutyl-4-methyl-3-oxopiperazine-1-carbonyloxy)-3-phenylpropionate
Rf: 0.73 (ethyl acetate).

(95) Benzyl 2(S)-(6(S)-3(S)-morpholinocarbonylmethyl-2-oxo-1,4-diazabicyclo[4.3.0]nonane-4-carbonyloxy)-3-phenylpropionate Rf: 0.78 (chloroform:methanol, 10:1, V/V).

PREPARATION 34

To a solution of benzyl 2(S)-[N-methyl-N-(2-phenacyloxycarbonylethyl)aminocarbonyloxy]-3-phenylpropionate (1.0 g) in acetic acid (10 ml) was added zinc dust (1.0 g) portionwise at ambient temperature. After being stirred for 2 hours, zinc dust (0.2 g) was added thereto. The reaction mixture was stirred overnight at the same temperature and filtered, and the filtrate was evaporated in vacuo. The residue was dissolved in ethyl acetate (30 ml) and 0.5N hydrochloric acid (30 ml). The organic layer was extracted with 1N sodium hydroxide solution (20 ml×3). The combined aqueous extract was acidified to pH 2 with 1N hydrochloric acid and extracted with chloroform (50 ml×3). The extract was washed with brine and dried over magnesium sulfate. Evaporation of the solvent gave benzyl 2(S)-[N-methyl-N-(2-carboxyethyl)aminocarbonyloxy]-3-phenylpropionate (543 mg) as an oil.

Rf: 0.11 (chloroform:methanol:acetic acid, 16:1:1, V/V).

PREPARATION 35

To a mixture of benzyl 2(S)-[N-methyl-N-(2-carboxyethyl)aminocarbonyloxy]-3-phenylpropionate (460 mg) and isobutylamine (143 ml) in anhydrous methylene chloride (10 ml) was added N-ethyl-N'-(3-dimethylaminopropyl)carbodiimide hydrochloride (274 mg) portionwise at 0°-5° C. After being stirred at the same temperature for 3 hours, the solvent was evaporated in vacuo and the residue was dissolved in ethyl acetate (30 ml). The solution was washed with 0.5N hydrochloric acid (30 ml), water (30 ml), aqueous sodium bicarbonate (30 ml), water (30 ml) and brine (30 ml) successively, and dried over magnesium sulfate. Evaporation of the solvent gave benzyl 2(S)-[N-methyl-N-(2-isobutylcarbamoylethyl)aminocarbonyloxy]-3-phenylpropionate (440 mg) as an oil.

Rf: 0.59 (ethyl acetate).

PREPARATION 36

The following compounds were prepared according to a similar manner to that of Preparation 35.

(1) Benzyl 2(S)-[N-{2-(N-methyl-N-phenylcarbamoyl)ethyl}-N-methylaminocarbonyloxy]-3-phenylpropionate (510 mg) from benzyl 2(S)-[N-methyl-N-(2-carboxyethyl)aminocarbonyloxy]-3-phenylpropionate (460 mg) and N-methylaniline (154 mg).

Rf: 0.74 (ethyl acetate).

(2) Benzyl 2(S)-[N-{2-(N-methyl-N-isobutylcarbamoyl)ethyl}-N-methylaminocarbonyloxy]-3-phenylpropionate (586 mg) from benzyl 2(S)-[N-methyl-N-(2-carboxyethyl)aminocarbonyloxy]-3-phenylpropionate (846 mg) and N-methyl-N-isobutylamine (230 mg).

Rf: 0.70 (ethyl acetate).

(3) Benzyl 2(S)-[N-[2-{N-methyl-N-(2-picolyl)carbamoyl}ethyl]-N-methylaminocarbonyloxy]-3-phenylpropionate (941 mg) from benzyl 2(S)-[N-methyl-N-(2-carboxyethyl)aminocarbonyloxy]-3-phenylpropionate (771 mg) and N-methyl-N-(2-picolyl)amine (257 mg).

Rf: 0.26 (ethyl acetate).

(4) Benzyl 2(S)-[N-(2-cyclopentylcarbamoylethyl)-N-methylaminocarbonyloxy]-3-phenylpropionate (534 mg) from benzyl 2(S)-[N-methyl-N-(2-carboxyethyl)aminocarbonyloxy]-3-phenylpropionate (578 mg) and cyclopentylamine (154 mg).

Rf: 0.33 (ethyl acetate).

(5) Benzyl 2(S)-[N-{2-(2-methoxyethylcarbamoyl)ethyl}-N-methylaminocarbonyloxy]-3-phenylpropionate (517 mg) from benzyl 2(S)-[N-methyl-N-(2carboxyethyl)aminocarbonyloxy]-3-phenylpropionate (578 mg) and 2-methoxyethylamine (136 mg).

Rf: 0.60 (ethyl acetate).

(6) Benzyl 2(S)-[N-(2-morpholinocarbamoylethyl)-N-methylaminocarbonyloxy]-3-phenylpropionate (721 mg) from benzyl 2(S)-[N-methyl-N-(2-carboxyethyl)aminocarbonyloxy]-3-phenylpropionate (787 mg) and 4-aminomorpholine (251 mg).

Rf: 0.09 (ethyl acetate).

PREPARATION 37

To a solution of benzyl 2(S)-(3-hydroxypiperidinocarbonyloxy)-3-phenylpropionate (477 mg) in methylene chloride (10 ml) was added pyridinium dichromate (0.99 g) and the mixture was stirred at ambient temperature overnight. The mixture was passed through a Florisil (Trademark: manufactured by Floridin Co.) (60–100 mesh) column with diethyl ether and then methylene chloride as eluent. Concentration under reduced pressure gave benzyl 2(S)-(3-oxopiperidinocarbonyloxy)-3-phenylpropionate (278 mg).

Rf: 0.65 (n-hexane:ethyl acetate, 1:1, V/V).

PREPARATION 38

Benzyl 2(S)-(3-oxopyrrolidine-1-carbonyloxy)-3-phenylpropionate was obtained according to a similar manner to that of Preparation 37.

Rf: 0.55 (n-hexane:ethyl acetate, 1:1, V/V).

PREPARATION 39

To an ice-cooled methylene chloride (3 ml) solution of benzyl 2(S)-[N-(3-isobutylthiopropyl)-N-methylaminocarbonyloxy]-3-phenylpropionate (120 mg) was added m-chloroperbenzoic acid (117 mg) by portions. After the addition was completed, the cooling bath was removed and the reaction mixture was stirred for 4 hours. The solution was diluted with ethyl acetate (20 ml) and washed with 10% aqueous sodium bisulfate (20 ml×2), water (20 ml), saturated aqueous sodium bicarbonate (20 ml×2), water (20 ml) and brine successively, and then dried over magnesium sulfate. Evaporation of the solvent gave benzyl 2(S)-[N-(3-isobutylsulfonylpropyl)-N-methylaminocarbonyloxy]-3-phenylpropionate (145 mg) as an oil.

Rf: 0.15 (n-hexane:ethyl acetate, 1:1, V/V).

PREPARATION 40

Benzyl 2(S)-[N-(2-isopropylsulfonylethyl)-N-methylaminocarbonyloxy]-3-phenylpropionate was obtained according to a similar manner to that of Preparation 39.

Rf: 0.58 (ethyl acetate:n-hexane, 2:1, V/V).

PREPARATION 41

To a solution of benzyl 2(S)-(3-thiazolidinecarbonyloxy)-3-phenylpropionate (371 mg) in methylene chloride (7 ml), which was cooled to 0° C., was added 80% m-chloroperbenzoic acid (215 mg). The mixture was stirred at same temperature for 30 minutes. Then 10% sodium sulfite aqueous solution and methylene chloride were added thereto, and the mixture was separated. The separated aqueous layer was extracted with methylene chloride (2 times). The combined extract was washed with saturated sodium hydrogen carbonate solution and saturated sodium chloride solution successively, dried over magnesium sulfate, and concentrated under reduced pressure. Obtained crystals were washed with n-hexane to give benzyl 2(S)-(1-oxo-thiazolidine-3-carbonyloxy)-3-phenylpropionate (350 mg).

mp: 84°-85° C.
Rf: 0.29 (ethyl acetate).

PREPARATION 42

Benzyl 2(S)-(1-oxothiomorpholinocarbonyloxy)-3-phenylpropionate was obtained according to a similar manner to that of Preparation 41.

mp: 100°-101° C.
Rf: 0.24 (ethyl acetate).

PREPARATION 43

To a solution of benzyl 2(S)-(3-thiazolidinecarbonyloxy)-3-phenylpropionate (371 mg) in methylene chloride (7 ml) was added 80% m-chloroperbenzoic acid (431 mg). The mixture was stirred at ambient temperature for 2 days. Then 10% sodium sulfite aqueous solution and methylene chloride was added thereto, and the mixture was separated. The aqueous layer was extracted with methylene chloride. The combined extract was washed with saturated sodium hydrogen carbonate solution 2 times and saturated sodium chloride solution successively, dried over magnesium sulfate, and concentrated under reduced pressure to give benzyl 2(S)-(1,1-dioxothiazolidine-3-carbonyloxy)-3-phenyl-propionate (330 mg).

mp: 110.5°-111.5° C.
Rf: 0.84 (chloroform:methanol, 9:1, V/V).

PREPARATION 44

Benzyl 2(S)-(1,1-dioxothiomorpholinocarbonyloxy)-3-phenylpropionate was obtained according to a similar manner to that of Preparation 43.

mp: 77°-78° C.
Rf: 0.46 (ethyl acetate:n-hexane, 1:1, V/V).

PREPARATION 45

A solution of benzyl 2(S)-morpholinocarbonyloxy-3-phenylpropionate (300 mg) in methanol (20 ml) was hydrogenated over 10% palladium on carbon (30 mg) at 3 atmospheric pressure of hydrogen for 1 hour. The solution was filtered and concentrated in vacuo to give 2(S)-morpholinocarbonyloxy-3-phenylpropionic acid (220 mg) as an oil.

Rf: 0.59 (chloroform:methanol:acetic acid, 8:1:1, V/V).

PREPARATION 46

A solution of benzyl 2(S)-[N-(2-morpholinocarbonylethyl)-N-methylaminocarbonyloxy]-3-phenylpropionate (726 mg) in methanol (150 ml) and water (10 ml) was hydrogenated over 10% palladium on carbon (80 mg) at 3 atmospheric pressure of hydrogen for 1 hour. The solution was filtered and concentrated in vacuo to give 2(S)-[N-(2-morpholinocarbonylethyl)-N-methylaminocarbonyloxy]-3-phenylpropionic acid (573 mg).

mp: 120°-124° C.
Rf: 0.67 (chloroform:methanol:acetic acid, 8:1:1, V/V).

PREPARATION 47

The following compounds were obtained according to a similar manner to that of Preparation 45 or 46.

(1) 2(S)-(N,N-Diethylaminocarbonyloxy)-3-phenylpropionic acid
Rf: 0.71 (chloroform:methanol:acetic acid, 8:1:1, V/V).

(2) 2(S)-(2-Methoxyethylaminocarbonyloxy)-3-phenylpropionic acid
Rf: 0.55 (chloroform:methanol:acetic acid, 8:1:1, V/V).

(3) 2(S)-(N-Methoxycarbonylmethyl-N-methylaminocarbonyloxy)-3-phenylpropionic acid
Rf: 0.60 (chloroform:methanol:acetic acid, 8:1:1, V/V).

(4) 2(S)-[N-(2-Hydroxyethyl)-N-methylaminocarbonyloxy]-3-phenylpropionic acid
Rf: 0.38 (chloroform:methanol:acetic acid, 16:1:1, V/V).

(5) 2(S)-(N'-Acetyl-N'-methyl-N-methylhydrazinocarbonyloxy)-3-phenylpropionic acid
Rf: 0.64 (chloroform:methanol:acetic acid, 16:1:1, V/V).

(6) 2(S)-(2(S)-Methoxycarbonylpyrrolidine-1-carbonyloxy)-3-phenylpropionic acid
Rf: 0.50 (chloroform:methanol:acetic acid, 16:1:1, V/V).

(7) 2(S)-(N-n-Butyl-N-ethylaminocarbonyloxy)-3-phenylpropionic acid
Rf: 0.49 (chloroform:methanol:acetic acid, 16:1:1, V/V).

(8) 2(S)-(N-Methyl-N-phenethylaminocarbonyloxy)-3-phenylpropionic acid
Rf: 0.52 (chloroform:methanol:acetic acid, 16:1:1, V/V).

(9) 2(S)-(2(R)-Methoxycarbonylpyrrolidine-1-carbonyloxy)-3-phenylpropionic acid
Rf: 0.50 (chloroform:methanol:acetic acid, 16:1:1, V/V).

(10) 2(S)-(N-n-Butyl-N-methylaminocarbonyloxy)-3-phenylpropionic acid
Rf: 0.52 (chloroform:methanol:acetic acid, 16:1:1, V/V).

(11) 2(S)-(N-Methyl-N-phenylaminocarbonyloxy)-3-phenylpropionic acid
Rf: 0.52 (chloroform:methanol:acetic acid, 16:1:1, V/V).

(12) 2(S)-(2(S)-Hydroxymethylpyrrolidine-1-carbonyloxy)-3-phenylpropionic acid
Rf: 0.31 (chloroform:methanol:acetic acid, 16:1:1, V/V).

(13) 2(S)-Hexamethyleneiminocarbonyloxy-3-phenylpropionic acid
Rf: 0.52 (chloroform:methanol:acetic acid, 16:1:1, V/V).

(14) 2(S)-(2(R)-Hydroxymethylpyrrolidine-1-carbonyloxy)-3-phenylpropionic acid
Rf: 0.28 (chloroform:methanol:acetic acid, 16:1:1, V/V).

(15) 2(S)-[N-(1(R)-Morpholinocarbonylethyl)-N-methylaminocarbonyloxy]-3-phenylpropionic acid
Rf: 0.26 (methanol/chloroform, 10%, V/V) 0.75 (chloroform:methanol:acetic acid, 8:1:1, V/V).

(16) 2(S)-[N-(2-Dimethylaminocarbonylethyl)-N-methylaminocarbonyloxy]-3-phenylpropionic acid
mp: 138°-144° C.

Rf: 0.63 (chloroform:methanol:acetic acid, 8:1:1, V/V).

(17) 2(S)-(N-Morpholinocarbonylmethyl-N-methylaminocarbonyloxy)-3-phenylpropionic acid Rf: 0.16 (methanol/chloroform, 10%, V/V) 0.53 (chloroform:methanol:acetic acid, 8:1:1, V/V).

(18) 2(S)-(N-Dimethylaminocarbonylmethyl-N-methylaminocarbonyloxy)-3-phenylpropionic acid Rf: 0.51 (chloroform:methanol:acetic acid, 8:1:1, V/V).

(19) 2(S)-[N-(n-Butylaminocarbonylmethyl)-N-methylaminocarbonyloxy]-3-phenylpropionic acid Rf: 0.53 (chloroform:methanol:acetic acid, 8:1:1, V/V).

(20) 2(S)-[N-(4-Picolylaminocarbonylmethyl)-N-methylaminocarbonyloxy]-3-phenylpropionic acid Rf: 0.08 (chloroform:methanol:acetic acid, 8:1:1, V/V).

(21) 2(S)-[N-(N-Methyl-N-phenethylaminocarbonylmethyl)-N-methylaminocarbonyloxy]-3-phenylpropionic acid Rf: 0.66 (chloroform:methanol:acetic acid, 8:1:1, V/V).

(22) 2(S)-(2(R)-Dimethylaminocarbonylpyrrolidine-1-carbonyloxy)-3-phenylpropionic acid Rf: 0.38 (chloroform:methanol:acetic acid, 8:1:1, V/V).

(23) 2(S)-(6(S)-2-Oxo-1,4-diazabicyclo[4.3.0]nonane-4-carbonyloxy)-3-phenylpropionic acid Rf: 0.44 (chloroform:methanol:acetic acid, 16:1:1, V/V).

(24) 2(S)-(4-Methyl-3-oxopiperazine-1-carbonyloxy)-3-phenylpropionic acid

Rf: 0.25 (chloroform:methanol:acetic acid, 16:1:1, V/V).

(25) 2(S)-(3-Oxopiperazine-1-carbonyloxy)-3-phenylpropionic acid

Rf: 0.30 (chloroform:methanol:acetic acid, 16:1:1, V/V).

(26) 2(S)-(N-Isobutoxycarbonylmethyl-N-methylaminocarbonyloxy)-3-phenylpropionic acid Rf: 0.29 (chloroform:methanol, 10:1, V/V).

(27) 2(S)-(N-Methyl-N-phenethyloxycarbonylmethylaminocarbonyloxy)-3-phenylpropionic acid Rf: 0.31 (chloroform:methanol, 10:1, V/V).

(28) 2(S)-[N-Methyl-N-(5-methyl-2-oxohexyl)aminocarbonyloxy]-3-phenylpropionic acid Rf: 0.18 (chloroform:methanol, 10:1, V/V).

(29) 2(S)-[N-Methyl-N-(2-hydroxy-5-methylhexyl)aminocarbonyloxy]-3-phenylpropionic acid Rf: 0.19 (chloroform:methanol, 10:1, V/V).

(30) 2(S)-[N-Methyl-N-(2-oxopropoxycarbonylmethyl)aminocarbonyloxy]-3-phenylpropionic acid Rf: 0.24 (chloroform:methanol, 10:1, V/V).

(31) 2(S)-[N-{2-(Ethoxycarbonylmethylaminocarbonyl)ethyl}-N-methylaminocarbonyloxy]-3-phenylpropionic acid Rf: 0.14 (chloroform:methanol, 10:1, V/V).

(32) 2(S)-(2(S)-Methoxymethylpyrrolidine-1-carbonyloxy)-3-phenylpropionic acid

Rf: 0.57 (chloroform:methanol:acetic acid, 16:1:1, V/V).

(33) 2(S)-[N-{2-(2-Morpholinoethylaminocarbonyl)ethyl}-N-methylaminocarbonyloxy]-3-phenylpropionic acid Rf: 0.16 (chloroform:methanol:acetic acid, 16:1:1, V/V).

(34) 2(S)-[N-{2-(2-Picolylaminocarbonyl)ethyl}-N-methylaminocarbonyloxy]-3-phenylpropionic acid Rf: 0.31 (chloroform:methanol:acetic acid, 16:1:1, V/V).

(35) 2(S)-[N-[2-[N-{2-(2-Pyridyl)ethyl}-N-methylaminocarbonyl]ethyl]-N-methylaminocarbonyloxy]-3-phenylpropionic acid Rf: 0.31 (chloroform:methanol:acetic acid, 16:1:1, V/V).

(36) 2(S)-[N-{2-(3-Picolylaminocarbonyl)ethyl}-N-methylaminocarbonyloxy]-3-phenylpropionic acid Rf: 0.16 (chloroform:methanol:acetic acid, 16:1:1, V/V).

(37) 2(S)-[N-[2-{N-(2-Pyridyl)-N-methylaminocarbonyl}ethyl]-N-methylaminocarbonyloxy]-3-phenylpropionic acid Rf: 0.34 (chloroform:methanol:acetic acid, 16:1:1, V/V).

(38) 2(S)-[N-(2-Isopropylaminocarbonylethyl)-N-methylaminocarbonyloxy]-3-phenylpropionic acid Rf: 0.40 (chloroform:methanol:acetic acid, 16:1:1, V/V).

(39) 2(S)-[N-{2-(4-Methylpiperazine-1-carbonyl)ethyl}-N-methylaminocarbonyloxy]-3-phenylpropionic acid Rf: 0.12 (chloroform:methanol:acetic acid, 16:1:1, V/V).

(40) 2(S)-(2-Isopropylcarbamoylpyrazolidine-1-carbonyloxy)-3-phenylpropionic acid Rf: 0.54 (chloroform:methanol:acetic acid, 16:1:1, V/V).

(41) 2(S)-[N'-(Methylcarbamoyl)-N,N'-dimethylhydrazinocarbonyloxy]-3-phenylpropionic acid Rf: 0.51 (chloroform:methanol:acetic acid, 16:1:1, V/V).

(42) 2(S)-[N'-(N,N-Dimethylcarbamoyl)-N,N'-dimethylhydrazinocarbonyloxy]-3-phenylpropionic acid Rf: 0.63 (chloroform:methanol:acetic acid, 16:1:1, V/V).

(43) 2(S)-[N'-(Morpholinocarbonyl)-N,N'-dimethylhydrazinocarbonyloxy]-3-phenylpropionic acid Rf: 0.08 (chloroform:methanol, 10:1, V/V).

(44) 2(S)-[N'-(Isopropylcarbamoyl)-N,N'-dimethylhydrazinocarbonyloxy]-3-phenylpropionic acid Rf: 0.53 (chloroform:methanol:acetic acid, 16:1:1, V/V).

(45) 2(S)-[N'-(Benzylcarbamoyl)-N,N'-dimethylhydrazinocarbonyloxy]-3-phenylpropionic acid Rf: 0.40 (ethyl acetate:benzene:acetic acid, 20:20:1, V/V).

(46) 2(S)-(N'-Isobutoxycarbonyl-N,N'-dimethylhydrazinocarbonyloxy)-3-phenylpropionic acid Rf: 0.34 (ethyl acetate:benzene:acetic acid, 20:20:1, V/V).

(47) 2(S)-[N-(2-Hydroxyethyl)-N-ethylaminocarbonyloxy]-3-phenylpropionic acid

Rf: 0.32 (chloroform:methanol:acetic acid, 16:1:1, V/V).

(48) 2(S)-[N-Methyl-N-[2-{N-(morpholinocarbonyl)-N-methylamino}ethyl]aminocarbonyloxy]-3-phenylpropionic acid Rf: 0.33 (chloroform:methanol:acetic acid, 16:1:1, V/V).

(49) 2(S)-[N-Methyl-N-{2-(N-isobutyryl-N-methylamino)ethyl}aminocarbonyloxy]-3-phenylpropionic acid mp: 104°-109° C.

Rf: 0.43 (chloroform:methanol:acetic acid, 16:1:1, V/V).

(50) 2(S)-[N-Methyl-N-{2-(N-isovaleryl-N-methylamino)ethyl}aminocarbonyloxy]-3-phenylpropionic acid
mp: 108°–110° C.
Rf: 0.54 (chloroform:methanol:acetic acid, 16:1:1, V/V).

(51) 2(S)-[N-methyl-N-[4-{N-(morpholinocarbonyl)-N-methylamino}butyl]aminocarbonyloxy]-3-phenylpropionic acid
Rf: 0.21 (chloroform:methanol:acetic acid, 16:1:1, V/V).

(52) 2(S)-[N-{2-(N-Methyl-N-phenylcarbamoyl)ethyl}-methylaminocarbonyloxy]-3-phenylpropionic acid
Rf: 0.25 (chloroform:methanol:acetic acid, 16:1:1, V/V).

(53) 2(S)-[N-{2-(N-Methyl-N-isobutylcarbamoyl)ethyl}-N-methylaminocarbonyloxy]-3-phenylpropionic acid
Rf: 0.35 (chloroform:methanol:acetic acid, 16:1:1, V/V).

(54) 2(S)-[N-(4-Morpholinocarbonylbutyl)-N-methylaminocarbonyloxy]-3-phenylpropionic acid
Rf: 0.27 (chloroform:methanol:acetic acid, 16:1:1, V/V).

(55) 2(S)-(3-Oxopiperidinocarbonyloxy)-3-phenylpropionic acid
Rf: 0.52 (chloroform:methanol:acetic acid, 16:1:1, V/V).

(56) 2(S)-[N-Methyl-N-(2-isobutylcarbamoylethyl)aminocarbonyloxy]-3-phenylpropionic acid
Rf: 0.24 (chloroform:methanol:acetic acid, 16:1:1, V/V).

(57) 2(S)-[N-{4-(N-Methyl-N-isopropylcarbamoyl)butyl}-N-methylaminocarbonyloxy]-3-phenylpropionic acid
Rf: 0.44 (chloroform:methanol:acetic acid, 16:1:1, V/V).

(58) 2(S)-[N-(4-Isopropylcarbamoylbutyl)-N-methylaminocarbonyloxy]-3-phenylpropionic acid
Rf: 0.30 (chloroform:methanol:acetic acid, 16:1:1, V/V).

(59) 2(S)-[N-Methyl-N-[3-{N-(morpholinocarbonyl)-N-methylamino}propyl]aminocarbonyloxy]-3-phenylpropionic acid
Rf: 0.21 (chloroform:methanol, 10:1, V/V).

(60) 2(S)-[N-Methyl-N-(3-morpholinocarbonylpropyl)aminocarbonyloxy]-3-phenylpropionic acid
Rf: 0.18 (chloroform:methanol, 10:1, V/V).

(61) 2(S)-[N-Methyl-N-{3-(N-isopropyl-N-methylcarbamoyl)propyl}aminocarbonyloxy]-3-phenylpropionic acid
Rf: 0.19 (chloroform:methanol, 10:1, V/V).

(62) 2(S)-[N-Methyl-N-{2-(N-t-butoxycarbonyl-N-methylamino)ethyl}aminocarbonyloxy]-3-phenylpropionic acid
Rf: 0.52 (chloroform:methanol:acetic acid, 16:1:1, V/V).

(63) 2(S)-[N-[2-{N-Methyl-N-(2-picolyl)carbamoyl}ethyl]-N-methylaminocarbonyloxy]-3-phenylpropionic acid
Rf: 0.19 (chloroform:methanol:acetic acid, 16:1:1, V/V).

(64) 2(S)-[N-(2-Cyclopentylcarbamoylethyl)-N-methylaminocarbonyloxy]-3-phenylpropionic acid
Rf: 0.30 (chloroform:methanol:acetic acid, 16:1:1, V/V).

(65) 2(S)-[N-{2-(2-Methoxyethylcarbamoyl)ethyl}-N-methylaminocarbonyloxy]-3-phenylpropionic acid
Rf: 0.21 (chloroform:methanol:acetic acid, 16:1:1, V/V).

(66) 2(S)-[N-(2-Morpholinocarbamoylethyl)-N-methylaminocarbonyloxy]-3-phenylpropionic acid
Rf: 0.16 (chloroform:methanol:acetic acid, 16:1:1, V/V).

(67) 2(S)-[N-Methyl-N-[5-{N-(morpholinocarbonyl)-N-methylamino}pentyl]aminocarbonyloxy]-3-phenylpropionic acid
Rf: 0.33 (chloroform:methanol, 10:1, V/V).

(68) 2(S)-[N-Methyl-N-(3-isopropylcarbamoylpropyl)aminocarbonyloxy]-3-phenylpropionic acid
Rf: 0.16 (chloroform:methanol, 10:1, V/V).

(69) 2(S)-[N-Methyl-N-(3-oxo-5-methylhexyl)aminocarbonyloxy]-3-phenylpropionic acid
Rf: 0.17 (chloroform:methanol, 10:1, V/V).

(70) 2(S)-(2-Acetylperhydropyridazine-1-carbonyloxy)-3-phenylpropionic acid
Rf: 0.41 (chloroform:methanol:acetic acid, 16:1:1, V/V).

(71) 2(S)-(2-Butyrylperhydropyridazine-1-carbonyloxy)-3-phenylpropionic acid
Rf: 0.52 (chloroform:methanol:acetic acid, 16:1:1, V/V).

(72) 2(S)-(2-Isobutyrylperhydropyridazine-1-carbonyloxy)-3-phenylpropionic acid
Rf: 0.49 (chloroform:acetic acid:methanol, 16:1:1, V/V).

(73) 2(S)-(2-Benzoylperhydropyridazine-1-carbonyloxy)-3-phenylpropionic acid
Rf: 0.47 (chloroform:methanol:acetic acid, 16:1:1, V/V).

(74) 2(S)-(2-Cyclohexylcarbonylperhydropyridazine-1-carbonyloxy)-3-phenylpropionic acid
Rf: 0.55 (chloroform:methanol:acetic acid, 16:1:1, V/V).

(75) 2(S)-(2-Acetylpyrazolidine-1-carbonyloxy)-3-phenylpropionic acid
Rf: 0.22 (chloroform:methanol:acetic acid, 16:1:1, V/V).

(76) 2(S)-(2-Isobutyrylcarbonylpyrazolidine-1-carbonyloxy)-3-phenylpropionic acid
Rf: 0.36 (chloroform:methanol:acetic acid, 16:1:1, V/V).

(77) 2(S)-(2-Methoxyacetylpyrazolidine-1-carbonyloxy)-3-phenylpropionic acid
Rf: 0.32 (chloroform:methanol:acetic acid, 16:1:1, V/V).

(78) 2(S)-[2-(4-Dimethylaminobutyryl)pyrazolidine-1carbonyloxy]-3-phenylpropionic acid
Rf: 0.17 (chloroform:methanol:acetic acid, 16:1:1, V/V).

(79) 2(S)-(2-Benzoylaminoacetylpyrazolidine-1-carbonyloxy)-3-phenylpropionic acid
Rf: 0.32 (chloroform:methanol:acetic acid, 16:1:1, V/V).

(80) 2(S)-(2-Methylcarbamoylpyrazolidine-1-carbonyloxy)-3-phenylpropionic acid
Rf: 0.48 (chloroform:methanol:acetic acid, 16:1:1, V/V).

(81) 2(S)-(2-Morpholinocarbonylpyrazolidine-1-carbonyloxy)-3-phenylpropionic acid
Rf: 0.21 (chloroform:methanol:acetic acid, 16:1:1, V/V).

(82) 2(S)-[2-(N-t-Butoxycarbonyl-L-leucyl)pyrazolidine-1carbonyloxy]-3-phenylpropionic acid Rf: 0.40 (chloroform:methanol:acetic acid, 16:1:1, V/V).

(83) 2(S)-[2-(N-Acetyl-L-leucyl)pyrazolidine-1-carbonyloxy]-3-phenylpropionic acid Rf: 0.22 (chloroform:methanol:acetic acid, 16:1:1, V/V).

(84) 2(S)-[2-(N$^{\alpha}$-t-Butoxycarbonyl-N$^{im}$-tosyl-L-histidyl)-pyrazolidine-1-carbonyloxy]-3-phenylpropionic acid Rf: 0.16 (chloroform:methanol:acetic acid, 16:1:1, V/V).

(85) 2(S)-(4-Methylpiperazine-1-carbonyloxy)-3-phenylpropionic acid

Rf: 0.18 (chloroform:methanol, 9:1, V/V).

(86) 2(S)-(4-Methylcarbamoylpiperazine-1-carbonyloxy)-3-phenylpropionic acid

Rf: 0.11 (chloroform:methanol:acetic acid, 16:1:1, V/V).

(87) 2(S)-[4-(t-Butoxycarbonylglycyl)piperazine-1-carbonyloxy]-3-phenylpropionic acid Rf: 0.24 (chloroform:methanol, 9:1, V/V).

(88) 2(S)-[4-(Morpholinocarbonyl)piperazine-1-carbonyloxy]-3-phenylpropionic acid Rf: 0.13 (chloroform:methanol:acetic acid, 16:1:1, V/V).

(89) 2(S)-(3-Oxopyrrolidine-1-carbonyloxy)-3-phenylpropionic acid

Rf: 0.46 (chloroform:methanol:acetic acid, 16:1:1, V/V).

(90) 2(S)-(2-Oxazolidinone-3-carbonyloxy)-3-phenylpropionic acid

Rf: 0.15 (chloroform:methanol:acetic acid, 16:1:1, V/V).

(91) 2(S)-(2(R)-Methyl-3(R)-dimethylcarbonylmorpholinocarbonyloxy)-3-phenylpropionic acid Rf: 0.40 (chloroform:methanol:acetic acid, 30:1:1, V/V).

(92) 2(S)-(2(S)-Isobutyl-4-methyl-3-oxopiperazine-1-carbonyloxy)-3-phenylpropionic acid Rf: 0.45 (chloroform:methanol:acetic acid, 30:1:1, V/V).

(93) 2(S)-(6(S)-3(S)-Morpholinocarbonylmethyl-2-oxo-1,4-diazabicyclo[4.3.0]nonane-4-carbonyloxy)-3-phenylpropionic acid Rf: 0.10 (chloroform:methanol, 10:1, V/V).

PREPARATION 48

To a solution of benzyl 2(S)-[N-(2-thiomorpholinocarbonylethyl)-N-methylaminocarbonyloxy]-3-phenylpropionate (418 mg) in methanol (5 ml), which was cooled to 0° C., was added 1N sodium hydroxide aqueous solution (1.33 ml). The mixture was stirred at ambient temperature for one hour. After evaporation of methanol, the residual basic aqueous solution was washed with chloroform (5 ml×2). Then the aqueous solution was acidified to pH 2 with 5% hydrochloric acid, and extracted with ethyl acetate (10 ml×2). The extract was washed with water (10 ml) and saturated sodium chloride solution (10 ml), dried over magnesium sulfate, and concentrated under reduced pressure to give 2(S)-[N-(2-thiomorpholinocarbonylethyl)-N-methylaminocarbonyloxy]-3-phenylpropionic acid (315 g).

Rf: 0.56 (chloroform:methanol:acetic acid, 16:1:1, V/V).

PREPARATION 49

To a solution of benzyl 2(S)-[N-(2-isopropylthioethyl)-N-methylaminocarbonyloxy]-3-phenylpropionate (623 mg) in ethanol (10 ml) was added 1N potassium hydroxide (3 ml) at ambient temperature, and the mixture was stirred at the same temperature for 1 hour. The solution was concentrated in vacuo, and the residue was partitioned between water (20 ml) and diethyl ether (20 ml). The aqueous layer was separated and acidified to pH 2 with 10% hydrochloric acid, and the product was extracted with chloroform (20 ml×2). The extract was washed with water (30 ml) and dried over magnesium sulfate. Evaporation of the solvent gave 2(S)-[N-(2-isopropylthioethyl)-N-methylaminocarbonyloxy]-3-phenylpropionic acid (485 mg).

Rf: 0.84 (chloroform:methanol:acetic acid, 8:1:1, V/V).

PREPARATION 50

The following compounds were obtained according to a similar manner to that of Preparation 48 or 49.

(1) 2(S)-[N-{2-(2-Thiazolylaminocarbonyl)ethyl}-N-methylaminocarbonyloxy]-3-phenylpropionic acid Rf: 0.56 (chloroform:methanol:acetic acid, 16:1:1, V/V).

(2) 2(S)-[N-{2-(1,2,3,6-Tetrahydropyridine-1-carbonyl)ethyl}-N-methylaminocarbonyloxy]-3-phenylpropionic acid Rf: 0.48 (chloroform:methanol:acetic acid, 16:1:1, V/V).

(3) 2(S)-[N-(3-Isobutylthiopropyl)-N-methylaminocarbonyloxy]-3-phenylpropionic acid Rf: 0.38 (chloroform:methanol:acetic acid, 16:1:1, V/V).

(4) 2(S)-[N-(3-Isobutylsulfonylpropyl)-N-methylaminocarbonyloxy]-3-phenylpropionic acid Rf: 0.14 (chloroform:methanol:acetic acid, 16:1:1, V/V).

(5) 2(S)-[N-(2-Isopropylsulfonylethyl)-N-methylaminocarbonyloxy]-3-phenylpropionic acid Rf: 0.58 (chloroform:methanol:acetic acid, 8:1:1, V/V).

(6) 2(S)-(1,2,3,6-Tetrahydropyridine-1-carbonyloxy)-3-phenylpropionic acid

Rf: 0.37 (chloroform:methanol:acetic acid, 16:1:1, V/V).

(7) 2(S)-(3-Thiazolidinecarbonyloxy)-3-phenylpropionic acid

Rf: 0.44 (chloroform:methanol:acetic acid, 16:1:1, V/V).

(8) 2(S)-(1-Oxothiazolidine-3-carbonyloxy)-3-phenylpropionic acid mp: 148.5°-149.5° C.

Rf: 0.17 (chloroform:methanol:acetic acid, 16:1:1, V/V).

(9) 2(S)-(1,1-Dioxothiazolidine-3-carbonyloxy)-3-phenylpropionic acid

Rf: 0.19 (ethyl acetate).

(10) 2(S)-Thiomorpholinocarbonyloxy-3-phenylpropionic acid

Rf: 0.54 (chloroform:methanol:acetic acid, 16:1:1, V/V).

(11) 2(S)-(1-Oxothiomorpholinocarbonyloxy)-3-phenylpropionic acid mp: 162°-163° C.

Rf: 0.19 (chloroform:methanol:acetic acid, 16:1:1, V/V).

(12) 2(S)-(1,1-Dioxothiomorpholinocarbonyloxy)-3-phenylpropionic acid
mp: 92.5°–93.5° C.

PREPARATION 51

(1) To a solution of N-t-butoxycarbonyl-L-cyclohexylalaninal (7.73 g) in dry tetrahydrofuran (200 ml) which was cooled to −78° C., was added dropwise a solution of isopentyl magnesium bromide prepared from isopentyl bromide (46.4 g) and magnesium (7.47 g) in dry tetrahydrofuran (500 ml). After the addition was completed, the reaction mixture was allowed to warm to ambient temperature for 2 hours and was poured into saturated aqueous ammonium chloride (500 ml). The resulting mixture was extracted with ether (500 ml×2), and the extract was combined, dried over magnesium sulfate and evaporated to give an oil (10.1 g). The residue was purified with silica gel (1 kg) column chromatography (10% ethyl acetate in hexane as eluent), to give 2(S)-t-butoxycarbonylamino-1-cyclohexyl-3(S)-hydroxy-6-methylheptane (3.03 g).

Rf: 0.67 (benzene:ethyl acetate, 4:1, V/V).

$[\alpha]_D^{20}$: −23.46° (c 1.0, MeOH).

(2) A solution of 2(S)-t-butoxycarbonylamino-1-cyclohexyl-3(S)-hydroxy-6-methylheptane (600 mg) in trifluoroacetic acid (10 ml) was stirred at 0° C. for 30 minutes. After evaporation of the solvent, the residue was dissolved in ethyl acetate (20 ml). The solution was washed with saturated sodium bicarbonate solution, dried over magnesium sulfate, and evaporated in vacuo to give 2(S)-amino-1-cyclohexyl-3(S)-hydroxy-6-methylheptane (412 mg) as an oil.

Rf: 0.63 (chloroform:methanol:acetic acid, 8:1:1, V/V).

(3) To a solution of $N^\alpha$-t-butoxycarbonyl-$N^\alpha$-methyl-$N^{im}$-tosyl-L-histidine (2.77 g) and 2(S)-amino-1-cyclohexyl-3(S)-hydroxy-6-methylheptane (1.49 g) in dry methylene chloride (60 ml) which was cooled at 0° C., was added N-ethyl-N'-(3-dimethylaminopropyl)carbodiimide (1.25 g). The mixture was stirred at ambient temperature for 3 hours. After evaporation of the solvent, the residue was dissolved in ethyl acetate (200 ml) and the solution was washed with 0.5% hydrochloric acid, saturated sodium bicarbonate solution and water successively, dried over magnesium sulfate, and concentrated under reduced pressure. The residue was purified with silica gel column chromatography (1% methanol in chloroform as eluent) to give 2(S)-($N^\alpha$-t-butoxycarbonyl-$N^\alpha$-methyl-$N^{im}$-tosyl-L-histidyl)amino-1-cyclohexyl-3(S)-hydroxy-6-methylheptane (1.61 g) as an amorphous powder.

mp: 55°–58° C.

Rf: 0.56 (benzene:ethyl acetate:acetic acid, 20:20:1, V/V).

(4) A solution of 2(S)-($N^\alpha$-t-butoxycarbonyl-$N^\alpha$-methyl $N^{im}$-tosyl-L-histidyl)amino-1-cyclohexyl-3(S)-hydroxy-6-methylheptane (1.20 g) in trifluoroacetic acid (20 ml) was stirred at −5° C. for 3 hours. After concentration of the mixture in vacuo, the residue was dissolved in ethyl acetate (100 ml). The solution was washed with saturated sodium bicarbonate solution, dried over magnesium sulfate, and concentrated in vacuo to give 2(S)-($N^\alpha$-methyl-$N^{im}$-tosyl-L-histidyl)amino-1-cyclohexyl-3(S)-hydroxy-6-methylheptane (982 mg) as an oil.

Rf: 0.67 (chloroform:methanol, 10:1, V/V).

PREPARATION 52

(1) A solution of 2(S)-t-butoxycarbonylamino-1-cyclohexyl-3-hydroxy-6-methylheptane (100 g) in hydrogen chloride (58.2 g)/dioxane (400 ml) was stirred at 20° to 30° C. for 1.5 hours. Methylene chloride (500 ml) and water (500 ml) were added thereto and separated aqueous layer was extracted with methylene chloride (300 ml). The organic layers were combined and washed with 5% hydrochloric acid (400 ml), 25% ammonia water (300 ml) and water (300 ml) successively. The solvent was evaporated and the oily residue was dissolved in isopropyl alcohol (420 ml). Said solution was dropwise added to a solution of L-tartaric acid (34.4 g) in water (52 ml) and isopropyl alcohol (570 ml) at 70° to 80° C.

After cooling, the resulting precipitates were collected by filtration and dried to give crude L-tartaric acid salt of 2(S)-amino-1-cyclohexyl-3(S)-hydroxy-6-methylheptane (51.9 g).

mp: 114°–119° C.

$[\alpha]_D^{25}$: −9.5° (c = 1.0, 50% hydrous methanol).

(2) This crude compound (51.9 g) was dissolved in isopropyl alcohol (986 ml) under reflux. The solution was filtered and water (52 ml) was added to the filtrate. After cooling, the resulting precipitates were collected by filtration and dried to give purified L-tartaric acid salt of 2(S)-amino-1-cyclohexyl-3(S)-hydroxy-6-methylheptane (46.7 g).

mp: 119°–122° C.

$[\alpha]_D^{25}$: −10.5° (c = 1.0, 50% hydrous methanol).

(3) To a mixture of purified L-tartaric acid salt of 2(S)-amino-1-cyclohexyl-3(S)-hydroxy-6-methylheptane (46.7 g) and methylene chloride (374 ml) were added 25% ammonia water (140 ml) and water (47 ml). The separated organic layer was washed with water (140 ml) and the solvent was evaporated to give 2(S)-amino-1-cyclohexyl-3(S)-hydroxy-6-methylheptane (28.1 g).

EXAMPLE 1

To a solution of 2(S)-morpholinocarbonyloxy-3-phenylpropionic acid (86 mg) and 2(S)-($N^\alpha$-methyl-$N^{im}$-tosyl-L-histidyl)amino-1-cyclohexyl-3(S)-hydroxy-6-methylheptane (150 mg) in dry methylene chloride (20 ml), which was cooled at 0° C., was added N-ethyl-N'-(3-dimethylaminopropyl)carbodiimide hydrochloride (60 mg). The mixture was stirred at the same temperature for 6 hours. After evaporation of the solvent, the residue was dissolved in ethyl acetate (30 ml). The solution was washed with 5% hydrochloric acid, 1M sodium bicarbonate solution and water successively, dried over sodium sulfate, and concentrated under reduced pressure. After the residue was dissolved in N,N-dimethylformamide (20 ml), pyridine hydrochloride (326 mg) was added to the solution at ambient temperature. The mixture was stirred at the same temperature for 2 hours. After evaporation of the solvent, the residue was dissolved in ethyl acetate (30 ml). The solution was washed with water, 1M sodium bicarbonate solution and water, successively, dried over magnesium sulfate, and concentrated under reduced pressure. The residue was purified with silica gel thin layer chromatography (chloroform:methanol, 8:1, V/V) to give 2(S)-[$N^\alpha$-(2(S)-morpholinocarbonyloxy-3-phenylpropionyl)-$N^\alpha$-methyl-L-histidyl]amino-1-cyclohexyl-3(S)-hydroxy-6-methylheptane (98.2 mg) as an amorphous powder.

mp: 91°–95° C.
Rf: 0.61 (chloroform:methanol, 6:1, V/V).

EXAMPLE 2

To a solution of 2(S)-[N-(2-morpholinocarbonylethyl)-N-methylaminocarbonyloxy]-3-phenylpropionic acid (449 mg) and 2(S)-(N$^\alpha$-methyl-N$^{im}$-tosyl-L-histidyl)amino-1-cyclohexyl-3(S)-hydroxy-6-methylheptane (300 mg) in dry methylene chloride (30 ml), which was cooled to 0° C., was added N-ethyl-N'-(3-dimethylaminopropyl)carbodiimide hydrochloride (140 mg). The mixture was stirred at 5° C. overnight. After evaporation of the solvent, the residue was dissolved in ethyl acetate (30 ml). The solution was washed with 5% hydrochloric acid, 1M sodium bicarbonate solution and water successively, dried over sodium sulfate, and concentrated under reduced pressure. After the residue was dissolved in N,N-dimethylformamide (20 ml), pyridine hydrochloride (650 mg) was added to the solution at ambient temperature. The mixture was stirred at the same temperature for 2 hours. After evaporation of the solvent, the residue was dissolved in ethyl acetate (30 ml). The solution was washed with 1M sodium bicarbonate solution and water successively, dried over magnesium sulfate, and concentrated under reduced pressure. The residue was purified with silica gel thin layer chromatography (chloroform: methanol, 6:1, V/V) to give 2(S)-[N$^\alpha$-[2(S)-{N-(2-morpholinocarbonylethyl)-N-methylaminocarbonyloxy}-3-phenylpropionyl]-N$^\alpha$-methyl-L-histidyl]amino-1-cyclohexyl-3(S)-hydroxy-6-methylheptane (221 mg) as an amorphous powder.
mp: 80°–87° C.
Rf: 0.48 (chloroform:methanol, 6:1, V/V).

EXAMPLE 3

To a solution of 2(S)-[N-methyl-N-[2-{N-(morpholinocarbonyl)-N-methylamino}ethyl]aminocarbonyloxy]-3-phenylpropionic acid (222 mg) in dry methylene chloride (10 ml) which was cooled to 0° C., were added oxalyl chloride (0.051 ml) and three drops of N,N-dimethylformamide. The mixture was stirred at the same temperature for 1 hour. After evaporation of the solvent, the residue was dissolved in dry methylene chloride (5 ml) and the solution was added to a solution of 2(S)-(N$^\alpha$-methyl-N$^{im}$-tosyl-L-histidyl)amino-1-cyclohexyl-3(S)-hydroxy-6-methylheptane (300 mg) and triethylamine (57 mg) in methylene chloride (10 ml) at 0° C. The mixture was stirred at the same temperature for 3 hours. After evaporation of the solvent, the residue was dissolved in ethyl acetate (30 ml) and the solution was washed with 5% hydrochloric acid, 1M sodium bicarbonate solution, and water successively, dried over magnesium sulfate, and concentrated under reduced pressure. After the residue was dissolved in N,N-dimethylformamide (10 ml), pyridine hydrochloride (650 mg) was added to the solution at ambient temperature. The mixture was stirred at the same temperature for 2 hours. After evaporation of the solvent, the residue was dissolved in ethyl acetate (30 ml) and the solution was washed with 1M sodium bicarbonate solution and water successively, dried over magnesium sulfate, and concentrated in vacuo. The residue was purified with silica gel thin layer chromatography (chloroform:methanol, 9:1, V/V) to give 2(S)-[N$^\alpha$-[2(S)-[N-methyl-N-[2-{N-(morpholinocarbonyl)-N-methylamino}ethyl]aminocarbonyloxy]-3-phenylpropionyl]-N$^\alpha$-methyl-L-histidyl]amino-1-cyclohexyl-3(S)-hydroxy-6-methylheptane (297 mg) as an amorphous powder.
mp: 69°–74° C.
Rf: 0.45 (chloroform:methanol, 10:1, V/V).

EXAMPLE 4

To a solution of 2(S)-[N-methyl-N-{2-(N-isobutyryl-N-methylamino)ethyl}aminocarbonyloxy]-3-phenylpropionic acid (217 mg) in dry methylene chloride (20 ml) which was cooled to 0° C., were added oxalyl chloride (0.054 ml) and three drops of N,N-dimethylformamide. The mixture was stirred at the same temperature for 1 hour. After evaporation of the solvent, the residue was dissolved in dry methylene chloride (5 ml) and the solution was added to a solution of 2(S)-(N$^\alpha$-methyl-N$^{im}$-tosyl-L-histidyl)amino-1-cyclohexyl-3(S)-hydroxy-6-methyl heptane (300 mg) and triethylamine (63 mg) in methylene chloride (10 ml) at 0° C. The mixture was stirred at the same temperature for 3 hours. After evaporation of the solvent, the residue was dissolved in ethyl acetate (30 ml) and the solution was wahsed with 5% hydrochloric acid, 1M sodium bicarbonate solution and water successively, dried over magnesium sulfate, and concentrated under reduced pressure. After the residue was dissolved in N,N-dimethylformamide (15 ml), pyridine hydrochloride (650 mg) was added thereto at ambient temperature. The mixture was stirred at the same temperature for 2 hours. After evaporation of the solvent the residue was dissolved in ethyl acetate (30 ml) and the solution was washed with 1M sodium bicarbonate solution and water successively, dried over magnesium sulfate, and concentrated in vacuo. The residue was purified with silica gel thin layer chromatography (chloroform:methanol, 9:1, V/V) to give 2(S)-[N$^\alpha$-[2(S)-[N-methyl-N-{2-(N-isobutyryl-N-methylamino)ethyl}aminocarbonyloxy]-3-phenylpropionyl]-N$^\alpha$-methyl-L-histidyl]-amino-1-cyclohexyl-3(S)-hydroxy-6-methylheptane (295 mg) as an amorphous powder.
mp: 68°–72° C.
Rf: 0.46 (chloroform:methanol, 10:1, V/V).

EXAMPLE 5

The following compounds were obtained according to a similar manner to that of Examples 1 to 4.
(1) 2(S)-[N$^\alpha$-{2(S)-(N,N-Diethylaminocarbonyloxy)-3-phenylpropionyl}-N$^\alpha$-methyl-L-histidyl]amino-1-cyclohexyl-3(S)-hydroxy-6-methylheptane
mp: 75°–79° C.
Rf: 0.61 (chloroform:methanol, 6:1, V/V).
(2) 2(S)-[N$^\alpha$-{2(S)-(2-Methoxyethylaminocarbonyloxy)-3-phenylpropionyl}-N$^\alpha$-methyl-L-histidyl]amino-1-cyclohexyl-3(S)-hydroxy-6-methylheptane
mp: 80°–84° C.
Rf: 0.45 (chloroform:methanol, 6:1, V/V).
(3) 2(S)-[N$^\alpha$-{2(S)-(N-Methoxycarbonylmethyl-N-methylaminocarbonyloxy)-3-phenylpropionyl}-N$^\alpha$-methyl-L-histidyl]amino-1-cyclohexyl-3(S)-hydroxy-6-methylheptane
mp: 84°–87° C.
Rf: 0.55 (chloroform:methanol, 6:1, V/V).
(4) 2(S)-[N$^\alpha$-[2(S)-{N-(2-Hydroxyethyl)-N-methylaminocarbonyloxy}-3-phenylpropionyl]-N$^\alpha$-methyl-L-histidyl]-amino-1-cyclohexyl-3(S)-hydroxy-6-methylheptane
mp: 82°–86° C.
Rf: 0.57 (chloroform:methanol, 6:1, V/V).
(5) 2(S)-[N$^\alpha$-{2(S)-(N'-Acetyl-N'-methyl-N-methylhydrazinocarbonyloxy)-3-phenylpropionyl}-N$^\alpha$-methyl-L-histidyl]amino-1-cyclohexyl-3(S)-hydroxy-6-methylheptane
mp: 88°–92° C.
Rf: 0.68 (chloroform:methanol, 6:1, V/V).

(6) 2(S)-[N$^\alpha$-{2(S)-(2(S)-Methoxycarbonylpyrrolidine-1-carbonyloxy)-3-phenylpropionyl}-N$^\alpha$-methyl-L-histidyl]amino-1-cyclohexyl-3(S)-hydroxy-6-methylheptane
mp: 71°–76° C.
Rf: 0.31 (chloroform:methanol, 10:1, V/V).

(7) 2(S)-[N$^\alpha$-{2(S)-(N-n-Butyl-N-ethylaminocarbonyloxy)-3-phenylpropionyl}-N$^\alpha$-methyl-L-histidyl]amino-1-cyclohexyl-3(S)-hydroxy-6-methylheptane
mp: 67°–71° C.
Rf: 0.27 (chloroform:methanol, 10:1, V/V).

(8) 2(S)-[N$^\alpha$-{2(S)-(N-Methyl-N-phenethylaminocarbonyloxy)-3-phenylpropionyl}-N$^\alpha$-methyl-L-histidyl]amino-1-cyclohexyl-3(S)-hydroxy-6-methylheptane
mp: 66°–69° C.
Rf: 0.30 (chloroform:methanol, 10:1, V/V).

(9) 2(S)-[N$^\alpha$-{2(S)-(2(R)-Methoxycarbonylpyrrolidine-1-carbonyloxy)-3-phenylpropionyl}-N$^\alpha$-methyl-L-histidyl]amino-1-cyclohexyl-3(S)-hydroxy-6-methylheptane
mp: 73°–79° C.
Rf: 0.41 (chloroform:methanol, 10:1, V/V).

(10) 2(S)-]N$^\alpha$-{2(S)-(N-n-Butyl-N-methylaminocarbonyloxy)-(3-phenylpropionyl)-N$^\alpha$-methyl-L-histidyl]amino-1-cyclohexyl-3(S)-hydroxy-6-methylheptane
mp: 67°–71° C.
Rf: 0.40 (chloroform:methanol, 10:1, V/V).

(11) 2(S)-[N$^\alpha$-{2(S)-(N-Methyl-N-phenylaminocarbonyloxy)-3-phenylpropionyl}-N$^\alpha$-methyl-L-histidyl]amino-1-cyclohexyl-3(S)-hydroxy-6-methylheptane
mp: 83°–87° C.
Rf: 0.38 (chloroform:methanol, 10:1, V/V).

(12) 2(S)-[N$^\alpha$-{2(S)-(2(S)-Hydroxymethylpyrrolidine-1-carbonyloxy)-3-phenylpropionyl}-N$^\alpha$-methyl-L-histidyl]amino-1-cyclohexyl-3(S)-hydroxy-6-methylheptane
mp: 94°–101° C.
Rf: 0.29 (chloroform:methanol, 10:1, V/V).

(13) 2(S)-[N$^\alpha$-(2(S)-Hexamethyleneiminocarbonyloxy-3-phenylpropionyl)-N$^\alpha$-methyl-L-histidyl]amino-1-cyclohexyl-3(S)-hydroxy-6-methylheptane
mp: 71°–77° C.
Rf: 0.36 (chloroform:methanol, 10:1, V/V).

(14) 2(S)-[N$^\alpha$-{2(S)-(2(R)-Hydroxymethylpyrrolidine-1-carbonyloxy)-3-phenylpropionyl}-N$^\alpha$-methyl-L-histidyl]-amino-1-cyclohexyl-3(S)-hydroxy-6-ethylheptane
mp: 93°–99° C.
Rf: 0.30 (chloroform:methanol, 10:1, V/V).

(15) 2(S)-[N$^\alpha$-[2(S)-{N-(1(R)-Morpholinocarbonylethyl)-N-methylaminocarbonyloxy}-3-phenylpropionyl]-N$^\alpha$-methyl-L-histidyl]amino-1-cyclohexyl-3(S)-hydroxy-6-methylheptane
mp: 92°–97° C.
Rf: 0.42 (chloroform:methanol, 6:1, V/V).

(16) 2(S)-[N$^\alpha$-[2(S)-{N-(2-Dimethylaminocarbonylethyl)-N-methylaminocarbonyloxy}-3-phenylpropionyl]-N$^\alpha$-methyl-L-histidyl]amino-1-cyclohexyl-3(S)-hydroxy-6-methylheptane
mp: 55°–60° C.
Rf: 0.39 (chloroform:methanol, 6:1, V/V).

(17) 2(S)-[N$^\alpha$-{2(S)-(N-Morpholinocarbonylmethyl-N-methylaminocarbonyloxy)-3-phenylpropionyl}-N$^\alpha$-methyl-L-histidyl]amino-1-cyclohexyl-3(S)-hydroxy-6-methylheptane
mp: 91°–94° C.
Rf: 0.49 (chloroform:methanol, 6:1, V/V).

(18) 2(S)-[N$^\alpha$-{2(S)-(N-Dimethylaminocarbonylmethyl-N-methylaminocarbonyloxy)-3-phenylpropionyl}-N$^\alpha$-methyl-L-histidyl]amino-1-cyclohexyl-3(S)-hydroxy-6-methylheptane
mp: 79°–83° C.
Rf: 0.40 (chloroform:methanol, 6:1, V/V).

(19) 2(S)-[N$^\alpha$-[2(S)-{N-(n-Butylaminocarbonylmethyl)-N-methylaminocarbonyloxy}-3-phenylpropionyl]-N$^\alpha$-methyl-L-histidyl]amino-1-cyclohexyl-3(S)-hydroxy-6-methylheptane
mp: 77°–81° C.
Rf: 0.55 (chloroform:methanol, 6:1, V/V).

(20) 2(S)-[N$^\alpha$-[2(S)-{N-(4-Picolylaminocarbonylmethyl)-N-methylaminocarbonyloxy}-3-phenylpropionyl]-N$^\alpha$-methyl-L-histidyl]amino-1-cyclohexyl-3(S)-hydroxy-6-methylheptane
mp: 80°–89° C.
Rf: 0.36 (chloroform:methanol, 6:1, V/V).

(21) 2(S)-[N$^\alpha$-[2(S)-{N-(N-Methyl-N-phenethylaminocarbonylmethyl)-N-methylaminocarbonyloxy}-3-phenylpropionyl]-N$^\alpha$-methyl-L-histidyl]amino-1-cyclohexyl-3(S)-hydroxy-6-methylheptane
mp: 72°–80° C.
Rf: 0.42 (chloroform:methanol, 6:1, V/V).

(22) 2(S)-[N$^\alpha$-{2(S)-(2(R)-Dimethylaminocarbonylpyrrolidine-1-carbonyloxy)-3-phenylpropionyl}-N$^\alpha$-methyl-L-histidyl]amino-1-cyclohexyl-3(S)-hydroxy-6-methylheptane
mp: 100°–102° C.
Rf: 0.70 (chloroform:methanol, 6:1, V/V).

(23) 2(S)-[N$^\alpha$-{2(S)-(6(S)-2-Oxo-1,4-diazabicyclo[4.3.0]-nonane-4-carbonyloxy)-3-phenylpropionyl}-N$^\alpha$-methyl-L-histidyl]amino-1-cyclohexyl-3(S)-hydroxy-6-methylheptane
mp: 91°–96° C.
Rf: 0.42 (methanol/chloroform, 10%, V/V).

(24) 2(S)-[N$^\alpha$-{2(S)-(4-Methyl-3-oxopiperazine-1-carbonyloxy)-3-phenylpropionyl}-N$^\alpha$-methyl-L-histidyl]amino-1-cyclohexyl-3(S)-hydroxy-6-methylheptane
mp: 81°–85° C.
Rf: 0.38 (chloroform:methanol, 10:1, V/V).

(25) 2(S)-[N$^\alpha$-{2(S)-(3-Oxopiperazine-1-carbonyloxy)-3-phenylpropionyl}-N$^\alpha$-methyl-L-histidyl]amino-1-cyclohexyl-3(S)-hydroxy-6-methylheptane
mp: 108°–112° C.
Rf: 0.48 (chloroform:methanol, 10:1, V/V).

(26) 2(S)-[N$^\alpha$-{2(S)-(N-Isobutoxycarbonylmethyl-N-methylaminocarbonyloxy)-3-phenylpropionyl}-N$^\alpha$-methyl-L-histidyl]amino-1-cyclohexyl-3(S)-hydroxy-6-methylheptane
mp: 58°–60° C.
Rf: 0.62 (chloroform:methanol, 10:1, V/V).

(27) 2(S)-[N$^\alpha$-{2(S)-(N-Methyl-N-phen-ethyloxycarbonylmethylaminocarbonyloxy)-3-phenylpropionyl}-N$^\alpha$-methyl-L-histidyl]amino-1-cyclohexyl-3(S)-hydroxy-6-methylheptane
mp: 54°–57° C.
Rf: 0.64 (chlorform:methanol, 10:1, V/V).

(28) 2(S)-[N$^\alpha$-[2(S)-{N-Methyl-N-(5-methyl-2-oxohexyl)aminocarbonyloxy}-3-phenylpropionyl]-N$^\alpha$--methyl-L-histidyl]amino-1-cyclohexyl-3(S)-hydroxy-6-methylheptane
mp: 65°–67° C.

Rf: 0.38 (chloroform:methanol, 10:1, V/V).

(29) 2(S)-[N$^\alpha$-[2(S)-{N-Methyl-N-(2-hydroxy-5-methylhexyl)aminocarbonyloxy}-3-phenylpropionyl]-N$^\alpha$-methyl-L-histidyl]amino-1-cyclohexyl-3(S)-hydroxy-6-methylheptane mp: 76°–78° C.

Rf: 0.24 (chloroform:methanol, 10:1, V/V).

(30) 2(S)-[N$^\alpha$-[2(S)-{N-Methyl-N-(2-oxopropoxycarbonylmethyl)aminocarbonyloxy}-3-phenylpropionyl]-N$^\alpha$-methyl-L-histidyl]amino-1-cyclohexyl-3(S)-hydroxy-6-methylheptane mp: 65°–68° C.

Rf: 0.78 (chloroform:methanol, 10:1, V/V).

(31) 2(S)-[N$^\alpha$-[2(S)-[N-{2-(Ethoxycarbonylmethylaminocarbonyl)ethyl}-N-methylaminocarbonyloxy]-3-phenylpropionyl]-N$^\alpha$-methyl-L-histidyl]amino-1-cyclohexyl-3(S)-hydroxy-6-methylheptane mp: 72°–75° C.

Rf: 0.44 (chloroform:methanol, 10:1, V/V).

(32) 2(S)-[N$^\alpha$-{2(S)-(2(S)-Methoxymethylpyrrolidine-1-carbonyloxy)-3-phenylpropionyl}-N$^\alpha$-methyl-L-histidyl]amino-1-cyclohexyl-3(S)-hydroxy-6-methylheptane mp: 72°–77° C.

Rf: 0.44 (chloroform:methanol, 9:1, V/V).

(33) 2(S)-[N$^\alpha$-[2(S)-[N-{2-(2-Morpholinoethylaminocarbonyl)ethyl}-N-methylaminocarbonyloxy]-3-phenylpropionyl]-N$^\alpha$-methyl-L-histidyl]amino-1-cyclohexyl-3(S)-hydroxy-6-methylheptane mp: 60°–64° C.

Rf: 0.26 (chloroform:methanol, 9:1, V/V).

(34) 2(S)-[N$^\alpha$-[2(S)-[N-{2-(2-Picolylaminocarbonyl)ethyl}-N-methylaminocarbonyloxy]-3-phenylpropionyl]-N$^\alpha$-methyl-L-histidyl]amino-1-cyclohexyl-3(S)-hydroxy-6-methylheptane mp: 64°–68° C.

Rf: 0.40 (chloroform:methanol, 9:1, V/V).

(35) 2(S)-[N$^\alpha$-[2(S)-[N-[2-[N-{2-(2-Pyridyl)ethyl}-N--methylaminocarbonyl]ethyl]-N-methylaminocarbonyloxy]-3-phenylpropionyl]-N$^\alpha$-methyl-L-histidyl]amino-1-cyclohexyl-3(S)-hydroxy-6-methylheptane mp: 55°–58° C.

Rf: 0.17 (chloroform:methanol, 9:1, V/V).

(36) 2(S)-[N$^\alpha$-[2(S)-[N-{2-(3-Picolylaminocarbonyl)ethyl}-N-methylaminocarbonyloxy]-3-phenylpropionyl]-N$^\alpha$-methyl-L-histidyl]amino-1-cyclohexyl-3(S)-hydroxy-6-methylheptane mp: 67°–71° C.

Rf: 0.44 (chloroform:methanol, 9:1, V/V).

(37) 2(S)-[N$^\alpha$-[2(S)-[N-[2-{N-(2-Pyridyl)-N-methylaminocarbonyl}ethyl]-N-methylaminocarbonyloxy]-3-phenylpropionyl]-N$^\alpha$-methyl-L-histidyl]amino-1-cyclohexyl-3(S)-hydroxy-6-methylheptane mp: 73°–77° C.

Rf: 0.27 (chloroform:methanol, 9:1, V/V).

(38) 2(S)-[N$^\alpha$-[2(S)-{N-(2-Isopropylaminocarbonylethyl)-N-methylaminocarbonyloxy}-3-phenylpropionyl]-N$^\alpha$-methyl-L-histidyl]amino-1-cyclohexyl-3(S)-hydroxy-6-methylheptane mp: 78°–83° C.

Rf: 0.49 (chloroform:methanol, 9:1, V/V).

(39) 2(S)-[N$^\alpha$-[2(S)-[N-{2-(4-Methylpiperazine-1-carbonyl)-ethyl}-N-methylaminocarbonyloxy]-3-phenylpropyl]-N$^\alpha$-methyl-L-histidyl]amino-1-cyclohexyl-3(S)-hydroxy-6-methylheptane mp: 65°–71° C.

Rf: 0.17 (chloroform:methanol, 9:1, V/V).

(40) 2(S)-[N$^\alpha$-[2(S)-{N-(2-Thiomorpholinocarbonylethyl)-N-methylaminocarbonyloxy}-3-phenylpropionyl]-N$^\alpha$-methyl-L-histidyl]amino-1-cyclohexyl-3(S)-hydroxy-6-methylheptane mp: 66°–72° C.

Rf: 0.45 (chloroform:methanol, 9:1, V/V).

(41) 2(S)-[N$^\alpha$-[2(S)-[N-{2-(2-Thiazolylaminocarbonyl)-ethyl}-N-methylaminocarbonyloxy]-3-phenylpropionyl]-N$^\alpha$-methyl-L-histidyl]amino-1-cyclohexyl-3(S)-hydroxy-6-methylheptane mp: 100°–106° C.

Rf: 0.45 (chloroform:methanol, 9:1, V/V).

(42) 2(S)-[N$^\alpha$-[2(S)-[N-{2-(1,2,3,6-Tetrahydropyridine-1-carbonyl)ethyl}-N-methylaminocarbonyloxy]-3-phenylpropionyl]-N$^\alpha$-methyl-L-histidyl]amino-1-cyclohexyl-3(S)-hydroxy-6-methylheptane mp: 67°–73° C.

Rf: 0.48 (chloroform:methanol, 9:1, V/V).

(43) 2(S)-[N$^\alpha$-{2(S)-(2-Isopropylcarbamoylpyrazolidine-1-carbonyloxy)-3-phenylpropionyl}-N$^\alpha$-methyl-L-histidyl]amino-1-cyclohexyl-3(S)-hydroxy-6-methylheptane mp: 86°–89° C.

Rf: 0.46 (chloroform:methanol, 9:1, V/V).

(44) 2(S)-[N$^\alpha$-[2(S)-{N'-(Methylcarbamoyl-N,N'-dimethylhydrazinocarbonyloxy}-3-phenylpropionyl]-N-methyl-L-histidyl]amino-1-cyclohexyl-3(S)-hydroxy-6-methylheptane mp: 112°–116° C.

Rf: 0.50 (chloroform:methanol, 10:1, V/V).

(45) 2(S)-[N$^\alpha$-[2(S)-{N'-(N,N-Dimethylcarbamoyl)-N,N'-dimethylhydrazinocarbonyloxy}-3-phenylpropionyl]-N$^\alpha$-methyl-L-histidyl]amino-1-cyclohexyl-3(S)-hydroxy-6-methylheptane mp: 75°–79° C.

Rf: 0.54 (chloroform:methanol, 6:1, V/V).

(46) 2(S)-[N$^\alpha$-[2(S)-{N'-(Morpholinocarbonyl)-N,N'-dimethylhydrazinocarbonyloxy}-3-phenylpropionyl]-N$^\alpha$-methyl-L-histidyl]amino-1-cyclohexyl-3(S)-hydroxy-6-methylheptane mp: 86°–92° C.

Rf: 0.42 (chloroform:methanol, 10:1, V/V).

(47) 2(S)-[N$^\alpha$-[2(S)-{N'-(Isopropylcarbamoyl)-N,N'-dimethylhydrazinocarbonyloxy}-3-phenylpropionyl]-N$^\alpha$-methyl-L-histidyl]amino-1-cyclohexyl-3(S)-hydroxy-6-methylheptane mp: 94°–99° C.

Rf: 0.54 (chloroform:methanol, 6:1, V/V).

(48) 2(S)-[N$^\alpha$-[2(S)-{N'-(Benzylcarbamoyl)-N,N'-dimethylhydrazinocarbonyloxy}-3-phenylpropionyl]-N$^\alpha$-methyl-L-histidyl]amino-1-cyclohexyl-3(S)-hydroxy-6-methylheptane mp: 99°–104° C.

Rf: 0.31 (chloroform:methanol, 6:1, V/V).

(49) 2(S)-[N$^\alpha$-{2(S)-(N'-Isobutoxycarbonyl-N,N'-dimethylhydrazinocarbonyloxy)-3-phenylpropionyl}-N$^\alpha$-methyl-L-histidyl]amino-1-cyclohexyl-3(S)-hydroxy-6-methylheptane mp: 74°–77° C.

Rf: 0.24 (chloroform:methanol, 10:1, V/V).

(50) 2(S)-[N$^\alpha$-[2(S)-{N-(2-Hydroxyethyl)-N-ethylaminocarbonyloxy}-3-phenylpropionyl]-N$^\alpha$-methyl-L-histidyl]amino-1-cyclohexyl-3(S)-hydroxy-6-methylheptane mp: 80°–84° C.

Rf: 0.53 (chloroform:methanol, 6:1, V/V).

(51) 2(S)-[N$^\alpha$-[2(S)-[N-Methyl-N-{2-(N-isovaleryl-N-methylamino)ethyl}aminocarbonyloxy]-3-phenylpropionyl]-N$^\alpha$-methyl-L-histidyl]amino-1-cyclohexyl-3(S)-hydroxy-6-methylheptane mp: 68°–72° C.

Rf: 0.44 (chloroform:methanol, 10:1, V/V).

(52) 2(S)-[N$^\alpha$-[2(S)-[N-Methyl-N-[4-{N-(morpholinocarbonyl)-N-methylamino}butyl]aminocarbonyloxy]-3-phenylpropionyl]-N$^\alpha$-methyl-L-histidyl]amino-1-cyclohexyl-3(S)-hydroxy-6-methylheptane mp: 64°–67° C.

Rf: 0.35 (chloroform:methanol, 10:1, V/V).

(53) 2(S)-[N$^\alpha$-[2(S)-[N-{2-(N-Methyl-N-phenylcarbamoyl)-ethyl}-N-methylaminocarbonyloxy]-3-phenylpropionyl]-N$^\alpha$-methyl-L-histidyl]amino-1-cyclohexyl-3(S)-hydroxy-6-methylheptane mp: 67°–71° C.

Rf: 0.47 (chloroform:methanol, 9:1, V/V).

(54) 2(S)-[N$^\alpha$-[2(S)-[N-{2-(N-Methyl-N-isobutylcarbamoyl)-ethyl}-N-methylaminocarbonyloxy]-3-phenylpropionyl]-N$^\alpha$-methyl-L-histidyl]amino-1-cyclohexyl-3(S)-hydroxy-6-methylheptane mp: 73°–79° C.

Rf: 0.50 (chloroform:methanol, 9:1, V/V).

(55) 2(S)-[N$^\alpha$-[2(S)-{N-(4-Morpholinocarbonylbutyl)-N-methylaminocarbonyloxy}-3-phenylpropionyl]-N$^\alpha$-methyl-L-histidyl]amino-1-cyclohexyl-3(S)-hydroxy-6-methylheptane mp: 72°–78° C.

Rf: 0.48 (chloroform:methanol, 9:1, V/V).

(56) 2(S)-[N$^\alpha$-{2(S)-(3-Oxopiperidinocarbonyloxy)-3-phenylpropionyl}-N$^\alpha$-methyl-L-histidyl]amino-1-cyclohexyl-3(S)-hydroxy-6-methylheptane mp: 86°–90° C.

Rf: 0.41 (chloroform:methanol, 9:1, V/V).

(57) 2(S)-[N$^\alpha$-[2(S)-[N-Methyl-N-(2-isobutylcarbamoylethyl)aminocarbonyloxy]-3-phenylpropionyl]-N$^\alpha$-methyl-L-histidyl]amino-1-cyclohexyl-3(S)-hydroxy-6-methylheptane mp: 79°–83° C.

Rf: 0.54 (chloroform:methanol, 9:1, V/V).

(58) 2(S)-[N$^\alpha$-[2(S)-[N-{4-(N-Methyl-N-isopropylcarbamoyl)butyl}-N-methylaminocarbonyloxy]-3-phenylpropionyl]-N$^\alpha$-methyl-L-histidyl]amino-1-cyclohexyl-3(S)-hydroxy-6-methylheptane mp: 64°–71° C.

Rf: 0.46 (chloroform:methanol, 9:1, V/V).

(59) 2(S)-[N$^\alpha$-[2(S)-{N-(4-Isopropylcarbamoylbutyl)-N-methylaminocarbonyloxy}-3-phenylpropionyl]-N$^\alpha$-methyl-L-histidyl]amino-1-cyclohexyl-3(S)-hydroxy-6-methylheptane mp: 74°–80° C.

Rf: 0.41 (chloroform:methanol, 9:1, V/V).

(60) 2(S)-[N$^\alpha$-[2(S)-[N-Methyl-N-[3-{N-(morpholinocarbonyl)-N-methylamino}propyl]aminocarbonyloxy]-3-phenylpropionyl]-N$^\alpha$-methyl-L-histidyl]amino-1-cyclohexyl-3(S)-hydroxy-6-methylheptane mp: 62°–66° C.

Rf: 0.51 (chloroform:methanol, 10:1, V/V).

(61) 2(S)-[N$^\alpha$-[2(S)-{N-Methyl-N-(3-morpholinocarbonylpropyl)aminocarbonyloxy}-3-phenylpropionyl]-N$^\alpha$-methyl-L-histidyl]amino-1-cyclohexyl-3(S)-hydroxy-6-methylheptane mp: 60°–63° C.

Rf: 0.39 (chloroform:methanol, 10:1, V/V).

(62) 2(S)-[N$^\alpha$-[2(S)-[N-Methyl-N-{3-(N-isopropyl-N-methylcarbamoyl)propyl}aminocarbonyloxy]-3-phenylpropionyl]-N$^\alpha$-methyl-L-histidyl]amino-1-cyclohexyl-3(S)-hydroxy-6-methylheptane mp: 70°–73° C.

Rf: 0.41 (chloroform:methanol, 10:1, V/V).

(63) 2(S)-[N$^\alpha$-[2(S)-[N-Methyl-N-{2-(N-t-butoxycarbonyl-N-methylamino)ethyl}aminocarbonyloxy]-3-phenylpropionyl]-N$^\alpha$-methyl-L-histidyl]amino-1-cyclohexyl-3(S)-hydroxy-6-methylheptane mp: 61°–65° C.

Rf: 0.50 (chloroform:methanol, 10:1, V/V).

(64) 2(S)-[N$^\alpha$-[2(S)-[N-[2-{N-Methyl-N-(2-picolyl)-carbamoyl}ethyl]-N-methylaminocarbonyloxy]-3-phenylpropionyl]-N$^\alpha$-methyl-L-histidyl]amino-1-cyclohexyl-3(S)-hydroxy-6-methylheptane

65°–69° C.

Rf: 0.48 (chloroform:methanol, 9:1, V/V).

(65) 2(S)-[N$^\alpha$-[2(S)-{N-(2-Cyclopentylcarbamoylethyl)-N-methylaminocarbonyloxy}-3-phenylpropionyl]-N$^\alpha$-methyl-L-histidyl]amino-1-cyclohexyl-3(S)-hydroxy-6-methylheptane mp: 86°–92° C.

Rf: 0.68 (chloroform:methanol, 9:1, V/V).

(66) 2(S)-[N$^\alpha$-[2(S)-[N-{2-(2-Methoxyethylcarbamoyl)ethyl}-N-methylaminocarbonyloxy]-3-phenylpropionyl]-N$^\alpha$-methyl-L-histidyl]amino-1-cyclohexyl-3(S)-hydroxy-6-methylheptane mp: 68°–74° C.

Rf: 0.40 (Chloroform:methanol, 9:1, V/V).

(67) 2(S)-[N$^\alpha$-[2(S)-{N-(2-Morpholinocarbamoylethyl)-N-methylaminocarbonyloxy}-3-phenylpropionate-N$^\alpha$-methyl-L-histidyl]amino-1-cyclohexyl-3(S)-hydroxy-6-methylheptane mp: 92°–98° C.

Rf: 0.39 (chloroform:methanol, 9:1, V/V).

(68) 2(S)-[N$^\alpha$-[2(S)-{N-(3-Isobutylthiopropyl)-N-methylaminocarbonyloxy}-3-phenylpropionyl]-N$^\alpha$-methyl-L-histidyl]amino-1-cyclohexyl-3(S)-hydroxy-6-methylheptane mp: 62°–68° C.

Rf: 0.53 (chloroform:methanol, 9:1, V/V).

(69) 2(S)-[N$^\alpha$-[2(S)-{N-(3-Isobutylsulfonylpropyl)-N-methylaminocarbonyloxy}-3-phenylpropionyl]-N$^\alpha$-methyl-L-histidyl]amino-1-cyclohexyl-3(S)-hydroxy-6-methylheptane mp: 77°–82° C.

Rf: 0.57 (chloroform:methanol, 9:1, V/V).

(70) 2(S)-[N$^\alpha$-[2(S)-[N-Methyl-N-[5-{N-(morpholinocarbonyl)-N-methylamino}pentyl]aminocarbonyloxy]-3-phenylpropionyl]-N$^\alpha$-methyl-L-histidyl]amino-1-cyclohexyl-3(S)-hydroxy-6-methylheptane mp: 58°–61° C.

Rf: 0.33 (chloroform:methanol, 10:1, V/V).

(71) 2(S)-[N$^\alpha$-[2(S)-{N-Methyl-N-(3-isopropylcarbamoylpropyl)aminocarbonyloxy}-3-phenylpropionyl]-N$^\alpha$-methyl-L-histidyl]amino-1-cyclohexyl-3(S)-hydroxy-6-methylheptane mp: 62°–66° C.

Rf: 0.38 (chloroform:methanol, 10:1, V/V).

(72) 2(S)-[N$^\alpha$-[2(S)-{N-Methyl-N-(3-oxo-5-methylhexyl)aminocarbonyloxy}-3-phenylpropionyl]-N$^\alpha$-methyl-L-histidyl]amino-1-cyclohexyl-3(S)-hydroxy-6-methylheptane mp: 68°–72° C.

Rf: 0.32 (chloroform:methanol, 10:1, V/V).

(73) 2(S)-[N$^\alpha$-[2(S)-{N-(2-Isopropylthioethyl)-N-methylaminocarbonyloxy}-3-phenylpropionyl]-N$^\alpha$-methyl-L-histidyl]amino-1-cyclohexyl-3(S)-hydroxy-6-methylheptane mp: 70°–74° C.

Rf: 0.46 (chloroform:methanol, 10:1, V/V).

(74) 2(S)-[Nα-[2(S)-{N-(2-Isopropylsulfonylethyl)-N-methylaminocarbonyloxy}-3-phenylpropionyl]-Nα-methyl-L-histidyl]amino-1-cyclohexyl-3(S)-hydroxy-6-methylheptane mp: 68°-71° C.

Rf: 0.42 (chloroform:methanol, 10:1, V/V).

(75) 2(S)-[Nα-{2(S)-(2-Acetylperhydropyridazine-1-carbonyloxy)-3-phenylpropionyl}-Nα-methyl-L-histidyl]amino-1-cyclohexyl-3(S)-hydroxy-6-methylheptane mp: 80°-84° C.

Rf: 0.39 (chloroform:methanol, 9:1, V/V).

(76) 2(S)-[Nα-{2(S)-(2-Butyrylperhydropyridazine-1-carbonyloxy)-3-phenylpropionyl}-Nα-methyl-L-histidyl]amino-1-cyclohexyl-3(S)-hydroxy-6-methylheptane mp: 73°-77° C.

Rf: 0.58 (chloroform:methanol, 9:1, V/V).

(77) 2(S)-[Nα-{2(S)-(2-Isobutyrylperhydropyridazine-1-carbonyloxy)-3-phenylpropionyl}-Nα-methyl-L-histidyl]amino-1-cyclohexyl-3(S)-hydroxy-6-methylheptane mp: 73°-81° C.

Rf: 0.36 (chloroform:methanol, 9:1, V/V)..

(78) 2(S)-[Nα-{2(S)-(2-Benzoylperhydropyridazinze-1-carbonyloxy)-3-phenylpropionyl}-Nα-methyl-L-histidyl]amino-1-cyclohexyl-3(S)-hydroxy-6-methylheptane mp: 77°-82° C.

Rf: 0.49 (chloroform:methanol, 9:1, V/V).

(79) 2(S)-[Nα-{2(S)-(2-Cyclohexylcarbonylperhydropyridazine-1-carbonyloxy)-3-phenylpropionyl}-Nα-methyl-L-histidyl]amino-1-cyclohexyl-3(S)-hydroxy-6-methylheptane mp: 70°-76° C.

Rf: 0.38 (chloroform:methanol, 9:1, V/V).

(80) 2(S)-[Nα-{2(S)-(2-Acetylpyrazolidine-1-carbonyloxy)-3-phenylpropionyl}-Nα-methyl-L-histidyl]amino-1-cyclohexyl-3(S)-hydroxy-6-methylheptane mp: 77°-82° C.

Rf: 0.30 (chloroform:methanol, 9:1, V/V).

(81) 2(S)-[Nα-{2(S)-(2-Isobutyrylpyrazolidine-1-carbonyloxy)-3-phenylpropionyl}-Nα-methyl-L-histidyl]amino-1-cyclohexyl-3(S)-hydroxy-6-methylheptane mp: 66°-73° C.

Rf: 0.33 (chloroform:methanol, 9:1, V/V).

(82) 2(S)-[Nα-{2(S)-(2-Methoxyacetylpyrazolidine-1-carbonyloxy)-3-phenylpropionyl}-Nα-methyl-L-histidyl]amino-1-cyclohexyl-3(S)-hydroxy-6-methylheptane mp: 80°-84° C.

Rf: 0.34 (chloroform:methanol, 9:1, V/V).

(83) 2(S)-[Nα-[2(S)-{2-(4-Dimethylaminobutyryl)-pyrazolidine-1-carbonyloxy}-3-phenylpropionyl]-Nα-methyl-L-histidyl]amino-1-cyclohexyl-3(S)-hydroxy-6-methylheptane mp: 58°-63° C.

Rf: 0.05 (chloroform:methanol, 9:1, V/V).

(84) 2(S)-[Nα-{2(S)-(2-Benzoylaminoacetylpyrazolidine-1carbonyloxy}-3-phenylpropionyl}-Nα-methyl-L-histidyl]amino-1-cyclohexyl-3(S)-hydroxy-6-methylheptane mp: 98°-102° C.

Rf: 0.35 (chloroform:methanol, 9:1, V/V).

(85) 2(S)-[Nα-{2(S)-(2-Methylcarbamoylpyrazolidine-1-carbonyloxy)-3-phenylpropionyl}-Nα-methyl-L-histidyl]amino-1-cyclohexyl-3(S)-hydroxy-6-methylheptane mp: 80°-83° C.

Rf: 0.40 (chloroform:methanol, 9:1, V/V).

(86) 2(S)-[Nα-{2(S)-(2-Morpholinocarbonylpyrazolidine-1-carbonyloxy)-3-phenylpropionyl}-Nα-methyl-L-histidyl]amino-1-cyclohexyl-3(S)-hydroxy-6-methylheptane mp: 79°-87° C.

Rf: 0.28 (chloroform:methanol, 9:1, V/V).

(87) 2(S)-[Nα-[2(S)-{2-(N-t-Butoxycarbonyl-L-leucyl)pyrazolidine-1-carbonyloxy}-3-phenylpropionyl]-Nα-methyl-L-histidyl]amino-1-cyclohexyl-3(S)-hydroxy-6-methylheptane mp: 83°-89° C.

Rf: 0.39 (chloroform:methanol, 9:1, V/V).

(88) 2(S)-[Nα-[2(S)-{2-(N-Acetyl-L-leucyl)pyrazolidine-1-carbonyloxy}-3-phenylpropionyl]-Nα-methyl-L-histidyl]amino-1-cyclohexyl-3(S)-hydroxy-6-methylheptane mp: 85°-93° C.

Rf: 0.26 (Chloroform:methanol, 9:1, V/V).

(89) 2(S)-[Nα-[2(S)-{2-(Nα-t-Butoxycarbonyl-L-histidyl)pyrazolidine-1-carbonyloxy}-3-phenylpropionyl]-Nα-methyl-L-histidyl]amino-1-cyclohexyl-3(S)-hydroxy-6-methylheptane mp: 74°-81° C.

Rf: 0.21 (chloroform:methanol, 9:1, V/V).

(90) 2(S)-[Nα-{2(S)-(4-Methylpiperazine-1-carbonyloxy)-3-phenylpropionyl}-Nα-methyl-L-histidyl]amino-1-cyclohexyl-3(S)-hydroxy-6-methylheptane mp: 82°-86° C.

Rf: 0.19 (chloroform:methanol, 9:1, V/V).

(91) 2(S)-[Nα-{2(S)-(4-Methylcarbamoylpiperazine-1-carbonyloxy)-3-phenylpropionyl}-Nα-methyl-L-histidyl]amino-1-cyclohexyl-3(S)-hydroxy-6-methylheptane mp: 107°-112° C.

Rf: 0.37 (chloroform:methanol, 9:1, V/V).

(92) 2(S)-[Nα-[2(S)-{4-(t-Butoxycarbonylglycyl)piperazine-1-carbonyloxy}-3-phenylpropionyl]-Nα-methyl-L-histidyl]amino-1-cyclohexyl-3(S)-hydroxy-6-methylheptane mp: 84°-89° C.

Rf: 0.19 (chloroform:methanol, 9:1, V/V).

(93) 2(S)-[Nα-[2(S)-{4-(Morpholinocarbonyl)piperazine-1-carbonyloxy}-3-phenylpropionyl]-Nα-methyl-L-histidyl]amino-1-cyclohexyl-3(S)-hydroxy-6-methylheptane mp: 81°-88° C.

Rf: 0.24 (chloroform:methanol, 9:1, V/V).

(94) 2(S)-[Nα-{2(S) (3-Oxopyrrolidine-1-carbonyloxy)-3phenylpropionyl}-Nα-methyl-L-histidyl]amino-1-cyclohexyl-3(S)-hydroxy-6-methylheptane mp: 80°-84° C.

Rf: 0.40 (chloroform:methanol, 9:1, V/V).

(95) 2(S)-[Nα-{2(S)-(2-Oxazolidinone-3-carbonyloxy)-3-phenylpropionyl}-Nα-methyl-L-histidyl]amino-1-cyclohexyl-3(S)-hydroxy-6-methylheptane mp: 82°-89° C.

Rf: 0.25 (chloroform:methanol, 9:1, V/V).

(96) 2(S)-[Nα-{2(S)-(1,2,3,6-Tetrahydropyridine-1-carbonyloxy)-3-phenylpropionyl}-Nα-methyl-L-histidyl]amino-1-cyclohexyl-3(S)-hydroxy-6-methylheptane mp: 69°-74° C.

Rf: 0.38 (chloroform:methanol, 9:1, V/V).

(97) 2(S)-[Nα-{2(S)-(3-Thiazolidinecarbonyloxy)-3-phenylpropionyl}-Nα-methyl-L-histidyl]amino-1-cyclohexyl-3(S)-hydroxy-6-methylheptane mp: 76°–82° C.

Rf: 0.34 (chloroform:methanol, 9:1, V/V).

(98) 2(S)-[N$^\alpha$-{2(S)-(1-Oxothiazolidine-3-carbonyloxy)-3-phenylpropionyl}-N$^\alpha$-methyl-L-histidyl]amino-1-cyclohexyl-3(S)-hydroxy-6-methylheptane mp: 90°–96° C.

Rf: 0.22 (chloroform:methanol, 9:1, V/V).

(99) 2(S)-[N$^\alpha$-{2(S)-(1,1-Dioxothiazolidine-3-carbonyloxy)-3-phenylpropionyl}-N$^\alpha$-methyl-L-histidyl]amino-1-cyclohexyl-3(S)-hydroxy-6-methylheptane mp: 89°–95° C.

Rf: 0.32 (chloroform:methanol, 9:1, V/V).

(100) 2(S)-[N$^\alpha$-{2(S)-(Thiomorpholinocarbonyloxy)-3phenylpropionyl}-N$^\alpha$-methyl-L-histidyl]amino-1-cyclohexyl-3(S)-hydroxy-6-methylheptane mp: 78°–82° C.

Rf: 0.36 (chloroform:methanol, 9:1, V/V).

(101) 2(S)-[N$^\alpha$-{2(S)-(1-Oxothiomorpholinocarbonyloxy)-3-phenylpropionyl}-N$^\alpha$-methyl-L-histidyl]amino-1-cyclohexyl-3(S)-hydroxy-6-methylheptane mp: 90°–96° C.

Rf: 0.23 (chloroform:methanol, 9:1, V/V).

(102) 2(S)-[N$^\alpha$-{2(S)-(1,1-Dioxothiomorpholinocarbonyloxy)-3-phenylpropionyl}-N$^\alpha$-methyl-L-histidyl]amino-1-cyclohexyl-3(S)-hydroxy-6-methylheptane mp: 99°–103° C.

Rf: 0.31 (chloroform:methanol, 9:1, V/V).

(103) 2(S)-[N$^\alpha$-{2(S)-(2(R)-Methyl-3(R)-dimethylcarbamoylmorpholinocarbonyloxy)-3-phenylpropionyl}-N$^\alpha$-methyl-L-histidyl]amino-1-cyclohexyl-3(S)-hydroxy-6-methylheptane mp: 92°–97° C.

Rf: 0.45 (chloroform:methanol, 10:1, V/V).

(104) 2(S)-[N$^\alpha$-{2(S)-(2(S)-Isobutyl-4-methyl-3-oxopiperazine-1-carbonyloxy)-3-phenylpropionyl}-N$^\alpha$-methyl-L-histidyl]amino-1-cyclohexyl-3(S)-hydroxy-6-methylheptane mp: 88°–92° C.

Rf: 0.50 (chloroform:methanol, 10:1, V/V).

(105) 2(S)-[N$^\alpha$-{2(S)-(6(S)-3(S)-Morpholinocarbonylmethyl-2-oxo-1,4-diazabicyclo[4.3.0]nonane-4-carbonyloxy)-3-phenylpropionyl}-N$^\alpha$-methyl-L-histidyl]amino-1-cyclohexyl-3(S)-hydroxy-6-methylheptane mp: 113°–117° C.

Rf: 0.37 (chloroform:methanol, 10:1, V/V).

EXAMPLE 6

(1) To a solution of N-t-butoxycarbonyl-L-histidine (363 mg) and 2(S)-amino-1-cyclohexyl-3(S)-hydroxy-6-methylheptane (294 mg) in dry N,N-dimethylformamide (30 ml) which was cooled to 0° C., were added a solution of diphenyl phosphorylazide (390 mg) in dry N,N-dimethylformamide (5 ml) and triethylamine (144 mg). The mixture was stirred overnight at ambient temperature. After evaporation of the solvent, the residue was dissolved in ethyl acetate (30 ml) and the solution was washed with 10% citric acid solution, saturated sodium bicarbonate solution and water successively, dried over magnesium sulfate, and concentrated under reduced pressure. The residue was purified with silica gel column chromatography (chloroform as eluent) to give 2(S)-(N-t-butoxycarbonyl-L-histidyl)amino-1-cyclohexyl-3(S)-hydroxy-6-methylheptane (384 mg) as an amorphous powder.

mp: 96°–100° C.

Rf: 0.47 (chloroform:methanol:acetic acid, 8:1:1, V/V).

(2) A solution of 2(S)-(N-t-butoxycarbonyl-L-histidyl)-amino-1-cyclohexyl-3(S)-hydroxy-6-methylheptane (383 mg) in trifluoroacetic acid (10 ml) was stirred at 0° C. for 30 minutes. After concentration of the mixture in vacuo, the residue was dissolved in ethyl acetate (20 ml). The solution was washed with saturated sodium bicarbonate solution, dried over magnesium sulfate, and concentrated in vacuo to give 2(S)-(L-histidyl)amino-1-cyclohexyl-3(S)-hydroxy-6-methylheptane (275 mg) as an amorphous powder.

mp: 126°–130° C.

Rf: 0.11 (chloroform:methanol:acetic acid, 8:1:1, V/V).

(3) To a mixture of 2(S)-morpholinocarbonyloxy-3-phenylpropionic acid (120 mg) and 2(S)-(L-histidyl)amino-1-cyclohexyl-3(S)-hydroxy-6-methylheptane (142 mg) in dry N,N-dimethylformamide (20 ml), which was cooled to 0° C., were added a solution of diphenyl phosphorylazide (108 mg) in dry N,N-dimethylformamide (5 ml) and triethylamine (40 mg). The mixture was stirred for 16 hours at ambient temperature. After evaporation of the solvent, the residue was dissolved in ethyl acetate (30 ml). The solution was washed with 1M sodium bicarbonate solution and water successively, dried over magnesium sulfate, and concentrated under reduced pressure. The residue was purified with silica gel thin layer chromatography (chloroform:methanol, 6:1, V/V) to give 2(S)-[N$^\alpha$-(2(S)-morpholinocarbonyloxy-3-phenylpropionyl)-L-histidyl]amino-1-cyclohexyl-3(S)-hydroxy-6-methylheptane (177 mg) as an amorphous powder.

Rf: 0.63 (chloroform:methanol, 6:1, V/V).

EXAMPLE 7

The following compounds were obtained according to a similar manner to that of Example 6.

(1) 2(S)-[N$^\alpha$-{2(S)-(N,N-Diethylaminocarbonyloxy)-3-phenylpropionyl}-L-histidyl]amino-1-cyclohexyl-3(S)-hydroxy-6-methylheptane mp: 73°–77° C.

Rf: 0.49 (chloroform:methanol, 6:1, V/V).

(2) 2(S)-[N$^\alpha$-[2(S)-{N-(2-Morpholinocarbonylethyl)-N-methylaminocarbonyloxy}-3-phenylpropionyl]-L-histidyl]amino-1-cyclohexyl-3(S)-hydroxy-6-methylheptane mp: 82°–86° C.

Rf: 0.49 (chloroform:methanol, 9:1, V/V).

(3) 2(S)-[N$^\alpha$-[2(S)-{N'-(Morpholinocarbonyl)-N,N'-dimethylhydrazinocarbonyloxy}-3-phenylpropionyl]-L-histidyl]amino-1-cyclohexyl-3(S)-hydroxy-6-methylheptane mp: 76°–80° C.

Rf: 0.48 (chloroform:methanol, 10:1, V/V).

EXAMPLE 8

A solution of 2(S)-[N$^\alpha$-[2(S)-[N-methyl-N-{2-(N-t-butoxycarbonyl-N-methylamino)ethyl}aminocarbonyloxy]-3-phenylpropionyl]-N$^\alpha$-methyl-L-histidyl]amino-1-cyclohexyl-3(S)-hydroxy-6-methylheptane (114 mg) in trifluoroacetic acid (10 ml) was stirred at 0° C. for 1 hour. After evaporation of the solvent, the residue was dissolved in ethyl acetate (20 ml) and the solution was washed with 1M sodium bicarbonate solution and water successively, and dried over magnesium sulfate. Evaporation of the solvent gave 2(S)-[N$^\alpha$-[2(S)-{N-methyl-N-(2-methylaminoethyl)aminocarbonyloxy}-3-phenylpropionyl]-N$^\alpha$-methyl-L-histidyl]amino-1- cyclohexyl-3(S)-hydroxy-6-methylheptane (88 mg) as an amorphous powder.

mp: 65°-68° C.

Rf: 0.20 (chloroform:methanol, 6:1, V/V).

EXAMPLE 9

(1) To a solution of 2(S)-(N$^\alpha$-t-butoxycarbonyl-N$^\alpha$-methyl-N$^{im}$-tosyl-L-histidyl)amino-1-cyclohexyl-3(S)-hydroxy-6-methylheptane (200 g) in tetrahydrofuran (2 l) and methanol (500 ml) were added 1-hydroxybenzotriazole (128.1 g) and 3-(N,N-dimethylamino)propylamine (32.3 g) at ambient temperature. The mixture was stirred at the same temperature for 16 hours. After evaporation of the solvent, the residue was dissolved in ethyl acetate (800 ml) and the solution was washed with 1M sodium bicarbonate solution and water successively, dried over magnesium sulfate, and concentrated under reduced pressure. The residue was dissolved in trifluoroacetic acid (500 ml) and methylene chloride (500 ml) and the solution was stirred at ambient temperature for 2 hours. After evaporation of the solvent, the residue was dissolved in water (1 l). After 28% ammonium hydroxide was added to the solution to be neutral, the solution was extracted with methylene chloride (1 l×2). The combined extract was washed with 1M sodium bicarbonate solution and water successively, dried over magnesium sulfate, and concentrated in vacuo. The residue was crystallized from diethyl ether (2 l) to give 2(S)-(N$^\alpha$-methyl-L-histidyl)amino-1-cyclohexyl-3(S)-hydroxy-6-methylheptane (46.0 g).

Rf: 0.16 (chloroform:methanol:acetic acid, 8:1:1, V/V).

(2) To a solution of 2(S)-(N$^\alpha$-methyl-L-histidyl)amino-1-cyclohexyl-3(S)-hydroxy-6-methylheptane (900 mg) and triethylamine (494 mg) in methylene chloride (20 ml) was added trityl chloride (696 mg) at 0° C. The mixture was stirred at the same temperature for 1 hour. After evaporation of the solvent, the residue was dissolved in ethyl acetate (30 ml) and the solution was washed with 1M sodium bicarbonate solution and water successively, and dried over magnesium sulfate. Evaporation of the solvent gave 2(S)-(N$^\alpha$-methyl-N$^{im}$-trityl-L-histidyl)amino-1-cyclohexyl-3(S)-hydroxy-6-methylheptane (1.46 g) as an amorphous powder.

Rf: 0.43 (chloroform:methanol, 10:1, V/V).

(3) To a solution of 2(S)-[N-methyl-N-[2-{N-(morpholinocarbonyl)-N-methylamino}ethyl]aminocarbonyloxy]-3-phenylpropionic acid (976 mg) in dry methylene chloride (20 ml) which was cooled to 0° C., were added oxalyl chloride (0.22 ml) and three drops of N,N-dimethylformamide. The mixture was stirred at the same temperature for 1 hour and was added to a solution of 2(S)-(N$^\alpha$-methyl-N$^{im}$-trityl-L-histidyl)amino-1-cyclohexyl-3(S)-hydroxy-6-methylheptane (1.40 g) and N-methylmorpholine (502 mg) in methylene chloride (20 ml) at 0° C. The mixture was stirred at the same temperature for 1 hour. After evaporation of the solvent, the residue was dissolved in ethyl acetate (30 ml) and the solution was washed with 5% hydrochloric acid, 1M sodium bicarbonate solution and water successively, and dried over magnesium sulfate. Evaporation of the solvent gave 2(S)-[N$^\alpha$-[2(S)-[N-methyl-N-[2-{N-(morpholinocarbonyl)-N-methylamino}ethyl]aminocarbonyloxy]-3-phenylpropionyl]-N$^\alpha$-methyl-N$^{im}$-trityl-L-histidyl]amino-1-cyclohexyl-3(S)-hydroxy-6-methylheptane (2.21 g) as an amorphous powder.

Rf: 0.80 (chloroform:methanol, 10:1, V/V).

(4) 2(S)-[N$^\alpha$-[2(S)-[N-Methyl-N-[2-{N-(morpholinocarbonyl)-N-methylamino}ethyl]aminocarbonyloxy]-3-phenylpropionyl]-N$^\alpha$-methyl-N$^{im}$-trityl-L-histidyl]amino-1-cyclohexyl-3(S)-hydroxy-6-methylheptane (1.00 g) was dissolved in 50% acetic acid (20 ml) and the solution was heated at 60° C. for 1 hour. After cooling to the ambient temperature, resulting triphenylcarbinol was filtered off and the filtrate was concentrated under reduced pressure. The residue was dissolved in ethyl acetate (50 ml) and the solution was washed with 1M sodium bicarbonate solution and water successively, dried over magnesium sulfate, and concentrated in vacuo. The residue was purified by silica gel column chromatography (5% methanol in chloroform as eluent) to give 2(S)-[N$^\alpha$-[2(S)-[N-methyl-N-[2-{N-(morpholinocarbonyl)-N-methylamino}ethyl]aminocarbonyloxy]-3-phenylpropionyl]-N$^\alpha$-methyl-L-histidyl]amino-1-cyclohexyl-3(S)-hydroxy-6-methylheptane (700 mg) as an amorphous powder.

Rf: 0.45 (chloroform:methanol, 10:1, V/V).

EXAMPLE 10

To a solution of 2(S)-[N$^\alpha$-[2(S)-{N-(2-morpholinocarbonylethyl)-N-methylaminocarbonyloxy}-3-phenylpropionyl]-N$^\alpha$-methyl-L-histidyl]amino-1-cyclohexyl-3(S)-hydroxy-6-methylheptane (4.55 g) in ethanol (50 ml) which was cooled to 0° C., was added 4N hydrogen chloride in dioxane solution (1.9 ml). After the mixture was stirred at the same temperature for 10 minutes, the solvent was evaporated under reduced pressure. The residue was crystallized from ethanol (5 ml) and ethyl acetate (150 ml) to give 2(S)-[N$^\alpha$-[2(S)-{N-(2-morpholinocarbonylethyl)-N-methylaminocarbonyloxy}-3-phenylpropionyl]-N$^\alpha$-methyl-L-histidyl]amino-1-cyclohexyl-3(S)-hydroxy-6-methylheptane monohydrochloride (3.93 g).

mp: 175°-177° C.

[α]$_D^{20}$: −51.93° (c 1.0, MeOH).

EXAMPLE 11

The following compounds were obtained according to a similar manner to that of Example 10.

(1) 2(S)-[N$^\alpha$-[2(S)-[N-Methyl-N-{2-(N-isobutyryl-N-methylamino)ethyl}aminocarbonyloxy]-3-phenylpropionyl]-N$^\alpha$-methyl-L-histidyl]amino-1-cyclohexyl-3(S)-hydroxy-6-methylheptane monohydrochloride mp: 118°-122° C.

(2) 2(S)-[N$^\alpha$-[2(S)-[N-Methyl-N-[2-{N-(morpholinocarbonyl)-N-methylamino}ethyl]aminocarbonyloxy]-3-phenylpropionyl]-N$^\alpha$-methyl-L-histidyl]amino-1-cyclohexyl-3(S)-hydroxy-6-methylheptane monohydrochloride mp: 108°-116° C.

What we claim is:

1. A compound of the formula:

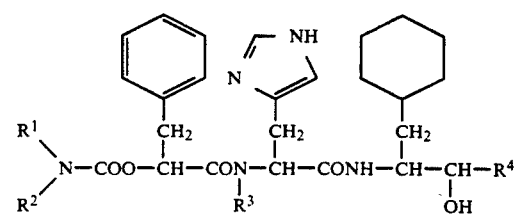

wherein

R¹ is lower alkyl substituted with a substituent selected from the group consisting of acyl, lower alkoxy, aryl, lower alkylthio and a group of the formula:

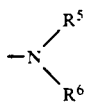

in which
R⁵ is hydrogen or acyl and
R⁶ is hydrogen or lower alkyl; aryl; or amino optionally substituted with substituent(s) selected from the group consisting of lower alkyl and acyl;
R² is hydrogen or lower alkyl;
R³ is hydrogen or lower alkyl; and
R⁴ is lower alkyl;
and its pharmaceutically acceptable salt.

2. A compound of the formula

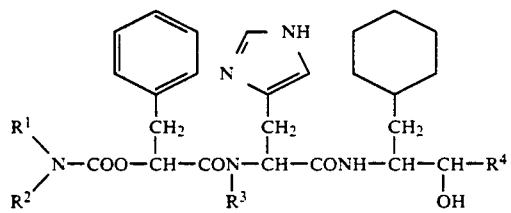

wherein
R¹ is lower alkyl substituted with a substituent selected from the group consisting of lower alkoxy, aryl, lower alkylthio, a group of the formula:

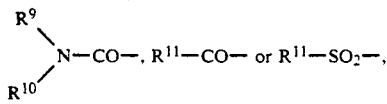

in which
R⁹ and R¹⁰ are each hydrogen, aryl, cyclo(lower)alkyl, morpholino, pyridyl, thiazolyl or lower alkyl optionally substituted with a substituent selected from the group consisting of lower alkoxycarbonyl, lower alkoxy, aryl, morpholino, pyridyl and thiazolyl, or
R⁹ and R¹⁰ are taken together with the attached nitrogen atom to form morpholino, thiomorpholino, its 1-oxide or 1,1-dioxide, pyrrolidin-1-yl, pyrazolidin-1-yl, piperidino, piperazin-1-yl, pyrrolin-1-yl, thiazolidin-3-yl, its 1-oxide or 1,1-dioxide, oxazolidin-3-yl, perhydropyridazin-1-yl, 1,4-dihydropyridin-1-yl, 1,2,3,6-tetrahydropyridin-1-yl, 1,2,3,4-tetrahydroisoquinolin-2-yl, 1,2,3,4-tetrahydroquinolin-1-yl, hexamethyleneimino or 1,4-diazobicyclo[4.3.0]nonan-4-yl, each of which is optionally substituted with lower alkyl, and
R¹¹ is aryl, cyclo(lower)alkyl, lower alkyl optionally substituted with a substituent selected from the group consisting of lower alkoxy and mono- or di(lower)alkylamino, or lower alkoxy optionally substituted with a substituent selected from the group consisting of lower alkanoyl and aryl, and a group of the formula:

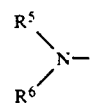

in which R⁵ is hydrogen or a group of the formula:

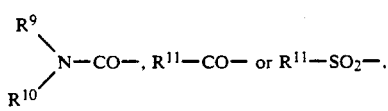

in which R⁹, R¹⁰ and R¹¹ are each as defined above, and R⁶ is hydrogen or lower alkyl; aryl; or amino optionally substituted with substituent(s) selected from the group consisting of lower alkyl and a group of the formula:

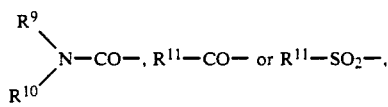

in which R⁹, R¹⁰, R¹¹ are each as defined above; and
R² is hydrogen or lower alkyl.

3. A compound of claim 2, wherein
R¹ is lower alkyl substituted with a group of the formula:

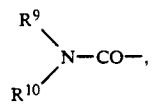

in which
R⁹ and R¹⁰ are each hydrogen or lower alkyl, or
R⁹ and R¹⁰ are taken together with the attached nitrogen atom to form morpholino.

4. A compound of claim 3, which is 2(S)-[Nα-[2(S)-{N-(2-morpholinocarbonylethyl)-N-methylaminocarbonyloxy}-3-phenylpropionyl]-Nα-methyl-L-histidyl]amino-1-cyclohexyl-3(S)-hydroxy-6-methylheptane or its hydrochloride.

5. A compound of claim 2, wherein
R¹ is lower alkyl substituted with a group of the formula:

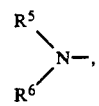

in which R⁵ is hydrogen or a group of the formula:

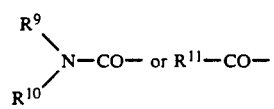

in which

R⁹ and R¹⁰ are taken together with the attached nitrogen atom to form morpholino, and R¹¹ is lower alkyl, and R⁶ is hydrogen or lower alkyl.

6. A compound of claim 5, which is 2(S)-[Nα-[2(S)-[N-methyl-N-[2-{N-(morpholinocarbonyl)-N-methylamino}ethyl]aminocarbonyloxy]-3-phenylpropionyl]-Nα-methyl-L-histidyl]amino-1-cyclohexyl-3(S)-hydroxy-6-methylheptane or its hydrochloride.

7. A compound of claim 5, which is 2(S)-[Nα-[2(S)-[N-methyl-N-{2-(N-isobutyryl-N-methylamino)ethyl}aminocarbonyloxy]-3-phenylpropionyl]-Nα-methyl-L-histidyl]amino-1-cyclohexyl-3(S)-hydroxy-6-methylheptane or its hydrochloride.

8. A compound of claim 2, wherein

R¹ is amino optionally substituted with substituent(s) selected from the group consisting of lower alkyl and a group of the formula:

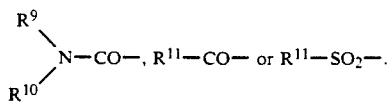

9. A pharmaceutical composition comprising a compound of claim 1, as an active ingredient, in association with a pharmaceutically acceptable, substantially non-toxic carrier or excipient.

10. A method for the therapeutic treatment of hypertension and heart failure which comprises administering an effective amount of a compound of claim 1 in human being or animals.

* * * * *

UNITED STATES PATENT AND TRADEMARK OFFICE
CERTIFICATE OF CORRECTION

PATENT NO. : 5,223,489
DATED : June 29, 1993
INVENTOR(S) : Keiji Hemmi et al.

It is certified that error appears in the above-indentified patent and that said Letters Patent is hereby corrected as shown below:

On the title page, Item [73],

The assignee's name is spelled incorrectly, should read:

--Fujisawa Pharmaceutical Co., Ltd.--

Signed and Sealed this

First Day of March, 1994

Attest:

BRUCE LEHMAN

*Attesting Officer*    *Commissioner of Patents and Trademarks*